United States Patent
Ozaki et al.

(10) Patent No.: US 9,850,906 B2
(45) Date of Patent: Dec. 26, 2017

(54) ROTATION DRIVE DEVICE AND CENTRIFUGAL PUMP APPARATUS EMPLOYING SAME

(71) Applicant: TC1 LLC, Pleasanton, CA (US)

(72) Inventors: Takayoshi Ozaki, Shizuoka (JP); Hiroyuki Yamada, Shizuoka (JP); Ken Sugiura, Shizuoka (JP); Takehisa Mori, Kanagawa (JP); Takeshi Tsubouchi, Kanagawa (JP)

(73) Assignee: TC1 LLC, Pleasanton, CA (US)

( * ) Notice: Subject to any disclaimer, the term of this patent is extended or adjusted under 35 U.S.C. 154(b) by 224 days.

(21) Appl. No.: 14/034,730

(22) Filed: Sep. 24, 2013

(65) Prior Publication Data

US 2014/0030122 A1 Jan. 30, 2014

Related U.S. Application Data

(63) Continuation of application No. PCT/JP2012/056244, filed on Mar. 12, 2012.

(30) Foreign Application Priority Data

Mar. 28, 2011 (JP) .................................. 2011-070286

(51) Int. Cl.

| | |
|---|---|
| F04D 13/06 | (2006.01) |
| F04D 25/06 | (2006.01) |
| H02K 49/10 | (2006.01) |
| H02K 7/09 | (2006.01) |
| F04D 29/048 | (2006.01) |
| H02K 21/16 | (2006.01) |
| H02K 21/22 | (2006.01) |

(Continued)

(52) U.S. Cl.
CPC ..... F04D 13/0693 (2013.01); F04D 13/0606 (2013.01); F04D 13/0666 (2013.01);
(Continued)

(58) Field of Classification Search
CPC .. F04D 13/0666; F04D 25/026; F04D 29/048; F04D 1/00; F04D 7/02;
(Continued)

(56) References Cited

U.S. PATENT DOCUMENTS

| | | |
|---|---|---|
| 1,093,868 A | 4/1914 | Leighty |
| 2,684,035 A | 7/1954 | Kemp |

(Continued)

FOREIGN PATENT DOCUMENTS

| | | |
|---|---|---|
| CN | 1347585 A | 5/2002 |
| CN | 1462344 A | 12/2003 |

(Continued)

OTHER PUBLICATIONS

Asama, et al., "Suspension Performance of a Two-Axis Actively Regulated Consequent-Pole Bearingless Motor," IEEE Transactions on Energy Conversion, vol. 28, No. 4, Dec. 2013, 8 pages.

(Continued)

*Primary Examiner* — Bryan Lettman
*Assistant Examiner* — Charles W Nichols
(74) *Attorney, Agent, or Firm* — Kilpatrick Townsend & Stockton LLP

(57) ABSTRACT

This centrifugal blood pump apparatus includes an impeller (10) provided in a blood chamber (7), and a plurality of coils (20) provided in a motor chamber (8) for driving the impeller (10) to rotate with a dividing wall (6) interposed therebetween. A flexible substrate (23) in the shape of a strip is arranged to surround outer circumferences of the plurality of coils (20), and is connected to the plurality of coils (20) and a connector (24). A driving voltage (VU, VV, VW) is externally supplied to the plurality of coils (20) via the connector (24) and the flexible substrate (23). Thus, assembling workability, productivity and reliability are improved.

26 Claims, 36 Drawing Sheets

(51) Int. Cl.
| | |
|---|---|
| *H02K 21/24* | (2006.01) |
| *H02K 3/52* | (2006.01) |
| *H02K 5/128* | (2006.01) |
| *H02K 5/22* | (2006.01) |
| *H02K 7/14* | (2006.01) |
| *H02K 19/10* | (2006.01) |
| *F04D 25/02* | (2006.01) |
| *H02K 1/27* | (2006.01) |
| *H02K 3/28* | (2006.01) |
| *A61M 1/10* | (2006.01) |
| *A61M 1/12* | (2006.01) |

(52) U.S. Cl.
CPC ....... *F04D 25/026* (2013.01); *F04D 25/0633* (2013.01); *F04D 29/048* (2013.01); *H02K 1/2793* (2013.01); *H02K 3/28* (2013.01); *H02K 3/522* (2013.01); *H02K 5/128* (2013.01); *H02K 5/1282* (2013.01); *H02K 5/225* (2013.01); *H02K 7/09* (2013.01); *H02K 7/14* (2013.01); *H02K 19/103* (2013.01); *H02K 21/16* (2013.01); *H02K 21/22* (2013.01); *H02K 21/24* (2013.01); *H02K 49/108* (2013.01); *A61M 1/101* (2013.01); *A61M 1/1012* (2014.02); *A61M 1/1015* (2014.02); *A61M 1/1017* (2014.02); *A61M 1/1031* (2014.02); *A61M 1/1086* (2013.01); *A61M 1/122* (2014.02); *A61M 2205/3334* (2013.01); *H02K 2203/03* (2013.01); *H02K 2203/06* (2013.01)

(58) Field of Classification Search
CPC .... F04D 13/021; F04D 13/024; F04D 13/026; F04D 13/06; F04D 13/0693; F04D 29/047; F04D 29/42; F04D 29/406; F04D 29/426; F04D 25/0633; A61M 1/101; A61M 1/1031; A61M 1/1015; A61M 1/1017; H02K 3/28; H02K 3/30; H02K 3/32; H02K 3/522; H02K 5/128; H02K 5/1282; H02K 5/225; H02K 1/2793; H02K 19/103; H02K 21/16; H02K 21/22; H02K 21/24; H02K 5/132; H02K 7/09; H02K 5/12; Y10S 310/06
See application file for complete search history.

(56) References Cited

U.S. PATENT DOCUMENTS

| | | | |
|---|---|---|---|
| 3,023,334 A * | 2/1962 | Burr .......................... | H02K 3/26 310/268 |
| 3,510,229 A | 5/1970 | Smith | |
| 3,620,638 A | 11/1971 | Kaye et al. | |
| 3,870,382 A | 3/1975 | Reinhoudt | |
| 3,932,069 A | 1/1976 | Giardini et al. | |
| 3,960,468 A | 6/1976 | Boorse et al. | |
| 4,149,535 A | 4/1979 | Voider | |
| 4,382,199 A | 5/1983 | Isaacson | |
| 4,392,836 A | 7/1983 | Sugawara | |
| 4,434,389 A | 2/1984 | Langley et al. | |
| 4,507,048 A | 3/1985 | Belenger et al. | |
| 4,528,485 A | 7/1985 | Boyd, Jr. | |
| 4,540,402 A | 9/1985 | Aigner | |
| 4,549,860 A | 10/1985 | Yakich | |
| 4,645,961 A * | 2/1987 | Malsky .................. | H02K 1/278 310/156.07 |
| 4,686,982 A | 8/1987 | Nash | |
| 4,688,998 A | 8/1987 | Olsen et al. | |
| 4,753,221 A | 6/1988 | Kensey et al. | |
| 4,769,006 A | 9/1988 | Papantonakos | |
| 4,779,614 A | 10/1988 | Moise | |
| 4,790,843 A | 12/1988 | Carpentier et al. | |
| 4,806,080 A | 2/1989 | Mizobuchi et al. | |
| 4,817,586 A | 4/1989 | Wampler | |
| 4,846,152 A | 7/1989 | Wampler et al. | |
| 4,857,781 A | 8/1989 | Shih | |
| 4,888,011 A | 12/1989 | Kung et al. | |
| 4,895,557 A | 1/1990 | Moise et al. | |
| 4,900,227 A | 2/1990 | Trouplin | |
| 4,902,272 A | 2/1990 | Milder et al. | |
| 4,906,229 A | 3/1990 | Wampler | |
| 4,908,012 A | 3/1990 | Moise et al. | |
| 4,919,647 A | 4/1990 | Nash | |
| 4,930,997 A | 6/1990 | Bennett | |
| 4,944,722 A | 7/1990 | Carriker et al. | |
| 4,957,504 A | 9/1990 | Chardack | |
| 4,964,864 A | 10/1990 | Summers et al. | |
| 4,969,865 A | 11/1990 | Hwang et al. | |
| 4,985,014 A | 1/1991 | Orejola | |
| 4,995,857 A | 2/1991 | Arnold | |
| 5,021,048 A | 6/1991 | Buckholtz | |
| 5,078,741 A | 1/1992 | Bramm et al. | |
| 5,092,844 A | 3/1992 | Schwartz et al. | |
| 5,092,879 A | 3/1992 | Jarvik | |
| 5,100,374 A | 3/1992 | Kageyama | |
| 5,106,263 A | 4/1992 | Irie | |
| 5,106,273 A | 4/1992 | Lemarquand et al. | |
| 5,106,372 A | 4/1992 | Ranford | |
| 5,112,202 A | 5/1992 | Ozaki et al. | |
| 5,112,349 A | 5/1992 | Summers et al. | |
| 5,129,883 A | 7/1992 | Black | |
| 5,145,333 A | 9/1992 | Smith | |
| 5,147,186 A | 9/1992 | Buckholtz | |
| 5,190,528 A | 3/1993 | Fonger et al. | |
| 5,201,679 A | 4/1993 | Velte et al. | |
| 5,211,546 A | 5/1993 | Isaacson et al. | |
| 5,229,693 A | 7/1993 | Futami et al. | |
| 5,275,580 A | 1/1994 | Yamazaki | |
| 5,290,227 A | 3/1994 | Pasque | |
| 5,290,236 A | 3/1994 | Mathewson | |
| 5,300,112 A | 4/1994 | Barr | |
| 5,306,295 A | 4/1994 | Kolff et al. | |
| 5,312,341 A | 5/1994 | Turi | |
| 5,313,128 A * | 5/1994 | Robinson .................. | H02K 3/50 174/117 A |
| 5,332,374 A | 7/1994 | Kricker et al. | |
| 5,346,458 A | 9/1994 | Afield | |
| 5,350,283 A | 9/1994 | Nakazeki et al. | |
| 5,354,331 A | 10/1994 | Schachar | |
| 5,360,445 A | 11/1994 | Goldowsky | |
| 5,370,509 A | 12/1994 | Golding et al. | |
| 5,376,114 A | 12/1994 | Jarvik | |
| 5,385,581 A | 1/1995 | Bramm et al. | |
| 5,405,383 A | 4/1995 | Barr | |
| 5,449,342 A | 9/1995 | Hirose et al. | |
| 5,478,222 A | 12/1995 | Heidelberg et al. | |
| 5,504,978 A | 4/1996 | Meyer, III | |
| 5,507,629 A | 4/1996 | Jarvik | |
| 5,519,270 A | 5/1996 | Yamada et al. | |
| 5,533,957 A | 7/1996 | Aldea | |
| 5,569,111 A | 10/1996 | Cho et al. | |
| 5,575,630 A | 11/1996 | Nakazawa et al. | |
| 5,588,812 A | 12/1996 | Taylor et al. | |
| 5,595,762 A | 1/1997 | Derrieu et al. | |
| 5,611,679 A | 3/1997 | Ghosh et al. | |
| 5,613,935 A | 3/1997 | Jarvik | |
| 5,630,836 A | 5/1997 | Prem et al. | |
| 5,643,226 A | 7/1997 | Cosgrove et al. | |
| 5,678,306 A | 10/1997 | Bozeman, Jr. et al. | |
| 5,692,882 A | 12/1997 | Bozeman, Jr. et al. | |
| 5,695,471 A | 12/1997 | Wampler | |
| 5,708,346 A | 1/1998 | Schob | |
| 5,725,357 A | 3/1998 | Nakazeki et al. | |
| 5,738,649 A | 4/1998 | Macoviak | |
| 5,746,575 A | 5/1998 | Westphal et al. | |
| 5,746,709 A | 5/1998 | Rom et al. | |
| 5,749,855 A | 5/1998 | Reitan | |
| 5,755,784 A | 5/1998 | Jarvik | |
| 5,776,111 A | 7/1998 | Tesio | |
| 5,795,074 A | 8/1998 | Rahman et al. | |

(56) References Cited

U.S. PATENT DOCUMENTS

| | | |
|---|---|---|
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,843,129 A | 12/1998 | Larson et al. |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,890,883 A | 4/1999 | Golding et al. |
| 5,911,685 A | 6/1999 | Siess et al. |
| 5,917,295 A | 6/1999 | Mongeau |
| 5,917,297 A | 6/1999 | Gerster et al. |
| 5,921,913 A | 7/1999 | Siess |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Izraelev |
| 5,941,813 A | 8/1999 | Sievers et al. |
| 5,945,753 A * | 8/1999 | Maegawa ............... H02K 29/08 310/266 |
| 5,947,703 A | 9/1999 | Nojiri et al. |
| 5,951,263 A | 9/1999 | Taylor et al. |
| 5,964,694 A | 10/1999 | Siess et al. |
| 5,984,892 A | 11/1999 | Bedingham |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,058,593 A | 5/2000 | Siess |
| 6,066,086 A | 5/2000 | Antaki et al. |
| 6,071,093 A | 6/2000 | Hart |
| 6,074,180 A * | 6/2000 | Khanwilkar .......... A61M 1/101 415/900 |
| 6,080,133 A | 6/2000 | Wampler |
| 6,082,900 A | 7/2000 | Takeuchi et al. |
| 6,083,260 A | 7/2000 | Aboul-Hosn et al. |
| 6,086,527 A | 7/2000 | Talpade |
| 6,100,618 A | 8/2000 | Schoeb et al. |
| 6,123,659 A | 9/2000 | leBlanc et al. |
| 6,123,726 A | 9/2000 | Mori et al. |
| 6,139,487 A | 10/2000 | Siess |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,179,773 B1 | 1/2001 | Prem et al. |
| 6,190,304 B1 | 2/2001 | Downey et al. |
| 6,200,260 B1 | 3/2001 | Bolling |
| 6,206,659 B1 | 3/2001 | Izraelev |
| 6,254,359 B1 | 3/2001 | Aber |
| 6,222,290 B1 | 4/2001 | Schob et al. |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,247,892 B1 | 6/2001 | Kazatchkov et al. |
| 6,249,067 B1 | 6/2001 | Schob et al. |
| 6,264,635 B1 | 7/2001 | Wampler et al. |
| 6,268,675 B1 | 7/2001 | Amrhein |
| 6,276,831 B1 | 8/2001 | Takahashi et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,320,731 B1 | 11/2001 | Eeaves et al. |
| 6,245,007 B1 | 12/2001 | Bedingham et al. |
| 6,351,048 B1 | 2/2002 | Schob et al. |
| 6,355,998 B1 | 3/2002 | Schob et al. |
| 6,365,996 B2 | 4/2002 | Schob |
| 6,375,607 B1 | 4/2002 | Prem |
| 6,387,037 B1 | 5/2002 | Bolling et al. |
| 6,394,769 B1 | 5/2002 | Bearnson et al. |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,522,093 B1 | 2/2003 | Hsu et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,575,717 B2 | 6/2003 | Ozaki et al. |
| 6,589,030 B2 | 7/2003 | Ozaki |
| 6,595,762 B2 | 7/2003 | Khanwilkar et al. |
| 6,605,032 B2 | 8/2003 | Benkowski et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,641,378 B2 | 11/2003 | Davis et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,157 B2 | 4/2004 | Goldowsky |
| 6,716,189 B1 | 4/2004 | Jarvik et al. |
| 6,732,501 B2 | 5/2004 | Yu et al. |
| 6,749,598 B1 | 6/2004 | Keren et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,846,168 B2 * | 1/2005 | Davis ..................... F04B 17/03 417/423.7 |
| 6,860,713 B2 | 1/2005 | Hoover |
| 6,884,210 B2 | 4/2005 | Nose et al. |
| 6,935,344 B1 | 8/2005 | Aboul-Hosn et al. |
| 6,926,662 B1 | 9/2005 | Aboul-Hosn et al. |
| 6,942,672 B2 | 9/2005 | Heilman et al. |
| 6,949,066 B2 | 9/2005 | Beamson et al. |
| 6,966,748 B2 | 11/2005 | Woodard et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,048,681 B2 | 5/2006 | Tsubouchi et al. |
| 7,089,059 B1 | 8/2006 | Pless |
| 7,090,401 B2 | 8/2006 | Rahman et al. |
| 7,112,903 B1 | 9/2006 | Schob |
| 7,122,019 B1 | 10/2006 | Kesten et al. |
| 7,128,538 B2 | 10/2006 | Tsubouchi et al. |
| 7,027,875 B2 | 11/2006 | Siess et al. |
| 7,156,802 B2 | 1/2007 | Woodard et al. |
| 7,160,243 B2 | 1/2007 | Medvedev |
| 7,175,588 B2 | 2/2007 | Morello |
| 7,202,582 B2 * | 4/2007 | Eckert .................... H02K 3/522 310/68 R |
| 7,172,551 B2 | 6/2007 | Leasure |
| 7,241,257 B1 | 10/2007 | Ainsworth et al. |
| 7,284,956 B2 | 10/2007 | Nose et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,431,688 B2 | 10/2008 | Wampler et al. |
| 7,329,236 B2 | 12/2008 | Kesten et al. |
| 7,462,019 B1 * | 12/2008 | Allarie ................. A61M 1/101 417/423.12 |
| 7,467,930 B2 | 12/2008 | Ozaki et al. |
| 7,470,246 B2 | 12/2008 | Mori et al. |
| 7,476,077 B2 | 1/2009 | Woodard et al. |

(56) References Cited

U.S. PATENT DOCUMENTS

| | | |
|---|---|---|
| 7,491,163 B2 | 2/2009 | Viole et al. |
| 7,575,423 B2 | 8/2009 | Wampler |
| 7,645,225 B2 | 1/2010 | Medvedev et al. |
| 7,660,635 B1 | 2/2010 | Verness et al. |
| 7,699,586 B2 | 4/2010 | LaRose et al. |
| 7,748,964 B2 | 7/2010 | Yaegashi et al. |
| 7,731,675 B2 | 8/2010 | Aboul-Hosn et al. |
| 7,802,966 B2 | 9/2010 | Wampler et al. |
| 7,841,976 B2 | 11/2010 | McBride et al. |
| 7,862,501 B2 | 1/2011 | Woodard |
| 7,888,242 B2 | 2/2011 | Tanaka et al. |
| 7,934,909 B2 | 5/2011 | Nuesser et al. |
| 7,972,122 B2 | 7/2011 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,152,493 B2 | 4/2012 | LaRose et al. |
| 8,177,703 B2 | 5/2012 | Smith et al. |
| 8,226,373 B2 | 7/2012 | Yaegashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Akdis et al. |
| 8,535,211 B2 | 9/2013 | Campbell et al. |
| 8,585,290 B2 | 11/2013 | Bauer |
| 8,686,674 B2 | 4/2014 | Bi et al. |
| 8,770,945 B2 | 7/2014 | Ozaki et al. |
| 8,821,365 B2 | 9/2014 | Ozaki et al. |
| 8,827,661 B2 | 9/2014 | Mori |
| 8,652,024 B1 | 10/2014 | Yanai et al. |
| 8,864,644 B2 | 10/2014 | Yomtov |
| 8,870,552 B2 | 10/2014 | Ayre et al. |
| 8,968,174 B2 | 3/2015 | Yanai et al. |
| 9,039,595 B2 | 5/2015 | Ayre et al. |
| 9,067,005 B2 | 6/2015 | Ozaki et al. |
| 9,068,572 B2 | 6/2015 | Ozaki et al. |
| 9,109,601 B2 | 8/2015 | Mori |
| 9,132,215 B2 | 9/2015 | Ozaki et al. |
| 9,133,854 B2 | 9/2015 | Okawa et al. |
| 9,371,826 B2 | 6/2016 | Yanai et al. |
| 9,381,285 B2 | 7/2016 | Ozaki et al. |
| 9,382,908 B2 | 7/2016 | Ozaki et al. |
| 9,410,549 B2 | 8/2016 | Ozaki et al. |
| 9,556,873 B2 | 1/2017 | Yanai et al. |
| 2001/0039369 A1 | 11/2001 | Terentiev |
| 2002/0051711 A1* | 5/2002 | Ozaki ............... F04D 13/0666 417/45 |
| 2002/0058994 A1 | 5/2002 | Hill et al. |
| 2002/0094281 A1 | 7/2002 | Khanwilkar et al. |
| 2002/0095210 A1 | 7/2002 | Finnegan et al. |
| 2003/0023302 A1 | 1/2003 | Moe et al. |
| 2003/0045772 A1 | 3/2003 | Reich et al. |
| 2003/0072656 A1 | 4/2003 | Niwatsukino et al. |
| 2003/0144574 A1 | 7/2003 | Heilman et al. |
| 2003/0199727 A1 | 10/2003 | Burke |
| 2003/0236488 A1 | 12/2003 | Novak |
| 2003/0236490 A1 | 12/2003 | Novak |
| 2004/0007515 A1 | 1/2004 | Geyer |
| 2004/0015232 A1 | 1/2004 | Shu et al. |
| 2004/0024285 A1 | 2/2004 | Muckter |
| 2004/0030381 A1 | 2/2004 | Shu |
| 2004/0064012 A1 | 4/2004 | Yanai |
| 2004/0143151 A1 | 7/2004 | Mori et al. |
| 2004/0145337 A1 | 7/2004 | Morishita |
| 2004/0152944 A1 | 8/2004 | Medvedev et al. |
| 2004/0171905 A1 | 9/2004 | Yu et al. |
| 2004/0210305 A1 | 10/2004 | Shu et al. |
| 2004/0215050 A1 | 10/2004 | Morello |
| 2004/0263341 A1 | 12/2004 | Enzinna |
| 2005/0004418 A1 | 1/2005 | Morello |
| 2005/0008496 A1 | 1/2005 | Tsubouchi et al. |
| 2005/0025630 A1 | 2/2005 | Ayre et al. |
| 2005/0043665 A1 | 2/2005 | Vinci et al. |
| 2005/0073273 A1 | 4/2005 | Maslov et al. |
| 2005/0089422 A1 | 4/2005 | Ozaki et al. |
| 2005/0131271 A1 | 6/2005 | Benkowski et al. |
| 2005/0141887 A1 | 6/2005 | Lelkes |
| 2005/0194851 A1 | 9/2005 | Eckert et al. |
| 2005/0261542 A1 | 11/2005 | Abe et al. |
| 2005/0287022 A1 | 12/2005 | Yaegashi et al. |
| 2006/0024182 A1 | 2/2006 | Akdis et al. |
| 2006/0055274 A1 | 3/2006 | Kim |
| 2006/0127227 A1 | 6/2006 | Mehlhorn et al. |
| 2007/0073393 A1 | 3/2007 | Kung et al. |
| 2007/0078293 A1 | 4/2007 | Shambaugh, Jr. |
| 2007/0095648 A1 | 4/2007 | Wampler et al. |
| 2007/0114961 A1 | 5/2007 | Schwarzkopf |
| 2007/0134993 A1 | 6/2007 | Tamez et al. |
| 2007/0189648 A1 | 8/2007 | Kita et al. |
| 2007/0213690 A1 | 9/2007 | Phillips et al. |
| 2007/0231135 A1 | 10/2007 | Wampler et al. |
| 2007/0282298 A1 | 12/2007 | Mason |
| 2007/0297923 A1 | 12/2007 | Tada |
| 2008/0007196 A1 | 1/2008 | Tan et al. |
| 2008/0021394 A1 | 1/2008 | La Rose et al. |
| 2008/0030895 A1 | 2/2008 | Obara et al. |
| 2008/0119777 A1 | 5/2008 | Vinci et al. |
| 2008/0124231 A1 | 5/2008 | Yaegashi |
| 2008/0183287 A1 | 7/2008 | Ayre |
| 2008/0211439 A1 | 9/2008 | Yokota et al. |
| 2008/0281146 A1 | 11/2008 | Morello |
| 2009/0041595 A1 | 2/2009 | Garzaniti et al. |
| 2009/0060743 A1 | 3/2009 | McBride et al. |
| 2009/0074336 A1 | 3/2009 | Engesser et al. |
| 2009/0099406 A1 | 4/2009 | Salmonsen et al. |
| 2009/0171136 A1 | 7/2009 | Shambaugh, Jr. |
| 2009/0257693 A1 | 10/2009 | Aiello |
| 2009/0318834 A1 | 12/2009 | Fujiwara et al. |
| 2010/0168534 A1 | 7/2010 | Matsumoto et al. |
| 2010/0185280 A1 | 7/2010 | Ayre et al. |
| 2010/0222634 A1 | 9/2010 | Poirier |
| 2010/0234835 A1 | 9/2010 | Horikawa et al. |
| 2010/0256440 A1 | 10/2010 | Maher |
| 2010/0262039 A1 | 10/2010 | Fujiwara et al. |
| 2010/0266423 A1 | 10/2010 | Gohean et al. |
| 2010/0305692 A1 | 12/2010 | Thomas et al. |
| 2010/0324465 A1 | 12/2010 | Vinci et al. |
| 2011/0015732 A1 | 1/2011 | Kanebako |
| 2011/0112354 A1 | 5/2011 | Nishimura et al. |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2011/0129373 A1 | 6/2011 | Mori |
| 2011/0160519 A1 | 6/2011 | Arndt et al. |
| 2011/0218383 A1 | 9/2011 | Broen et al. |
| 2011/0218384 A1 | 9/2011 | Bachman et al. |
| 2011/0218385 A1 | 9/2011 | Bolyare et al. |
| 2011/0237978 A1 | 9/2011 | Fujiwara et al. |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0022645 A1 | 1/2012 | Burke |
| 2012/0035411 A1 | 2/2012 | LaRose et al. |
| 2012/0078030 A1 | 3/2012 | Bourque |
| 2012/0078031 A1 | 3/2012 | Burke et al. |
| 2012/0095281 A1 | 4/2012 | Reichenbach et al. |
| 2012/0130152 A1 | 5/2012 | Ozaki et al. |
| 2012/0226350 A1 | 9/2012 | Ruder et al. |
| 2012/0243759 A1 | 9/2012 | Fujisawa |
| 2012/0245681 A1 | 9/2012 | Casas et al. |
| 2012/0253103 A1 | 10/2012 | Robert |
| 2012/0308363 A1 | 12/2012 | Ozaki et al. |
| 2013/0030240 A1 | 1/2013 | Schima et al. |
| 2013/0121821 A1 | 5/2013 | Ozaki et al. |
| 2013/0158521 A1 | 6/2013 | Sobue |
| 2013/0170970 A1 | 7/2013 | Ozaki et al. |
| 2013/0178694 A1 | 7/2013 | Jeffery et al. |
| 2013/0225909 A1 | 8/2013 | Dormanen et al. |
| 2013/0243623 A1 | 9/2013 | Okawa et al. |
| 2013/0289334 A1 | 10/2013 | Badstibner et al. |

(56) References Cited

U.S. PATENT DOCUMENTS

| | | |
|---|---|---|
| 2013/0331711 A1 | 12/2013 | Mathur et al. |
| 2014/0066690 A1 | 3/2014 | Siebenhaar et al. |
| 2014/0066691 A1 | 3/2014 | Siebenhaar |
| 2014/0100413 A1 | 4/2014 | Casas et al. |
| 2014/0107399 A1 | 4/2014 | Spence |
| 2014/0142367 A1 | 5/2014 | Ayre et al. |
| 2014/0155682 A1 | 6/2014 | Jeffery et al. |
| 2014/0200389 A1 | 7/2014 | Yanai et al. |
| 2014/0205467 A1 | 7/2014 | Yanai et al. |
| 2014/0241904 A1 | 8/2014 | Yanai et al. |
| 2014/0275721 A1 | 9/2014 | Yanai et al. |
| 2014/0275727 A1 | 9/2014 | Bonde et al. |
| 2014/0296615 A1 | 10/2014 | Franano |
| 2014/0309481 A1 | 10/2014 | Medvedev et al. |
| 2014/0314597 A1 | 10/2014 | Allaire et al. |
| 2014/0323796 A1 | 10/2014 | Medvedev et al. |
| 2014/0343352 A1 | 11/2014 | Ardt et al. |
| 2015/0017030 A1 | 1/2015 | Ozaki et al. |
| 2015/0023803 A1 | 1/2015 | Fritz et al. |
| 2015/0078936 A1 | 3/2015 | Mori |
| 2015/0306290 A1 | 10/2015 | Rosenberg et al. |
| 2015/0367048 A1 | 12/2015 | Brown et al. |
| 2015/0374892 A1 | 12/2015 | Yanai et al. |
| 2016/0058929 A1 | 3/2016 | Medvedev et al. |
| 2016/0058930 A1 | 3/2016 | Medvedev et al. |
| 2016/0228628 A1 | 8/2016 | Medvedev et al. |
| 2016/0235898 A1 | 8/2016 | Yanai et al. |
| 2016/0235899 A1 | 8/2016 | Yu et al. |
| 2016/0235900 A1 | 8/2016 | Yanai et al. |
| 2016/0281720 A1 | 9/2016 | Yanai et al. |
| 2016/0281728 A1 | 9/2016 | Ozaki et al. |

FOREIGN PATENT DOCUMENTS

| | | |
|---|---|---|
| CN | 102239334 A | 11/2011 |
| CN | 102341600 A | 2/2012 |
| EP | 2945662 B1 | 9/1999 |
| EP | 971212 A1 | 1/2000 |
| EP | 1113117 A2 | 7/2001 |
| EP | 1327455 A | 7/2003 |
| EP | 1430919 A1 | 6/2004 |
| EP | 1495773 A2 | 1/2005 |
| EP | 1598087 A2 | 3/2005 |
| EP | 1526286 A1 | 4/2005 |
| EP | 1495773 A3 | 11/2006 |
| EP | 1495773 B1 | 2/2009 |
| EP | 2292282 A1 | 3/2011 |
| EP | 2298375 A1 | 3/2011 |
| EP | 2372160 A1 | 10/2011 |
| EP | 2405140 A1 | 1/2012 |
| EP | 2405141 A1 | 1/2012 |
| EP | 2461465 A1 | 6/2012 |
| EP | 2538086 A1 | 12/2012 |
| EP | 2554191 A1 | 2/2013 |
| EP | 2594799 A1 | 5/2013 |
| EP | 2618001 A1 | 7/2013 |
| EP | 2693609 A1 | 2/2014 |
| EP | 2948202 A1 | 12/2015 |
| EP | 2961987 A1 | 1/2016 |
| EP | 3013385 A2 | 5/2016 |
| JP | 58/9535 | 1/1983 |
| JP | 61/293146 | 12/1986 |
| JP | H02-007780 U | 1/1990 |
| JP | H02-033590 U | 3/1990 |
| JP | 04/091396 A | 3/1992 |
| JP | 04/148094 A | 5/1992 |
| JP | 05/021197 U | 3/1993 |
| JP | 06/014538 U | 2/1994 |
| JP | 06/053790 U | 7/1994 |
| JP | 2006/070476 | 9/1994 |
| JP | 2006/245455 | 9/1994 |
| JP | 07/014220 U | 3/1995 |
| JP | 07/042869 U | 8/1995 |
| JP | 07/509156 A | 10/1995 |
| JP | 09/122228 A | 5/1997 |
| JP | 10/331841 A | 12/1998 |
| JP | 11/244377 A | 9/1999 |
| JP | 2001/309628 | 11/2001 |
| JP | 2003/135592 A | 5/2003 |
| JP | 2004166401 | 6/2004 |
| JP | 2004/209240 A | 7/2004 |
| JP | 2004/332566 A | 11/2004 |
| JP | 2004/346925 A | 12/2004 |
| JP | 2005/94955 | 4/2005 |
| JP | 2005/127222 A | 5/2005 |
| JP | 2005/245138 | 9/2005 |
| JP | 2005/270345 A | 10/2005 |
| JP | 2005/270415 A | 10/2005 |
| JP | 2005/287599 A | 10/2005 |
| JP | 2006/167173 A | 6/2006 |
| JP | 2007/002885 A | 1/2007 |
| JP | 2007/043821 | 2/2007 |
| JP | 2007/089972 A | 4/2007 |
| JP | 2007/089974 | 4/2007 |
| JP | 2007/215292 | 8/2007 |
| JP | 2007/247489 | 9/2007 |
| JP | 2008/011611 | 1/2008 |
| JP | 2008/104278 | 5/2008 |
| JP | 2008/132131 | 6/2008 |
| JP | 2008/99453 | 8/2008 |
| JP | 2008/193838 | 8/2008 |
| JP | 2008/297997 A | 12/2008 |
| JP | 2008/301634 | 12/2008 |
| JP | 2006/254619 | 9/2009 |
| JP | 2010/133381 A | 6/2010 |
| JP | 2010/136863 | 6/2010 |
| JP | 2010/203398 | 9/2010 |
| JP | 2010/209691 A | 9/2010 |
| JP | 2011/169166 A | 9/2011 |
| JP | 2012/021413 | 2/2012 |
| JP | 2012/062790 A | 3/2012 |
| JP | 5171953 B2 | 3/2013 |
| JP | 2012021413 A1 | 5/2013 |
| JP | 5572832 B2 | 8/2014 |
| JP | 5656835 B2 | 1/2015 |
| WO | 93/07388 A1 | 4/1993 |
| WO | 94/14226 | 6/1994 |
| WO | 96/31934 | 10/1996 |
| WO | 97/42413 A1 | 11/1997 |
| WO | 00/64509 A1 | 11/2000 |
| WO | 2004/098677 A1 | 11/2004 |
| WO | 2005/011087 A1 | 2/2005 |
| WO | 2005/028000 A1 | 3/2005 |
| WO | 2005/034312 A2 | 4/2005 |
| WO | 2009/157408 A1 | 12/2009 |
| WO | 2010/067682 A1 | 6/2010 |
| WO | 2010/101082 A1 | 9/2010 |
| WO | 2010/101107 A1 | 9/2010 |
| WO | 2011/013483 A1 | 2/2011 |
| WO | 2012/036059 A1 | 3/2012 |
| WO | 2012/040544 A1 | 3/2012 |
| WO | 2012/047550 A1 | 4/2012 |
| WO | 2012/132850 A1 | 10/2012 |
| WO | 2014/113533 A1 | 7/2014 |
| WO | 2014/116676 A1 | 7/2014 |
| WO | 2014/133942 A1 | 9/2014 |
| WO | 2014/179271 A2 | 11/2014 |
| WO | 2016/033131 A1 | 3/2016 |
| WO | 2016/033133 A1 | 3/2016 |
| WO | 2016/130846 A1 | 8/2016 |
| WO | 2016/130944 A1 | 8/2016 |
| WO | 2016/130955 A1 | 8/2016 |

OTHER PUBLICATIONS

European Search report Issued in European Patent Application No. 10/748,702.7, dated Apr. 2, 2013.

Extended European Search Report issued in European Patent Application No. EP 10748677.1, dated Nov 19, 2012.

International Search Report (PCT/ISA/210) dated Jul. 14, 2009, by Japanese Patent Office as the International Searching Authority for International Application No. PCT/JP2009/061318.

(56) References Cited

OTHER PUBLICATIONS

International Search Report and Written Opinion issued in PCT/JP2011/050925, dated Apr. 12,2011.
International Search Report and Written Opinion issued in PCT/JP2011/054134, dated Apr. 12, 2011.
International Search Report and Written Opinion issued in PCT/JP2011/064768, dated Sep. 13, 2011.
International Search Report and Written Opinion issued in PCT/JP2011/070450, dated Dec. 13, 2011.
Kosaka, et al.,"Operating Point Control System for a Continuous Flow Artificial Heart: In Vitro Study," ASAIO Journal 2003, 6 pages.
Supplementary European Search Report issued in European Application No. 09/831,788.6, dated Jan. 7, 2013, 7 pages.
Terumo Heart, Inc., "Handled With Care—Significantly Reduce the Risk of Cell Damage," Terumo brochure, Apr. 2010, 2 pages.
Yamazaki, et al., "Development of a Miniature Intraventricular Axial Flow Blood Pump," ASAIO Journal, 1993, 7 pages.
International Search Report and Written Opinion of PCT/US2014/012448 dated Feb. 19, 2014, 8 pages.
European office action dated Jan. 27, 2016 for EP 10804230.0, all pages.
Extended European Search Report dated Feb. 4, 2016 in European Patent Application No. EP 12764433.4, filed Mar. 12, 2012, all pages.
International Preliminary Report on Patentability dated Jul. 30, 2015 for International Patent Application No. PCT/US2014/011786, dated Jan. 16, 2014, all pages.
International Search Report and Written Opinion of PCT/US2014/012511, dated May 147, 2014, all pages.
International Search Report and Written Opinion of PCT/US2014/017932, dated Jun. 16, 2014, all pages.
International Preliminary Report on Patentability dated Sep. 11, 2015 for International Patent Application No. PCT/US2014/017932, dated Feb. 24, 2014, all pages.
International Search Report and Written Opinion of PCT/US2014/035798, dated Feb. 11, 2016, all pages.
International Search Report and Written Opinion of PCT/US2016/017611, dated May 16, 2016, all pages.
International Search Report and Written Opinion of PCT/US2016/017791, dated May 16, 2016, all pages.
Japanese office action dated Dec. 11, 2015 JP 2013-507344, all pages.
International Search Report and Written Opinion of PCT/US2016/017812, dated Jun. 7, 2016, all pages.
International Search Report and Written Opinion of PCT/US2016/017864, dated Jun. 8, 2016, all pages.
Decision to Grant for JP 2013-507344 dated Jun. 14, 2016, all pages.
Extended European Search Report issued in European Patent Application No. EP 11825062.0, dated Jun. 18, 2015, all pages.
Extended European Search Report issued in European Patent Application No. EP 11806627.3, dated Oct. 8, 2014, all pages.
Extended European Search Report dated Mar. 26, 2015 in European Patent Application No. EP 09770118.9 filed Jun. 22, 2009, all pages.
International Search Report and Written Opinion of PCT/US2014/012502 dated May 9, 2014, all pages.
International Search Report and Written Opinion of PCT/US2014/012511 dated May 14, 2014, all pages.
International Search Report and Written Opinion of PCT/US2014/017932 dated Jun. 16, 2014, all pages.
International Search Report and Written Opinion of PCT/US2014/011786 dated May 5, 2014, all pages.
International Preliminary Report on Patentability dated Aug. 6, 2015 for International Patent Application No. PCT/US2014/012511 filed on Jan. 22, 2014, all pages.
International Preliminary Report on Patentability dated Aug. 6, 2015 for International Patent Application No. PCT/US2014/012502 filed on Jan. 22, 2014, all pages.
International Preliminary Report on Patentability dated Feb. 25, 2016 for International Patent Application No. PCT/US2014/035798 filed on Apr. 29, 2014, all pages.
European office action dated Oct. 31, 2016 for EP 10804230.0, all pages.
Gieras, et al., "Advancements in Electric Machines", Nov. 14, 2008, pp. 43-48.
International Search Report and Written Opinion of PCT/US2016/062284, dated Feb. 24, 2017, all pages.
Sandtner, J., et al., "Electrodynamic Passive Magnetic Bearing with Planar Halbach Arrays", Aug. 6, 2004 (Aug. 6, 2004), retrieved from the internet: <http://www.silphenix.ch/lexington.pdf>, all pages.
Asama, J., et al., "A Compact Highly Efficient and Low Hemolytic Centrifugal Blood Pump With a Magnetically Levitated Impeller", Artificial Organs, vol. 30, No. 3, Mar. 1, 2006 (Mar. 1, 2006), pp. 160-167.
Asama, J., et al.,"A New Design for a Compact Centrifugal Blood Pump with a Magnetically Levitated Rotor", Asaio Jopurnal, vol. 50, No. 6, Nov. 1, 2004 (Nov. 1, 2004), pp. 550-556.
Neethu, S., et al., "Novel design, optimization and realization of axial flux motor for implantable blood pump", Power Electronics, Drives and Energy Systems (PEDES) & 2010 Power Indian, 2010 Joint International Conference on, IEEE, Dec. 20, 2010 (Dec. 20, 2010), pp. 1-6.
European office action dated Jul. 22, 2016 for European Patent Application No. EP 09770118.9, all pages.
European office action dated Sep. 8, 2016 for EP 14741174, all pages.
European Office Action issued in Application No. EP 11825062 dated Jul. 19, 2016, all pages.
Extended European Search Report for EP 14 74 3371 dated Sep. 29, 2016, all pages.
International Search Report and Written Opinion of PCT/US2015/046844, dated Oct. 27, 2015, all pages.
International Search Report and Written Opinion of PCT/US2015/046846, dated Oct. 27, 2015, all pages.

* cited by examiner

FIG.33
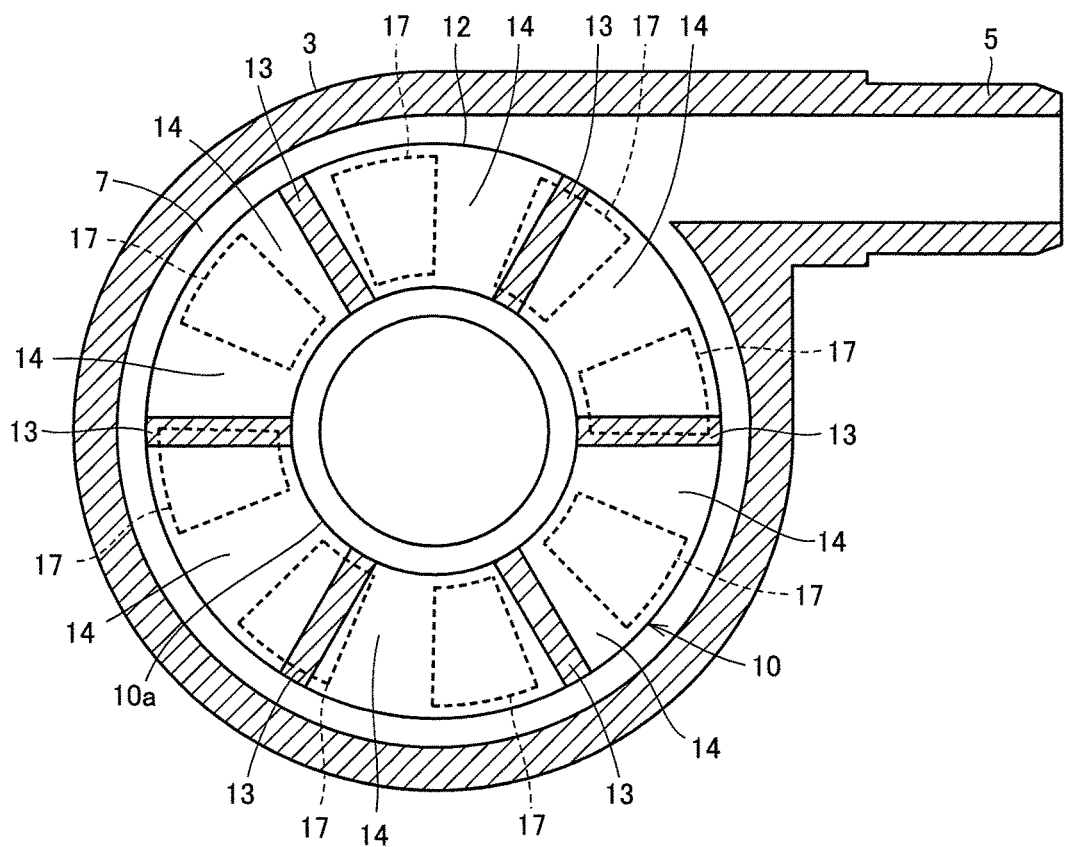
FIG.34
(a) SECOND EMBODIMENT
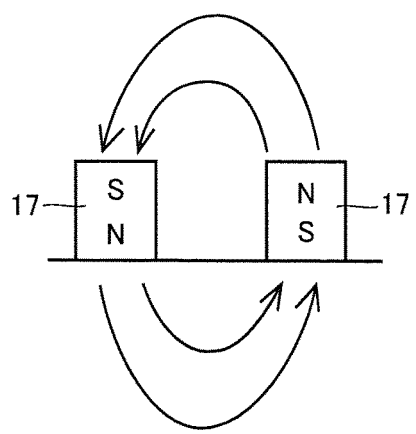
(b) FIRST EMBODIMENT
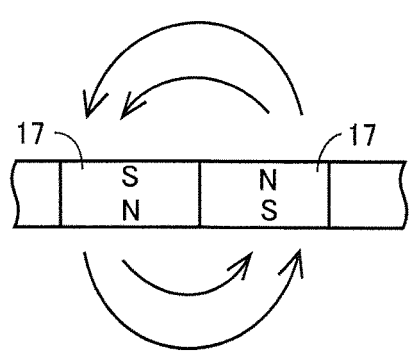

AREA RATIO OF PERMANENT MAGNET 51
TO PERMANENT MAGNET 17

FIG.37
(a)
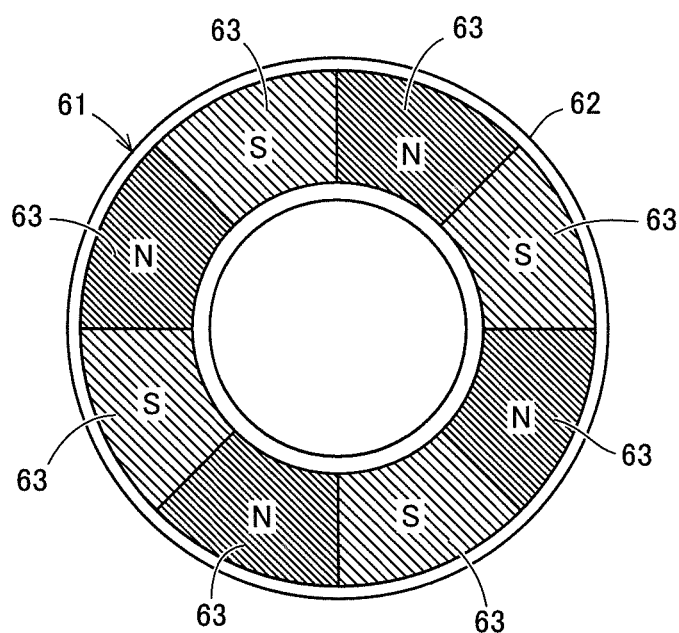
(b)
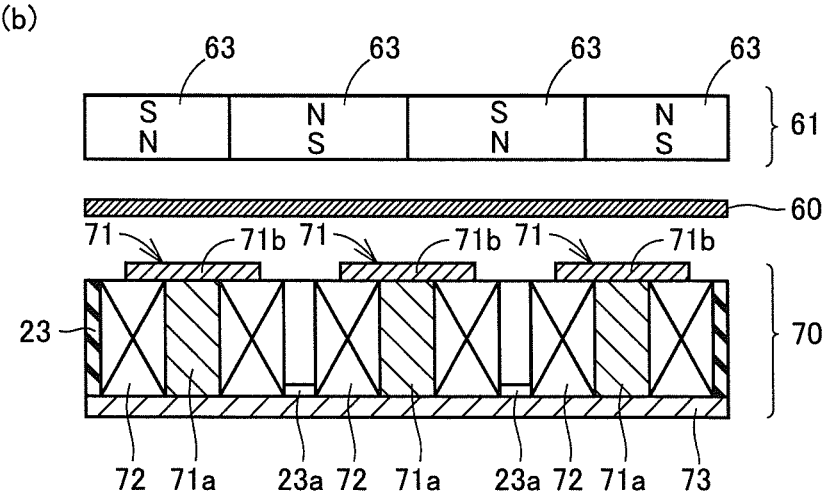

FIG.38
(a)
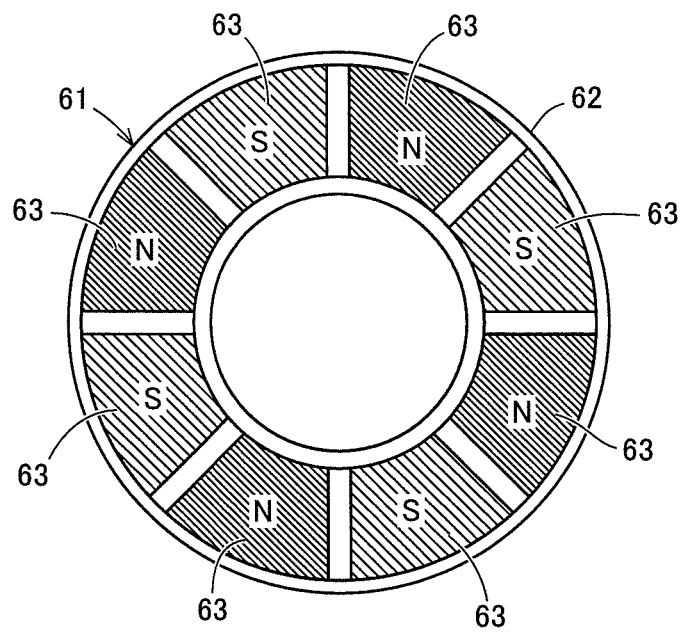
(b)
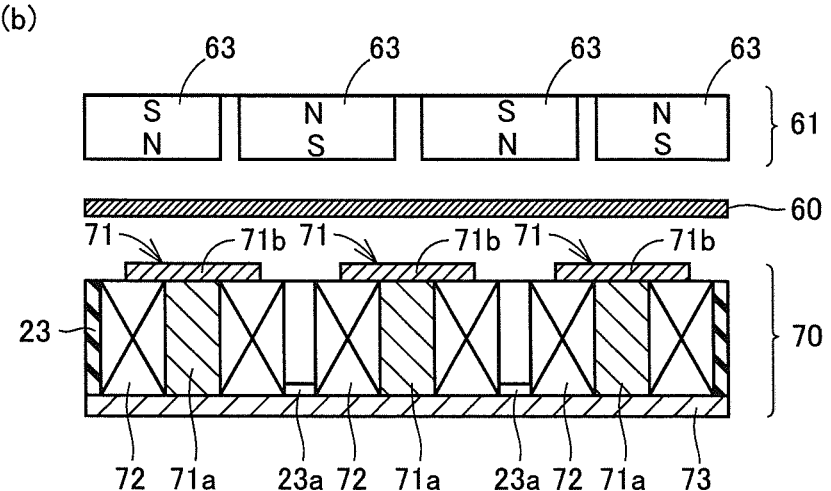

FIG.39
(a)
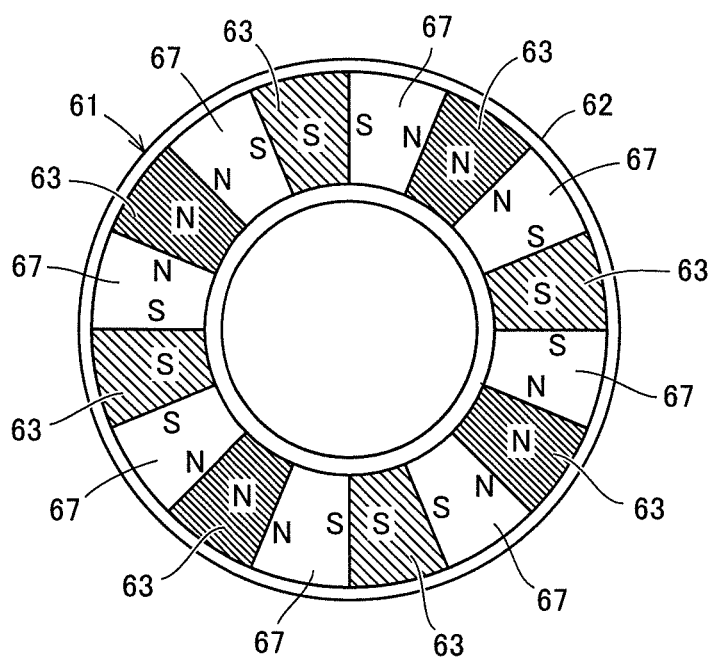
(b)
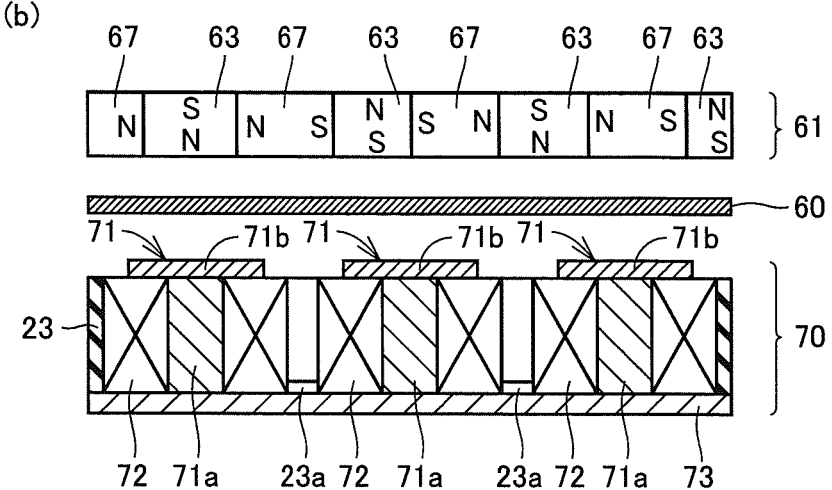

ROTATION DRIVE DEVICE AND CENTRIFUGAL PUMP APPARATUS EMPLOYING SAME

CROSS REFERENCE TO RELATED APPLICATIONS

This application is a continuation of PCT Application No. PCT/JP2012/056244, filed Mar. 12, 2012, based on and claiming priority to Japanese application no. 2011-070286, filed Mar. 28, 2011, both of which are incorporated herein by reference in their entirety.

TECHNICAL FIELD

The present invention relates to rotation drive devices and centrifugal pump apparatuses employing the same, and more particularly to a rotation drive device for transmitting a driving force via a dividing wall and a centrifugal pump apparatus employing the same.

BACKGROUND ART

In recent years, canned motors having a structure including a motor drive chamber and a rotor chamber separated from each other by a dividing wall have been widely used. Such motor is used for a pump for transporting pure water in a semiconductor manufacturing line used in an environment that avoids dust, and a pump for transporting a biological solution, for example. Pumps for transporting a biological solution include a centrifugal blood pump apparatus employing a direct drive motor for directly transmitting torque to an impeller in a blood chamber. This centrifugal blood pump apparatus can eliminate physical contact between the blood chamber and the outside to prevent invasion of bacteria and the like into blood, and is thus used as an artificial heart. Since an artificial heart is driven by electric power from a battery, enhancement of motor efficiency is critical.

A centrifugal blood pump in Japanese Patent Laying-Open No. 2004-209240 (Patent Document 1) includes a housing having first to third chambers partitioned from one another by first and second dividing walls, an impeller rotatably provided in the second chamber (blood chamber), a magnetic element provided in one surface of the impeller, an electromagnet provided in the first chamber to face the one surface of the impeller, a permanent magnet provided in the other surface of the impeller, a rotor and a motor provided in the third chamber, and a permanent magnet provided in the rotor to face the other surface of the impeller. A groove for hydrodynamic bearing is formed in a surface of the second dividing wall facing the other surface of the impeller. Owing to attractive force acting on the one surface of the impeller from the electromagnet, attractive force acting on the other surface of the impeller from the permanent magnet in the rotor, and a hydrodynamic bearing effect of the groove for hydrodynamic bearing, the impeller moves away from an inner wall of the second chamber and rotates without contacting.

A centrifugal blood pump in Japanese Patent Laying-Open No. 2006-167173 (Patent Document 2) includes a housing having first to third chambers partitioned from one another by first and second dividing walls, an impeller rotatably provided in the second chamber (blood chamber), a magnetic element provided in one surface of the impeller, a first permanent magnet provided in the first chamber to face the one surface of the impeller, a second permanent magnet provided in the other surface of the impeller, a rotor and a motor provided in the third chamber, and a third permanent magnet provided in the rotor to face the other surface of the impeller. A first groove for hydrodynamic bearing is formed in a surface of the first dividing wall facing the one surface of the impeller, and a second groove for hydrodynamic bearing is formed in a surface of the second dividing wall facing the other surface of the impeller. Owing to attractive force acting on the one surface of the impeller from the first permanent magnet, attractive force acting on the other surface of the impeller from the third permanent magnet in the rotor, and a hydrodynamic bearing effect of the first and second grooves for hydrodynamic bearing, the impeller moves away from an inner wall of the second chamber and rotates without contacting.

A turbo-type pump in FIGS. 8 and 9 of Japanese Patent Laying-Open No. 4-91396 (Patent Document 3) includes a housing, an impeller rotatably provided in the housing, a first permanent magnet provided in one surface of the impeller, a rotor provided outside the housing, a second permanent magnet provided in the rotor to face the one surface of the impeller, a third permanent magnet provided in the other surface of the impeller, and a magnetic element provided in the housing to face the other surface of the impeller. A first groove for hydrodynamic bearing is formed in the one surface of the impeller, and a second groove for hydrodynamic bearing is formed in the other surface of the impeller. Owing to attractive force acting on the one surface of the impeller from the second permanent magnet in the rotor, attractive force acting on the other surface of the impeller from the magnetic element in the housing, and a hydrodynamic bearing effect of the first and second grooves for hydrodynamic bearing, the impeller moves away from an inner wall of the housing and rotates without contacting.

A clean pump in Japanese Utility Model Laying-Open No. 6-53790 (Patent Document 4) includes a casing, an impeller rotatably provided in the casing, a first permanent magnet provided in one surface of the impeller, a rotor provided outside the casing, a second permanent magnet provided in the rotor to face the one surface of the impeller, a magnetic element provided in the other surface of the impeller, and an electromagnet provided outside the housing to face the other surface of the impeller. A groove for hydrodynamic bearing is formed in the one surface of the impeller. The electromagnet is actuated when a rotation speed of the impeller is lower than a prescribed rotation speed, and power supply to the electromagnet is stopped when the rotation speed of the impeller becomes higher than the prescribed rotation speed. Owing to attractive force acting on the one surface of the impeller from the second permanent magnet in the rotor and a hydrodynamic bearing effect of the groove for hydrodynamic bearing, the impeller moves away from an inner wall of the housing and rotates without contacting.

CITATION LIST

Patent Documents

PTD 1: Japanese Patent Laying-Open No. 2004-209240
PTD 2: Japanese Patent Laying-Open No. 2006-167173
PTD 3: Japanese Patent Laying-Open No. 4-91396
PTD 4: Japanese Utility Model Laying-Open No. 6-53790

SUMMARY OF INVENTION

Technical Problem

Under conditions that require further reduction of the size and thickness of an apparatus, however, it is difficult to secure space for wiring in a drive unit. Particularly, a motor for a small-size pump has a low degree of design flexibility due to dimensional restrictions and so on. In such a motor, soldering between wiring lines in clearance portions that are structurally formed between motor coils results in poor working efficiency, as well as low assembling workability, productivity and reliability.

In view of the above, a main object of the present invention is to provide a small-size rotation drive device of high assembling workability, productivity and reliability, and a centrifugal pump apparatus employing the same.

Solution to Problem

A rotation drive device according to the present invention includes a rotatably provided rotor, and a drive unit for driving the rotor to rotate. The drive unit includes a plurality of first magnetic elements provided to face the rotor, a plurality of coils wound around the plurality of first magnetic elements, respectively, for generating rotating magnetic field, a connector for externally receiving a driving voltage, and a flexible substrate connected to the plurality of coils and the connector. The flexible substrate is provided with a wiring pattern for supplying the driving voltage externally provided via the connector to the plurality of coils.

Preferably, the rotor includes a plurality of first permanent magnets, each first permanent magnet is magnetized in a direction orthogonal to a rotation direction of the rotor, every two adjacent magnetic polarities of the first permanent magnets are different from each other, and the plurality of first magnetic elements are arranged to face the plurality of first permanent magnets.

Preferably, the rotor further includes a plurality of second permanent magnets, the plurality of second permanent magnets are interposed between the plurality of first permanent magnets, respectively, and each second permanent magnet is magnetized in the rotation direction of the rotor. Each second permanent magnet has a first magnetic polarity toward one of two first permanent magnets adjacent thereto having a first magnetic polarity toward the rotor, and each second permanent magnet has a second magnetic polarity toward one of two first permanent magnets adjacent thereto having a second magnetic polarity toward the rotor.

Preferably, the rotor and the drive unit are spaced apart from each other in a direction in which a rotation central axis of the rotor extends, and the plurality of first magnetic elements are aligned in a rotation direction of the rotor.

Preferably, the flexible substrate is formed in the shape of a strip, the flexible substrate is at least partially arranged to surround outer circumferences of the plurality of coils, and the flexible substrate is provided with a plurality of electrodes for connection with the plurality of coils.

Preferably, the flexible substrate is at least partially arranged cylindrically to surround the outer circumferences of the plurality of coils, with a plurality of clearances formed between an inner circumferential surface of the flexible substrate and outer circumferential surfaces of the plurality of coils, and the plurality of electrodes are arranged in a dispersed manner in the flexible substrate so as to be positioned in the plurality of clearances.

Preferably, the flexible substrate in the shape of a strip includes a plurality of bent portions on one side or both sides in a width direction of the flexible substrate, the plurality of bent portions are arranged in a dispersed manner in a length direction of the flexible substrate so as to be positioned in the plurality of clearances, each bent portion being bent into the corresponding clearance, and the plurality of electrodes are formed in the plurality of bent portions.

Preferably, the plurality of electrodes are aligned in a length direction of the flexible substrate, and each electrode is provided in a substantially central portion in a width direction of the flexible substrate.

Preferably, the flexible substrate is at least partially arranged in a corrugated shape along the outer circumferences of the plurality of coils, with a plurality of recesses formed on an outer side of the flexible substrate. The flexible substrate in the shape of a strip includes a plurality of bent portions on one side or both sides in a width direction of the flexible substrate, the plurality of bent portions are arranged in a dispersed manner in a length direction of the flexible substrate so as to be positioned in the plurality of recesses, each bent portion being bent into the corresponding recess, and the plurality of electrodes are arranged in a dispersed manner in the plurality of bent portions.

Preferably, the flexible substrate is at least partially arranged in a corrugated shape along the outer circumferences of the plurality of coils, with a plurality of recesses formed on an outer side of the flexible substrate. The plurality of electrodes are arranged in a dispersed manner in a length direction of the flexible substrate so as to be positioned in the plurality of recesses.

Preferably, the flexible substrate has a length at least 1.25 times the length of an outer circumference of the drive unit.

Preferably, the drive unit further includes a second magnetic element in the shape of a disc, the second magnetic element being provided to face the rotor with the plurality of first magnetic elements interposed therebetween, and being coupled to the plurality of first magnetic elements, and the plurality of coils are arranged on a surface of the second magnetic element along an outer circumference of the second magnetic element.

Preferably, the rotor and the drive unit are spaced apart from each other in a radial direction of the rotor, and the plurality of first magnetic elements are aligned in a rotation direction of the rotor.

Preferably, the flexible substrate has a disc shape or an annular shape, and is arranged on one end face or both end faces of the drive unit.

Preferably, the flexible substrate is formed in the shape of a strip, the flexible substrate is at least partially arranged annularly along the plurality of coils, and the flexible substrate is provided with a plurality of electrodes for connection with the plurality of coils.

Preferably, the drive unit further includes a second magnetic element in a cylindrical shape, the second magnetic element being provided to face the rotor with the plurality of first magnetic elements interposed therebetween, and being coupled to the plurality of first magnetic elements.

Preferably, the rotation drive device includes a housing having first and second chambers partitioned from each other by a dividing wall, in which the rotor is rotatably provided in the first chamber along the dividing wall, and the drive unit is provided in the second chamber for driving the rotor to rotate with the dividing wall interposed therebetween.

A centrifugal pump apparatus according to the present invention includes the rotation drive device described above, in which the rotor is an impeller for delivering fluid by centrifugal force during rotation.

A centrifugal pump apparatus according to the present invention includes a housing having first and second chambers partitioned from each other by a dividing wall, an impeller rotatably provided in the first chamber along the dividing wall, for delivering fluid by centrifugal force during rotation, and a drive unit provided in the second chamber for driving the impeller to rotate with the dividing wall interposed therebetween, and includes a first permanent magnet provided in one surface of the impeller, a second permanent magnet provided in an inner wall of the first chamber facing the one surface of the impeller, for attracting the first permanent magnet, and a plurality of third permanent magnets provided in the other surface of the impeller and attracted by the drive unit. The drive unit includes a plurality of magnetic elements arranged to face the plurality of third permanent magnets, a plurality of coils provided correspondingly to the plurality of magnetic elements respectively and each wound around the corresponding magnetic element, for generating rotating magnetic field, a connector fixed to the housing and externally receiving a driving voltage, and a flexible substrate connected to the plurality of coils and the connector. The flexible substrate is provided with a wiring pattern for supplying the driving voltage externally provided via the connector to the plurality of coils. During rotation of the impeller, first attractive force between the first and second permanent magnets and second attractive force between the plurality of third permanent magnets and the plurality of magnetic elements are balanced with each other in a substantially central portion of a movable range of the impeller in the first chamber. A first groove for hydrodynamic bearing is formed in one surface of the impeller or in the inner wall of the first chamber facing the one surface, and a second groove for hydrodynamic bearing is formed in the other surface of the impeller or in the dividing wall facing the other surface.

Preferably, the fluid is blood, and the centrifugal pump apparatus is used for circulating the blood.

Advantageous Effects of Invention

As described above, according to the present invention, the flexible substrate provided with the wiring pattern for supplying the driving voltage to the plurality of coils is connected to the plurality of coils and the connector, thereby improving the assembling workability, security and reliability of the apparatus, and reducing the size of the apparatus. In addition, the rotor can be rotated at high speed while the small dimensions of the apparatus are maintained, to increase force in activating the rotor to rotate. Moreover, large torque can be generated for driving the rotor to rotate. Furthermore, energy efficiency can be enhanced when driving the rotor to rotate.

BRIEF DESCRIPTION OF DRAWINGS

FIG. 33 is a cross-sectional view showing a substantial part of a pump unit of a centrifugal blood pump apparatus according to a second embodiment of the present invention.

FIG. 34 illustrates the effect of the second embodiment.

FIG. 37 shows the structure of an axial gap type motor according to a third embodiment of the present invention.

FIG. 38 shows a modification of the third embodiment.

FIG. 39 shows another modification of the third embodiment.

DESCRIPTION OF EMBODIMENTS

[First Embodiment]

Figure 1:
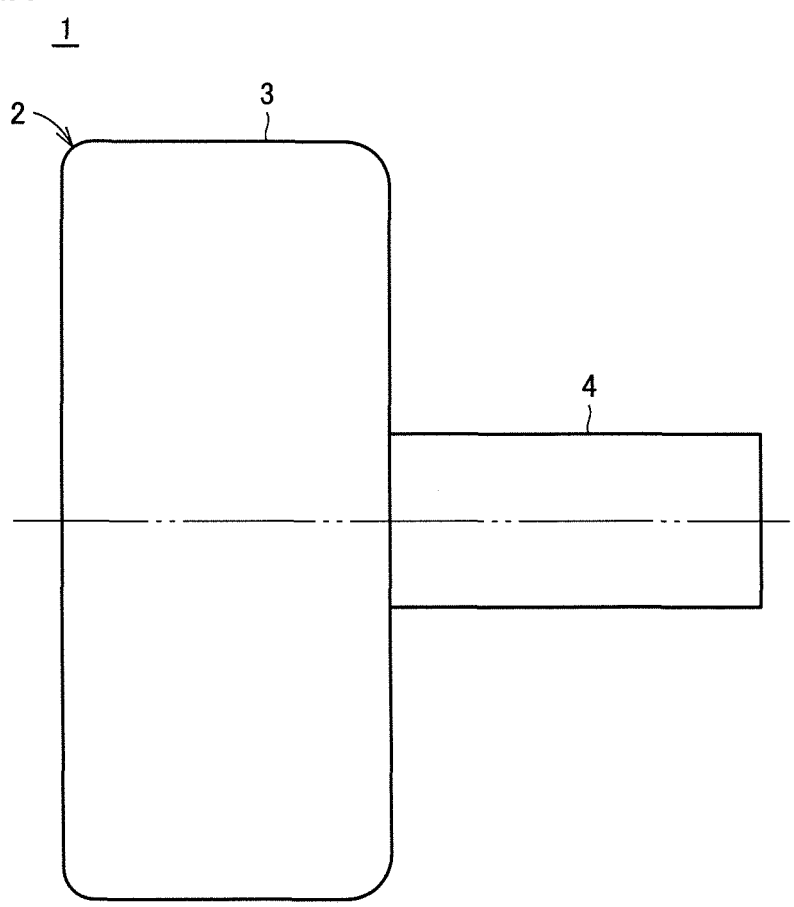
FIG. 1 is a front view showing the appearance of a pump unit of a centrifugal blood pump apparatus according to a first embodiment of the present invention.
Figure 2:
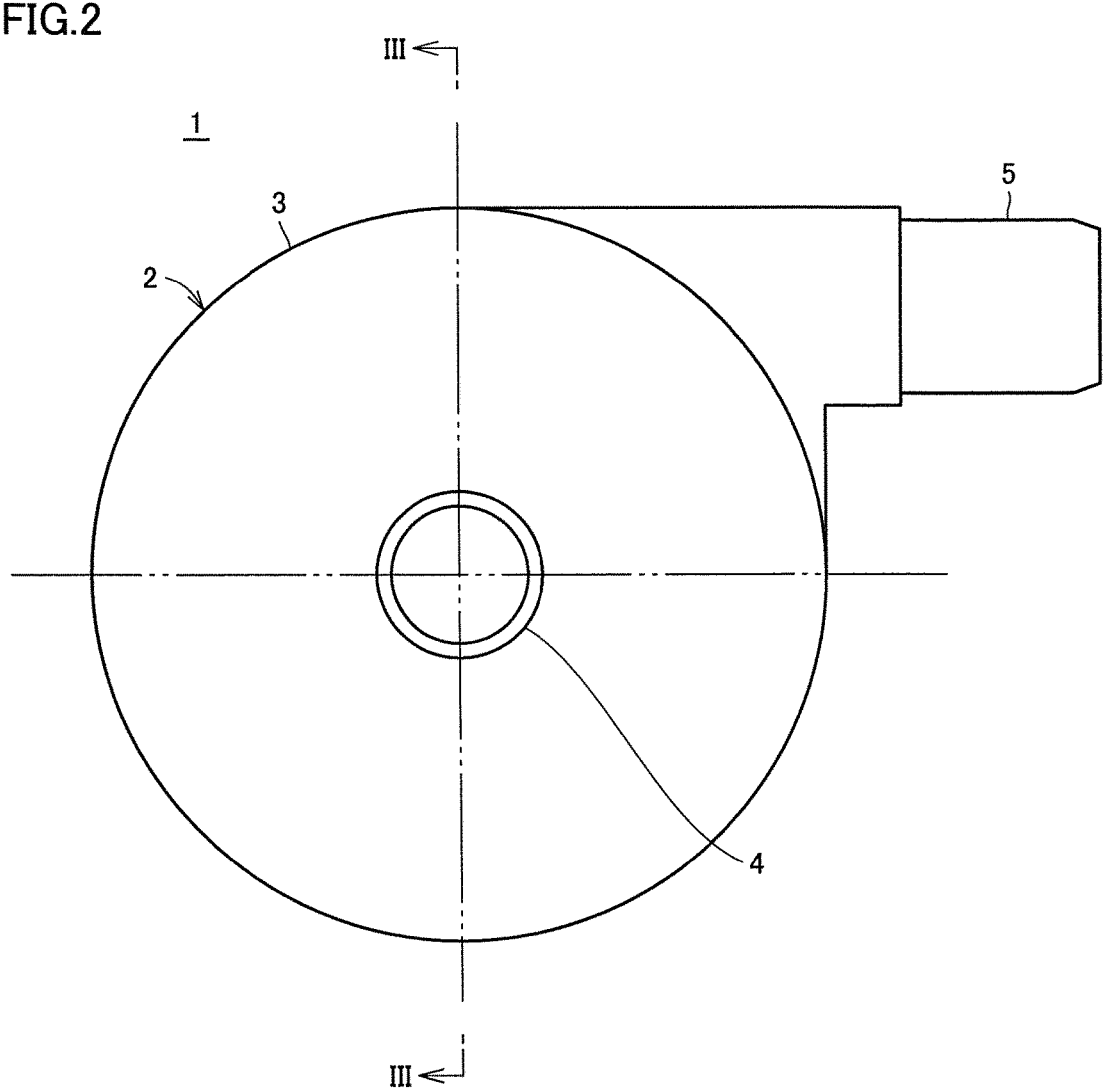
FIG. 2 is a side view of the pump unit shown in FIG. 1.

As shown in FIGS. 1 to 7, a pump unit 1 of a centrifugal blood pump apparatus according to a first embodiment of the present invention includes a housing 2 made of a nonmagnetic material. Housing 2 includes a cylindrical body portion 3, a cylindrical blood inlet port 4 provided to stand at a center of one end surface of body portion 3, and a cylindrical blood outlet port 5 provided on an outer circumferential surface of body portion 3. Blood outlet port 5 extends in a tangential direction of the outer circumferential surface of body portion 3.

Figure 3:
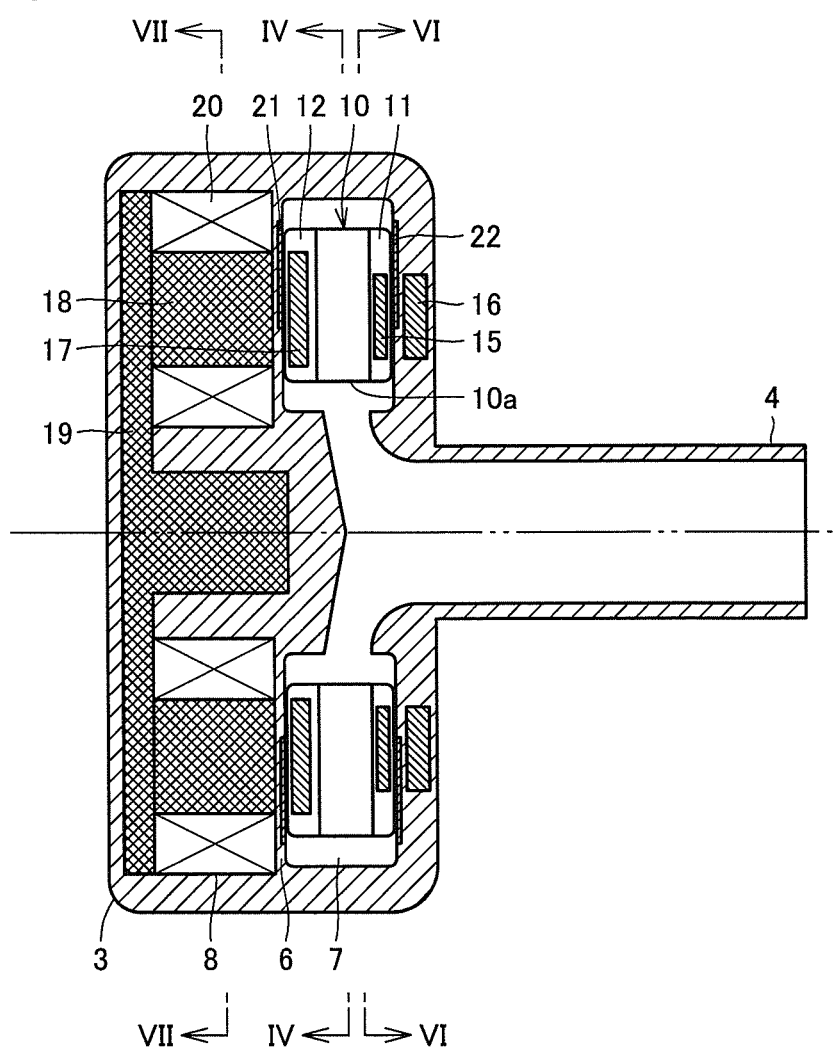
FIG. 3 is a cross-sectional view along the line III-III in FIG. 2.
Figure 4:
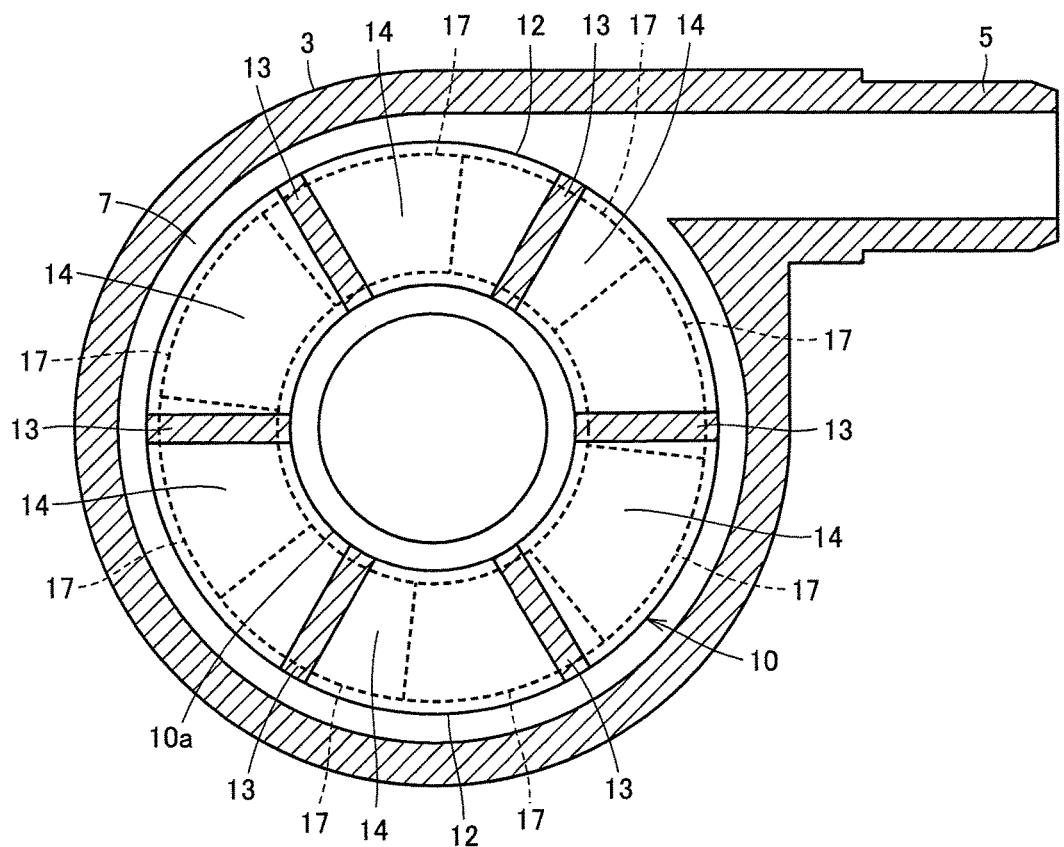
FIG. 4 is a cross-sectional view along the line IV-IV in FIG. 3.

In housing 2, as shown in FIG. 3, a blood chamber 7 and a motor chamber 8 partitioned from each other by a dividing wall 6 are provided. In blood chamber 7, as shown in FIGS. 3 and 4, a disc-shaped impeller 10 having a through hole 10a in a center thereof is rotatably provided. Impeller 10 includes two shrouds 11, 12 in a doughnut plate shape, and a plurality of (e.g., six) vanes 13 formed between two shrouds 11 and 12. Shroud 11 is arranged on the blood inlet port 4 side, and shroud 12 is arranged on the dividing wall 6 side. Shrouds 11, 12 and vanes 13 are made of a nonmagnetic material.

A plurality of (six in this case) blood passages 14 partitioned from one another by the plurality of vanes 13 are formed between two shrouds 11 and 12. As shown in FIG. 4, blood passage 14 is in communication with through hole 10a at the center of impeller 10, and extends with through hole 10a of impeller 10 as a starting point to an outer circumference such that blood passage 14 gradually increases in width. In other words, vane 13 is formed between two adjacent blood passages 14. In the first embodiment, the plurality of vanes 13 are provided at regular angular intervals, and they have the same shape. Thus, the plurality of blood passages 14 are provided at regular angular intervals, and they have the same shape.

When impeller 10 is driven to rotate, blood that has flowed in through blood inlet port 4 is delivered by centrifugal force from through hole 10a to an outer circumferential portion of impeller 10 via blood passages 14, and flows out through blood outlet port 5.

A permanent magnet 15 is embedded in shroud 11, and a permanent magnet 16 for attracting permanent magnet 15 is embedded in an inner wall of blood chamber 7 facing shroud 11. Permanent magnets 15, 16 are provided to attract (in other words, bias) impeller 10 to the side opposite to motor chamber 8, that is, toward blood inlet port 4.

Instead of providing permanent magnets 15, 16 in shroud 11 and in the inner wall of blood chamber 7, respectively, a permanent magnet may be provided in one of shroud 11 and the inner wall of blood chamber 7, and a magnetic element may be provided in the other. Alternatively, shroud 11 itself may be formed of permanent magnet 15 or a magnetic element. Either a soft magnetic element or a hard magnetic element may be used as the magnetic element.

A single permanent magnet 16 or a plurality of permanent magnets 16 may be provided. If a single permanent magnet 16 is provided, permanent magnet 16 is formed in a ring shape. If a plurality of permanent magnets 16 are provided, the plurality of permanent magnets 16 are arranged at regular angular intervals along the same circle. As with permanent magnet 16, a single permanent magnet 15 or a plurality of permanent magnets 15 may be provided.

As shown in FIG. 4, a plurality of (e.g., eight) permanent magnets 17 are embedded in shroud 12. The plurality of permanent magnets 17 are arranged at regular angular intervals along the same circle such that adjacent magnetic polarities thereof are different from each other. In other words, permanent magnet 17 having the N-pole toward motor chamber 8 and permanent magnet 17 having the S-pole toward motor chamber 8 are alternately arranged at regular angular intervals along the same circle.

Figure 7:
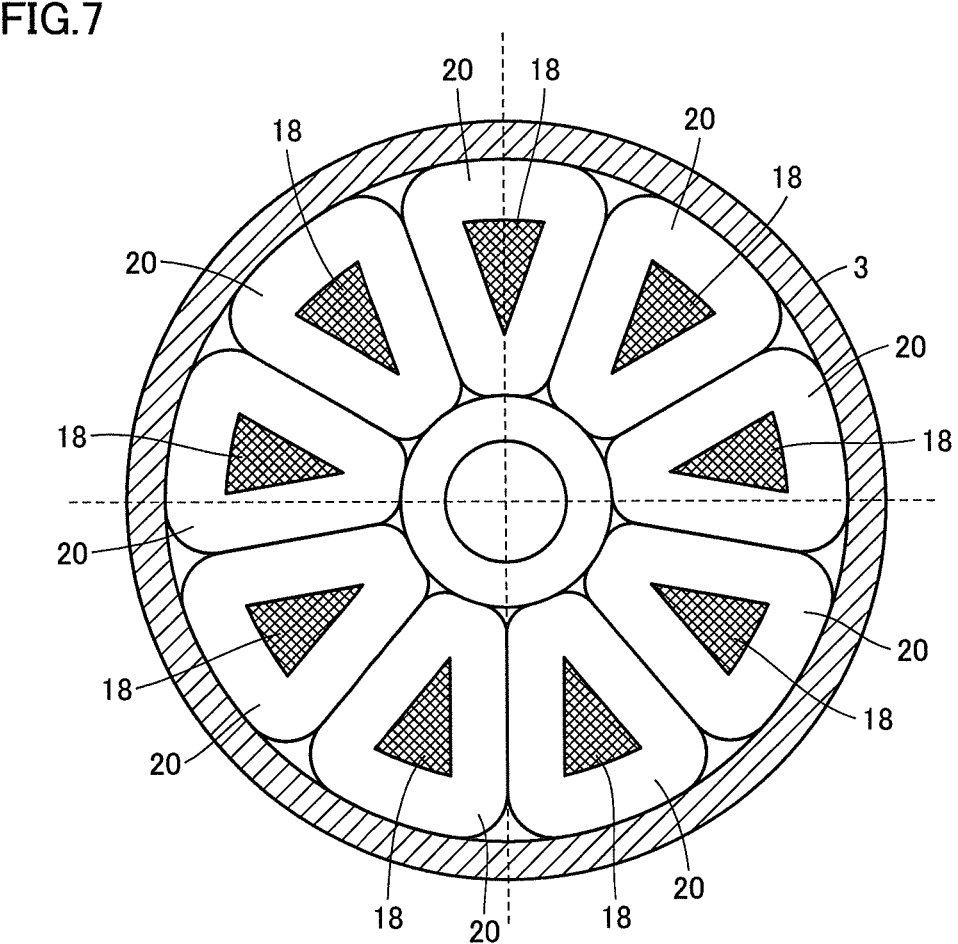
FIG. 7 is a cross-sectional view along the line VII-VII in FIG. 3.

As shown in FIG. 7, a plurality of (e.g., nine) magnetic elements 18 are provided in motor chamber 8. The plurality of magnetic elements 18 are arranged at regular angular intervals along the same circle to face the plurality of permanent magnets 17 in impeller 10. A base end of each of the plurality of magnetic elements 18 is joined to one disc-shaped yoke 19. A coil 20 is wound around each magnetic element 18.

In addition, space for winding coil 20 is equally secured around the plurality of magnetic elements 18, and surfaces facing each other of every two adjacent magnetic elements 18 are provided substantially in parallel to each other. Thus, a large space for coils 20 can be secured to increase the number of turns of coils 20. As a result, large torque for driving impeller 10 to rotate can be generated. Further, copper loss that occurs in coils 20 can be reduced, thereby enhancing energy efficiency when driving impeller 10 to rotate. The plurality of magnetic elements 18 may be formed in a cylindrical shape. In this case, a circumferential length of coils 20 can be minimized to reduce copper loss that occurs in coils 20, thereby enhancing energy efficiency when driving impeller 10 to rotate.

An outline surface surrounding the plurality of magnetic elements 18 (circle surrounding the outer circumferences of the plurality of magnetic elements 18 in FIG. 7) may correspond to an outline surface surrounding the plurality of permanent magnets 17 (circle surrounding the outer circumferences of the plurality of magnetic elements 18 in FIG. 4), or the outline surface surrounding the plurality of magnetic elements 18 may be larger than the outline surface surrounding the plurality of permanent magnets 17. Further, it is preferable that magnetic element 18 be designed to be not magnetically saturated at maximum rating of pump 1 (condition where torque for driving impeller 10 to rotate becomes maximum).

Figure 8:
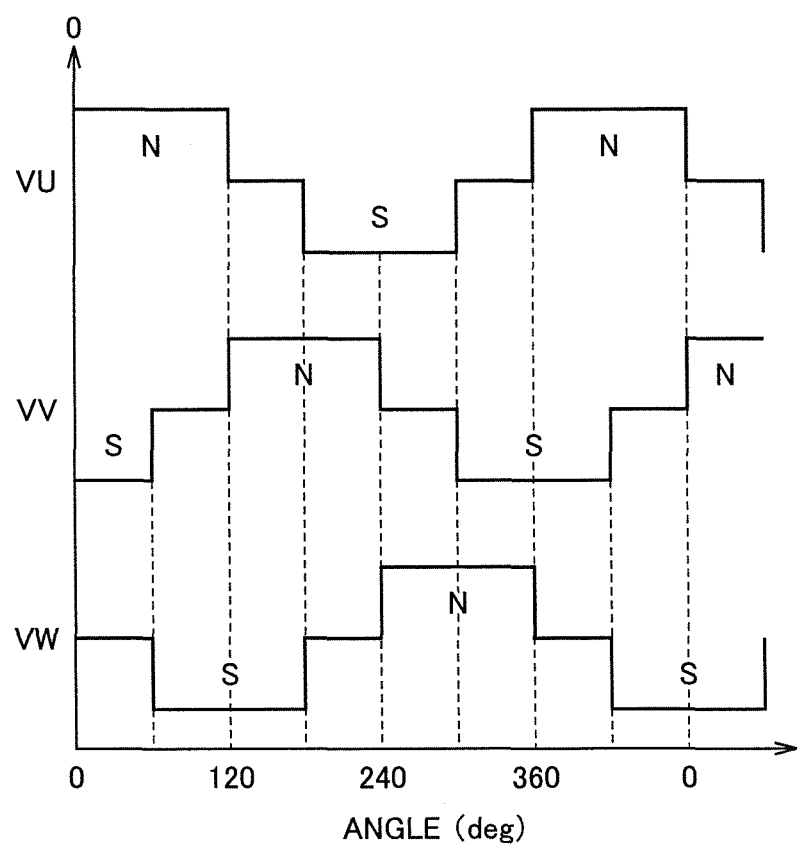
FIG. 8 is a time chart illustrating driving voltages applied to a plurality of coils shown in FIG. 7.

Voltages are applied to nine coils 20 in a power distribution system shifted by 120 degrees, for example. That is, nine coils 20 are divided into groups each including three coils. Voltages VU, VV, VW as shown in FIG. 8 are applied to first to third coils 20 of each group, respectively. To first coil 20, a positive voltage is applied during a period of 0 to 120 degrees, 0 V is applied during a period of 120 to 180 degrees, a negative voltage is applied during a period of 180 to 300 degrees, and 0 V is applied during a period of 300 to 360 degrees. Accordingly, a tip surface of magnetic element 18 having first coil 20 wound therearound (end surface on the impeller 10 side) becomes the N-pole during the period of 0 to 120 degrees, and becomes the S-pole during the period of 180 to 300 degrees. Voltage VV is delayed in phase from voltage VU by 120 degrees, and voltage VW is delayed in phase from voltage VV by 120 degrees. Thus, rotating magnetic field can be formed by applying voltages VU, VV, VW to first to third coils 20, respectively, so that impeller 10 can be rotated by attractive force and repulsion force between the plurality of magnetic elements 18 and the plurality of permanent magnets 17 in impeller 10.

Figure 9:
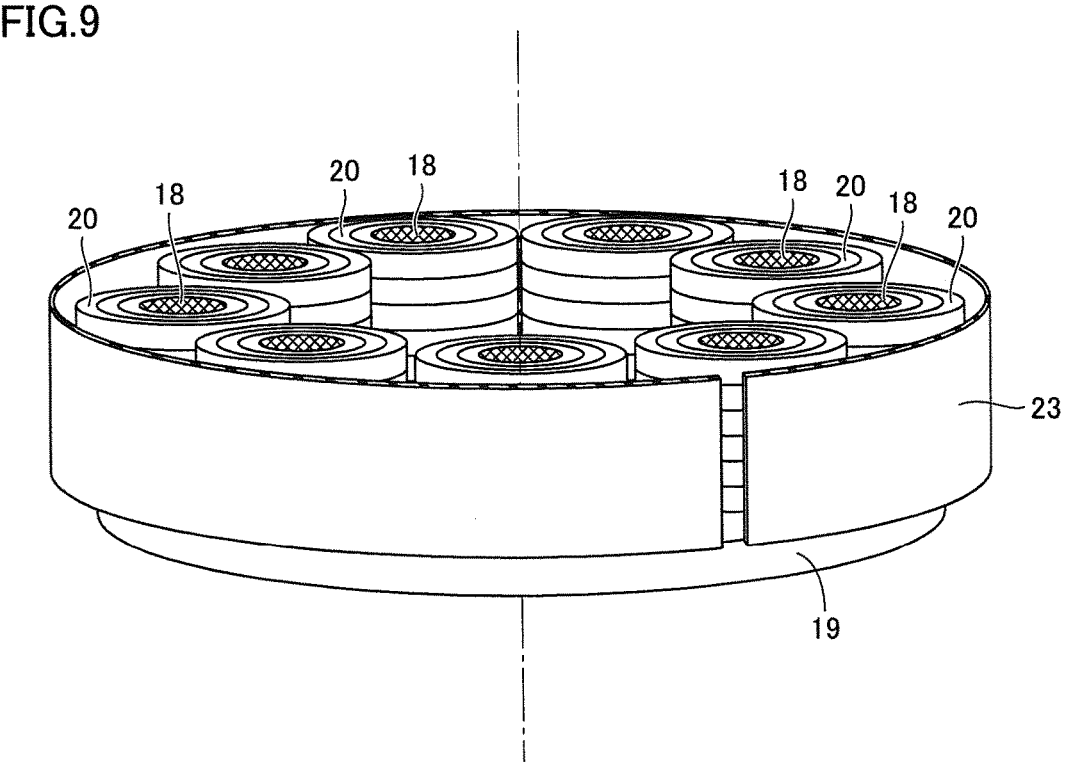
FIG. 9 shows the arrangement of a flexible substrate for supplying the driving voltages to the plurality of coils shown in FIG. 7.

A method of supplying driving voltages VU, VV, VW to nine coils 20 is described. In the first embodiment, as shown in FIG. 9, nine coils 20 are arranged on a surface of yoke 19 along the outer circumference of yoke 19. Each coil 20 is cylindrically wound. A strip-shaped flexible substrate 23 is provided to surround the outer circumferences of nine coils 20, and is connected to nine coils 20. Driving voltages VU, VU, VW are supplied to nine coils 20 via a wiring pattern formed on flexible substrate 23. Thus, assembling workability is improved as compared to an example where each coil 20 is directly connected to a power supply line from a controller (see FIG. 15) by soldering or the like.

Figure 10:
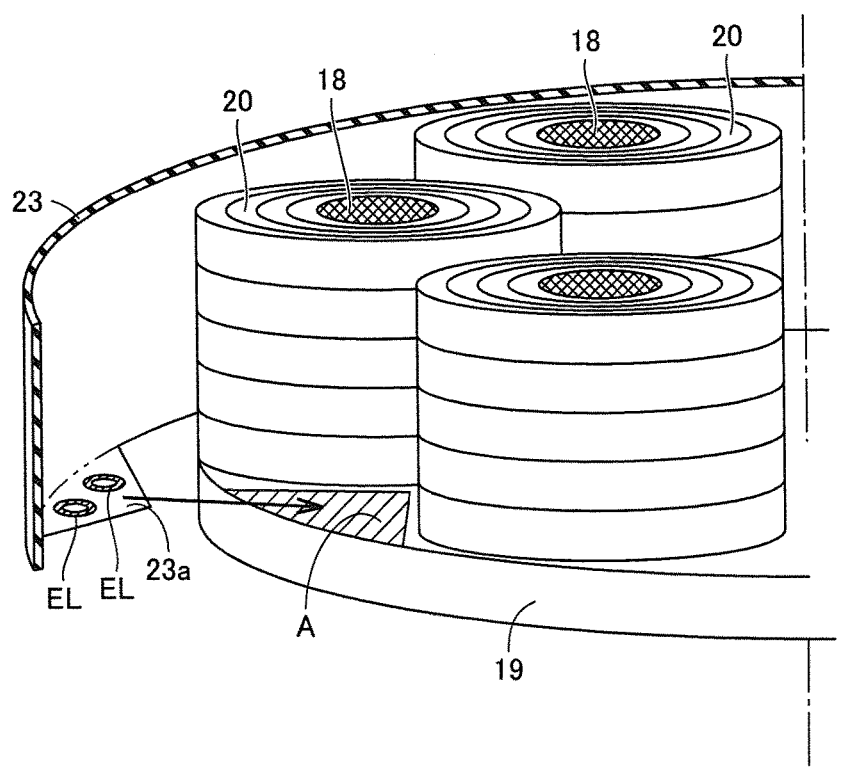
FIG. 10 shows a bent portion and electrodes of the flexible substrate shown in FIG. 9.

As shown in FIG. 10, nine clearances in the form of a triangular prism are formed between an inner circumferential surface of cylindrically arranged flexible substrate 23 and outer circumferential surfaces of nine cylindrical coils 20. In other words, nine areas A in a substantially triangular shape appear in gaps between the circular outer circumference of the surface of yoke 19 and nine coils 20. At a lower end of strip-shaped flexible substrate 23, nine bent portions 23a in a triangular shape are formed correspondingly to nine areas A, respectively. Each bent portion 23a is bent inward substantially perpendicularly to the inner circumferential surface of cylindrically curved flexible substrate 23. A surface of each bent portion 23a is provided with two electrodes EL. Flexible substrate 23 is arranged around nine coils 20 in such a manner that nine bent portions 23a are arranged in nine areas A, respectively. Each coil 20 has two terminals soldered to two electrodes adjacent to this coil 20, respectively. This allows for efficient use of space and size reduction of the apparatus. To provide insulation, the soldered portions may be potted with resin or the like.

Figure 11:
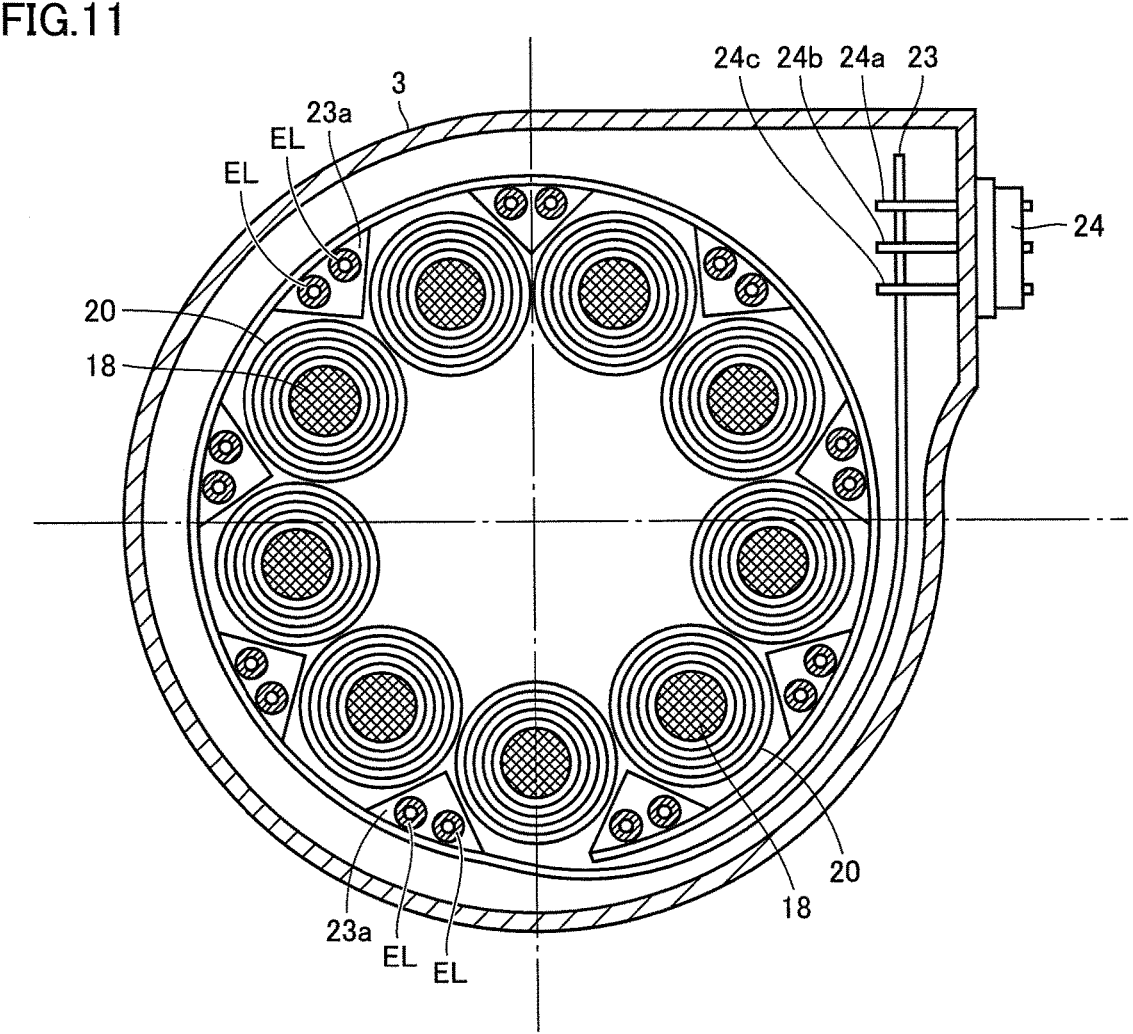
FIG. 11 is a cross-sectional view showing a connector for supplying the driving voltages to the flexible substrate shown in FIGS. 8 and 9.

As shown in FIG. 11, a connector 24 is fixed to body portion 3 of housing 2. Connector 24 includes three pins 24a to 24c penetrating a wall of motor chamber 8. Three-phase driving voltages VU, VV, VW are externally supplied to three pins 24a to 24c. Three pins 24a to 24c are connected to nine coils 20 by the wiring pattern formed on flexible substrate 23. Thus, space for radial wiring can be minimized.

Since it is necessary to connect flexible substrate 23 to all of nine coils 20, and further to connect an end portion of flexible substrate 23 to connector 24, the length of flexible substrate 23 is desirably at least 1.25 times its length that surrounds the outer circumferences of nine coils 20 once. Accordingly, stress applied to flexible substrate 23 can be reduced when fixing a drive unit to housing 2 or when connecting connector 24 fixed to housing 2 to flexible substrate 23, thus increasing reliability.

Figure 12:
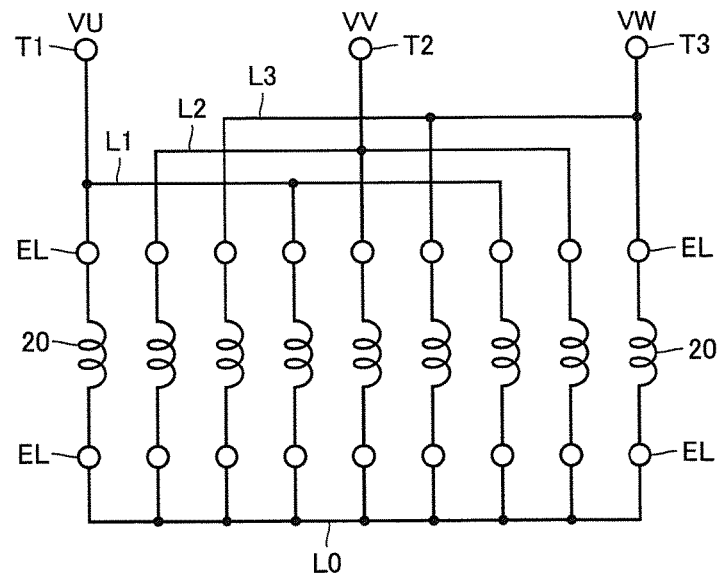
FIG. 12 is a circuit diagram schematically showing a wiring pattern formed on the flexible substrate shown in FIG. 11.

FIG. 12 schematically shows the wiring pattern formed on flexible substrate 23. In FIG. 12, each coil 23 has two terminals connected to two electrodes EL adjacent to this coil 23, respectively. A surface of flexible substrate 23 is provided with four wiring patterns L0 to L3 and three power supply terminals T1 to T3. Nine electrodes EL connected to one terminals of nine coils 20 are connected together by wiring pattern L0. Wiring pattern L0 serves as a neutral point of nine coils 20.

Nine coils 20 are divided into groups each including three coils. Each of the three groups includes first to third coils 20. Three electrodes EL connected to the other terminals of first coils 20 of the three groups are connected together by wiring pattern L1, and are connected to power supply terminal T1. Power supply terminal T1 is connected to pin 24a of connector 24, pin 24a being connected to a U-phase power supply line from the controller (see FIG. 15). The controller supplies driving voltage VU to each first coil 20 via the U-phase power supply line and wiring pattern L1.

Three electrodes EL connected to the other terminals of second coils 20 of the three groups are connected together by wiring pattern L2, and are connected to power supply terminal T2. Power supply terminal T2 is connected to pin 24b of connector 24, pin 24b being connected to a V-phase power supply line from the controller (see FIG. 15). The controller supplies driving voltage VV to each second coil 20 via the V-phase power supply line and wiring pattern L2.

Three electrodes EL connected to the other terminals of third coils 20 of the three groups are connected together by wiring pattern L3, and are connected to power supply terminal T3. Power supply terminal T3 is connected to pin 24c of connector 24, pin 24c being connected to a W-phase power supply line from the controller (see FIG. 15). The controller supplies voltage VW to each third coil 20 via the W-phase power supply line and wiring pattern L3. Flexible substrate 23 is formed of a polyimide film and a metal layer, for example. Electrodes EL, wiring patterns L0 to L3, and power supply terminals T1 to T3 are formed of metal layers.

Referring back to FIG. 3, when impeller 10 is rotating at a rated rotation speed, attractive force between permanent magnets 15 and 16 and attractive force between the plurality of permanent magnets 17 and the plurality of magnetic elements 18 are set to be balanced with each other substantially around a center of a movable range of impeller 10 in blood chamber 7. Thus, force acting on impeller 10 due to the attractive force is very small throughout the movable range of impeller 10. Consequently, frictional resistance during relative slide between impeller 10 and housing 2 which occurs when impeller 10 is activated to rotate can be reduced. In addition, a surface of impeller 10 and a surface of an inner wall of housing 2 are not damaged (no projections and recesses in the surfaces) during the relative slide, and moreover, impeller 10 is readily levitated from housing 2 even when hydrodynamic force is small during low-speed rotation, to enter a non-contacting state. Accordingly, occurrence of hemolysis/thrombus due to the relative slide between impeller 10 and housing 2, or occurrence of thrombus due to small damage (projections and recesses) to the surfaces which occurs during the relative slide is avoided.

A plurality of grooves for hydrodynamic bearing 21 are formed in a surface of dividing wall 6 facing shroud 12 of impeller 10, and a plurality of grooves for hydrodynamic bearing 22 are formed in the inner wall of blood chamber 7 facing shroud 11. When a rotation speed of impeller 10 becomes higher than a prescribed rotation speed, a hydrodynamic bearing effect is produced between each of grooves for hydrodynamic bearing 21, 22 and impeller 10. As a result, drag is generated on impeller 10 from each of grooves for hydrodynamic bearing 21, 22, causing impeller 10 to rotate without contacting in blood chamber 7.

Figure 5:
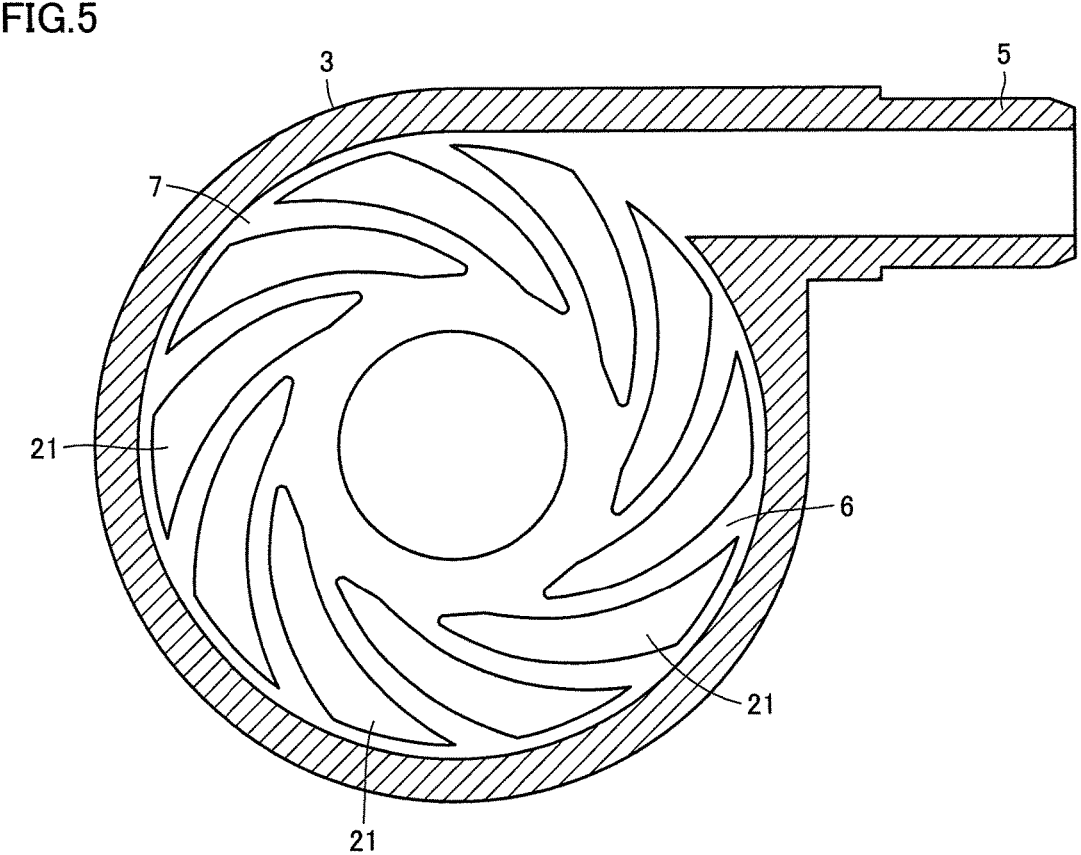
FIG. 5 is a cross-sectional view showing a state where an impeller has been removed from the cross-sectional view along the line IV-IV in FIG. 3.

Specifically, as shown in FIG. 5, the plurality of grooves for hydrodynamic bearing 21 are formed with a size corresponding to shroud 12 of impeller 10. Each groove for hydrodynamic bearing 21 has one end on an edge (circumference) of a circular portion slightly distant from a center of dividing wall 6, and extends spirally (in other words, in a curved manner) toward a portion near an outer edge of dividing wall 6 such that groove for hydrodynamic bearing 21 gradually increases in width. The plurality of grooves for hydrodynamic bearing 21 have substantially the same shape, and they are arranged at substantially regular intervals. Groove for hydrodynamic bearing 21 is a concave portion, and it preferably has a depth of about 0.005 to 0.4 mm. It is preferable that about 6 to 36 grooves for hydrodynamic bearing 21 be provided.

In FIG. 5, ten grooves for hydrodynamic bearing 21 are equiangularly arranged with respect to the central axis of impeller 10. Since grooves for hydrodynamic bearing 21 have a so-called inward spiral groove shape, clockwise rotation of impeller 10 causes increase in fluid pressure from an outer diameter portion toward an inner diameter portion of grooves for hydrodynamic bearing 21. As a result, repulsion force is generated between impeller 10 and dividing wall 6 and it acts as hydrodynamic force.

Instead of providing grooves for hydrodynamic bearing 21 in dividing wall 6, grooves for hydrodynamic bearing 21 may be provided in a surface of shroud 12 of impeller 10.

In this manner, owing to the hydrodynamic bearing effect produced between impeller 10 and the plurality of grooves for hydrodynamic bearing 21, impeller 10 moves away from dividing wall 6 and rotates without contacting. Accordingly, a blood flow path is secured between impeller 10 and dividing wall 6, thus preventing occurrence of blood accumulation therebetween and the resultant thrombus. Further, in a normal state, grooves for hydrodynamic bearing 21 perform a stirring function between impeller 10 and dividing wall 6, thus preventing occurrence of partial blood accumulation therebetween.

It is preferable that a corner portion of each of grooves for hydrodynamic bearing 21 be rounded to have R of at least 0.05 mm. As a result, occurrence of hemolysis can further be reduced.

Figure 6:
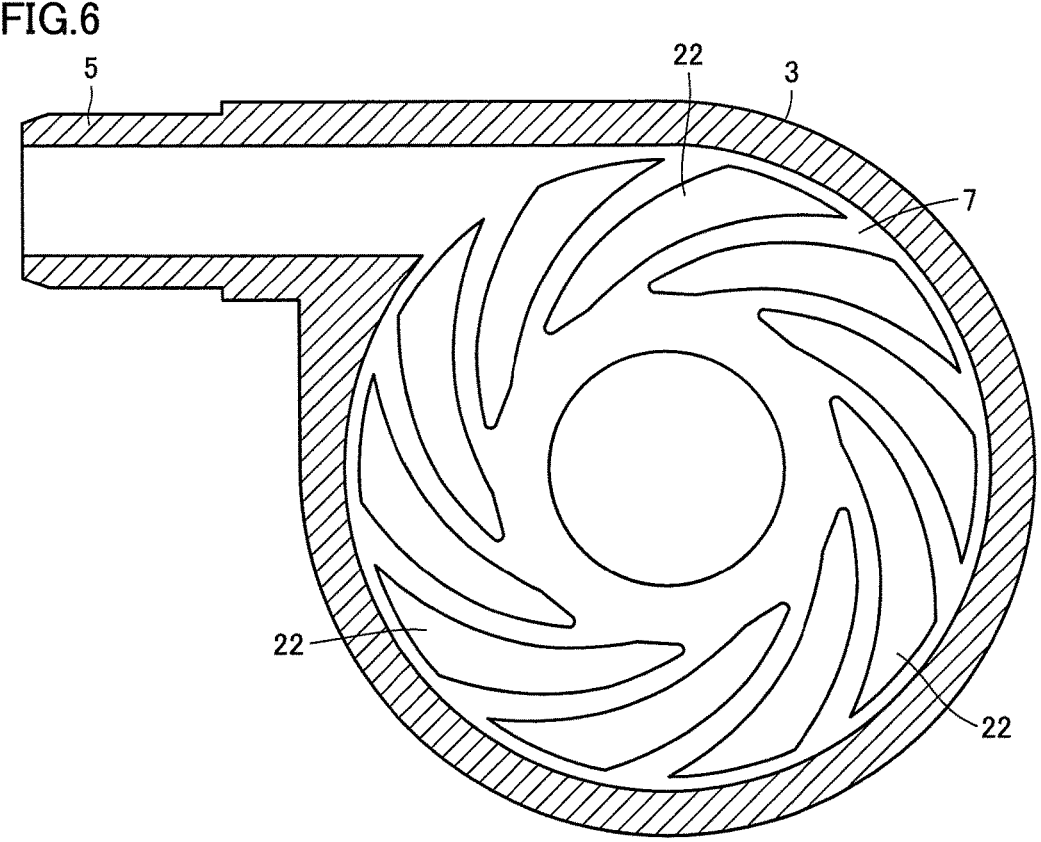
FIG. 6 is a cross-sectional view showing the state where the impeller has been removed from a cross-sectional view along the line VI-VI in FIG. 3.

As with the plurality of grooves for hydrodynamic bearing 21, as shown in FIG. 6, the plurality of grooves for hydrodynamic bearing 22 are formed with a size corresponding to shroud 11 of impeller 10. Each groove for hydrodynamic bearing 22 has one end on an edge (circumference) of a circular portion slightly distant from a center of the inner wall of blood chamber 7, and extends spirally (in other words, in a curved manner) toward a portion near an outer edge of the inner wall of blood chamber 7 such that groove for hydrodynamic bearing 22 gradually increases in width. The plurality of grooves for hydrodynamic bearing 22 have substantially the same shape, and they are arranged at substantially regular intervals. Groove for hydrodynamic bearing 22 is a concave portion, and it preferably has a depth of about 0.005 to 0.4 mm. It is preferable that about 6 to 36 grooves for hydrodynamic bearing 22 be provided. In FIG. 6, ten grooves for hydrodynamic bearing 22 are equiangularly arranged with respect to the central axis of impeller 10.

Instead of providing grooves for hydrodynamic bearing 22 in the inner wall of blood chamber 7, grooves for hydrodynamic bearing 22 may be provided in a surface of shroud 11 of impeller 10. It is preferable that a corner portion of each of grooves for hydrodynamic bearing 22 be rounded to have R of at least 0.05 mm. As a result, occurrence of hemolysis can further be reduced.

In this manner, owing to the hydrodynamic bearing effect produced between impeller 10 and the plurality of grooves for hydrodynamic bearing 22, impeller 10 moves away from the inner wall of blood chamber 7 and rotates without contacting. In addition, when pump unit 1 is subjected to external impact or when the hydrodynamic force generated by grooves for hydrodynamic bearing 21 becomes excessive, impeller 10 can be prevented from being in close contact with the inner wall of blood chamber 7. The hydrodynamic force generated by grooves for hydrodynamic bearing 21 may be different from the hydrodynamic force generated by grooves for hydrodynamic bearing 22.

It is preferable that impeller 10 rotate in a state where a gap between shroud 12 of impeller 10 and dividing wall 6 is substantially equal to a gap between shroud 11 of impeller 10 and the inner wall of blood chamber 7. If one of the gaps becomes narrower due to serious disturbance such as fluid force acting on impeller 10, it is preferable that grooves for hydrodynamic bearing 21 and 22 have different shapes so that the hydrodynamic force generated by the grooves for hydrodynamic bearing on the narrower side becomes higher than the hydrodynamic force generated by the other grooves for hydrodynamic bearing to make the gaps substantially equal to each other.

While each of grooves for hydrodynamic bearing 21, 22 has the inward spiral groove shape in FIGS. 5 and 6, grooves for hydrodynamic bearing 21, 22 having another shape may be used. Nevertheless, for blood circulation, it is preferable to employ grooves for hydrodynamic bearing 21, 22 having the inward spiral groove shape that allows a smooth flow of blood.

Figure 13:
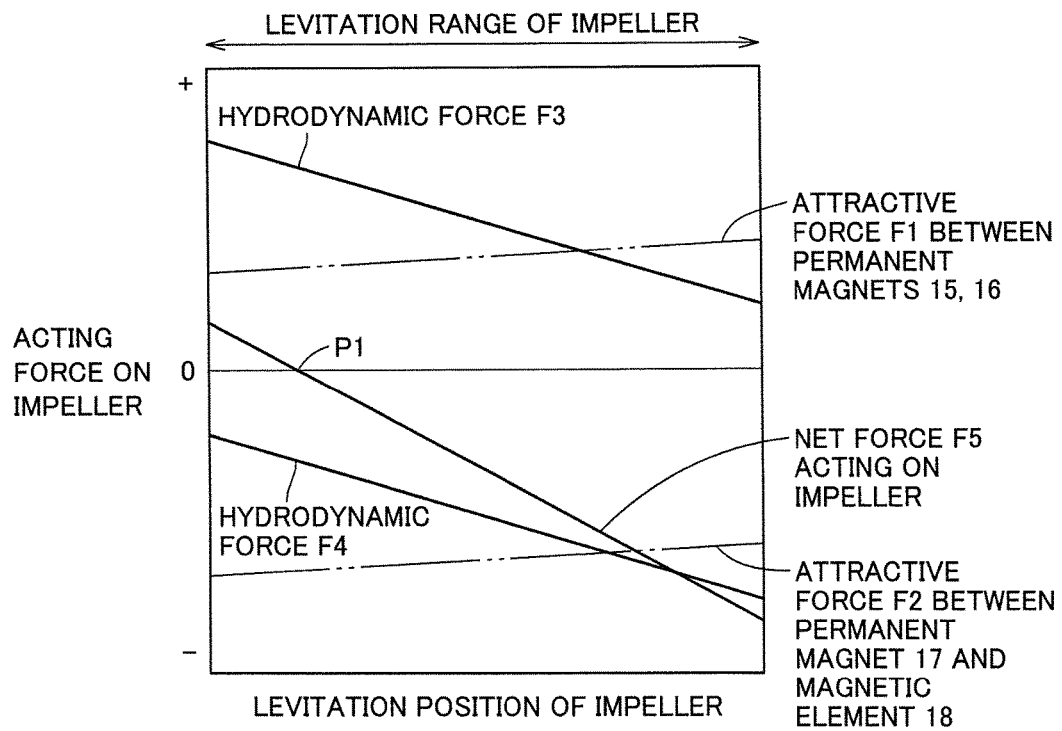
FIG. 13 is a diagram illustrating forces acting on an impeller.

FIG. 13 is a diagram illustrating forces acting on impeller 10 when magnitude of a resultant force of an attractive force F1 between permanent magnets 15 and 16 and an attractive force F2 between permanent magnet 17 and magnetic element 18 is adjusted to zero at a position P1 other than a central position of the movable range of impeller 10 in blood chamber 7. The rotation speed of impeller 10 is kept at a rated value.

That is, it is assumed that attractive force F1 between permanent magnets 15 and 16 is set to be smaller than attractive force F2 between permanent magnet 17 and magnetic element 18, and a levitation position of impeller 10 where their resultant force becomes zero is on the dividing wall 6 side relative to the center of the movable range of the impeller. Grooves for hydrodynamic bearing 21, 22 have the same shape.

A horizontal axis of FIG. 13 represents a position of impeller 10 (the left side in the figure being the dividing wall 6 side), and a vertical axis represents forces acting on impeller 10. Force acting on impeller 10 toward dividing wall 6 is expressed as a negative acting force. As the forces acting on impeller 10, attractive force F1 between permanent magnets 15 and 16, attractive force F2 between permanent magnet 17 and magnetic element 18, a hydrodynamic force F3 generated by grooves for hydrodynamic bearing 21, a hydrodynamic force F4 generated by grooves for hydrodynamic bearing 22, and a "net force F5 acting on impeller" which is their resultant force are illustrated.

As can be seen in FIG. 13, at a position where net force F5 acting on impeller 10 becomes zero, the levitation position of impeller 10 is significantly deviated from the central position of the movable range of impeller 10. As a result, a distance between rotating impeller 10 and dividing wall 6 becomes narrower, and impeller 10 is brought into contact with dividing wall 6 even by the action of a small disturbance force on impeller 10.

Figure 14:
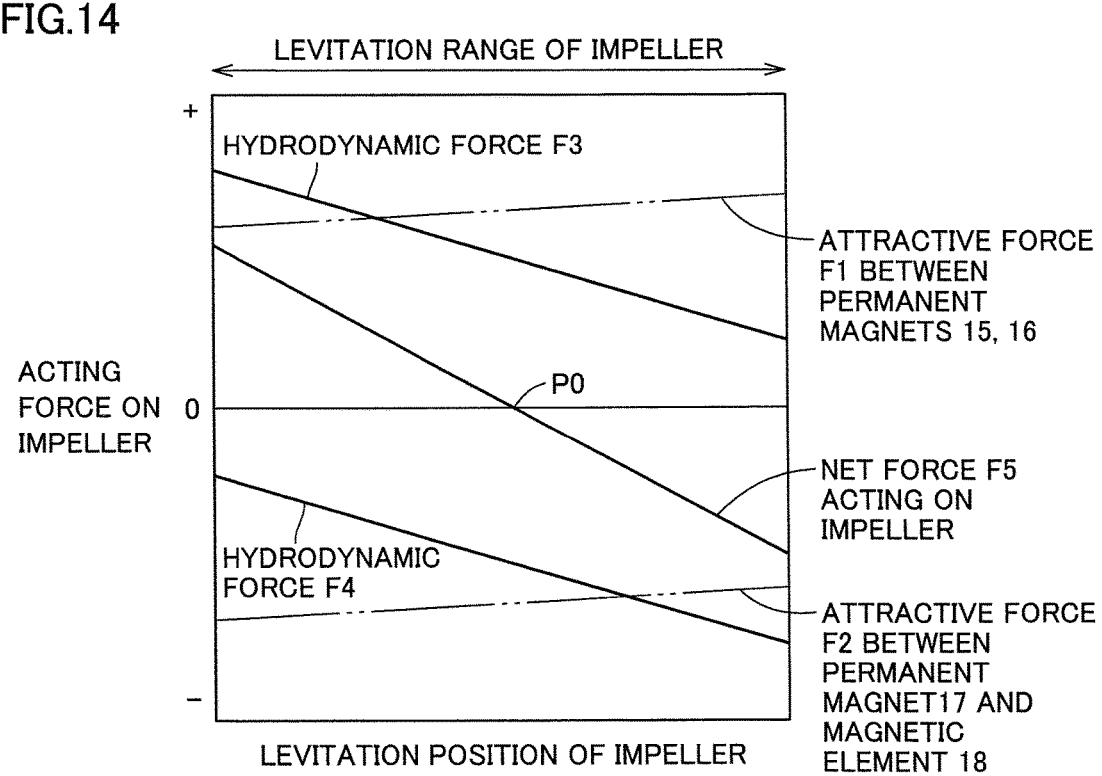
FIG. 14 is another diagram illustrating forces acting on the impeller.

In contrast, FIG. 14 illustrates forces acting on impeller 10 when a magnitude of the resultant force of attractive force F1 between permanent magnets 15 and 16 and attractive force F2 between permanent magnet 17 and magnetic element 18 is adjusted to zero at a central position P0 of the movable range of impeller 10 in blood chamber 7. The rotation speed of impeller 10 is kept at the rated value in this case as well.

Namely, attractive force F1 between permanent magnets 15 and 16 and attractive force F2 between permanent magnet 17 and magnetic element 18 are set to be substantially equal to each other. In addition, grooves for hydrodynamic bearing 21, 22 have the same shape. In this case, supporting rigidity for the levitation position of impeller 10 is higher than in the example shown in FIG. 13. Further, since net force F5 acting on impeller 10 is zero at the center of the movable range, impeller 10 is levitated at the central position when a disturbance force is not acting on impeller 10.

As such, a levitation position of impeller 10 is determined by balance among attractive force F1 between permanent magnets 15 and 16, attractive force F2 between permanent magnet 17 and magnetic element 18, and hydrodynamic forces F3, F4 generated by grooves for hydrodynamic bearing 21, 22 during rotation of impeller 10. By making F1 and F2 substantially equal to each other and by forming grooves for hydrodynamic bearing 21, 22 in the same shape, impeller 10 can be levitated substantially in a central portion of blood chamber 7 during rotation of impeller 10. Since impeller 10 has such a shape that vanes are formed between two discs as shown in FIGS. 3 and 4, two surfaces facing the inner wall of housing 2 can be formed to have the same shape and the same dimensions. Therefore, it is possible to provide grooves for hydrodynamic bearing 21, 22 having a function to generate substantially the same hydrodynamic force on both sides of impeller 10.

In this case, impeller 10 is levitated at the central position of blood chamber 7, and thus held at a position farthest from the inner wall of housing 2. As a result, even if the levitation position of impeller 10 is changed due to application of a disturbance force to levitated impeller 10, the possibility that impeller 10 is brought into contact with the inner wall of housing 2 is lowered, thus also lowering the possibility of occurrence of thrombus and hemolysis resulting from such contact.

While two grooves for hydrodynamic bearing 21, 22 have the same shape in the examples shown in FIGS. 13 and 14, grooves for hydrodynamic bearing 21, 22 may be different from each other in shape and hydrodynamic force generating function. For example, when disturbance acts on impeller 10 always in one direction due to fluid force or the like during pumping, performance of a groove for hydrodynamic bearing in the disturbance direction may be made higher than performance of the other groove for hydrodynamic bearing, thereby levitating and rotating impeller 10 at the central position of housing 2. As a result, the probability of contact between impeller 10 and housing 2 can be lowered, thereby attaining stable levitation performance of impeller 10.

Furthermore, when an absolute value of a negative axial supporting rigidity value of impeller 10 which is constituted of attractive force F1 between permanent magnets 15 and 16 and attractive force F2 between permanent magnet 17 and magnetic element 18 is expressed as Ka, an absolute value of a positive radial rigidity value is expressed as Kr, and an absolute value of a positive rigidity value obtained by two grooves for hydrodynamic bearing 21, 22 in a normal rotation speed range where impeller 10 rotates is expressed as Kg, it is preferable that relation of Kg>Ka+Kr be satisfied.

Specifically, when absolute value Ka of the negative axial rigidity value is 20000 N/m and absolute value Kr of the positive radial rigidity value is 10000 N/m, absolute value Kg of the positive rigidity value obtained by two grooves for hydrodynamic bearing 21, 22 in the rotation speed range where impeller 10 normally rotates is set to a value higher than 30000 N/m.

The axial supporting rigidity for impeller 10 is a value obtained by subtracting negative rigidity due to the attractive force between the magnetic elements and the like from rigidity resulting from the hydrodynamic force generated by grooves for hydrodynamic bearing 21, 22. Thus, by satisfying the relation of Kg>Ka+Kr, the axial supporting rigidity for impeller 10 can be made higher than the radial supporting rigidity. With such setting, movement of impeller 10 can be suppressed more in the axial direction than in the radial direction when a disturbance force acts on impeller 10, thereby avoiding mechanical contact between impeller 10 and housing 2 in a portion where grooves for hydrodynamic bearing 21 are formed.

In particular, since grooves for hydrodynamic bearing 21, 22 are provided as concave portions in planar surfaces as shown in FIGS. 3, 5 and 6, mechanical contact between housing 2 and impeller 10 in these portions during rotation of impeller 10 may result in damage to one or both of a surface of impeller 10 and a surface of the inner wall of housing 2 (projections and recesses in the surfaces), and blood passage through this portion may cause occurrence of thrombus and hemolysis. In order to prevent mechanical contact at grooves for hydrodynamic bearing 21, 22 to suppress thrombus and hemolysis, it is effective to make the axial rigidity higher than the radial rigidity.

Whirl occurs in unbalanced impeller 10 during rotation, and this whirl is greatest when a natural frequency determined by the mass of impeller 10 and the supporting rigidity value of impeller 10 matches the rotation speed of impeller 10.

Since the radial supporting rigidity for impeller 10 is smaller than the axial supporting rigidity in pump unit 1, it is preferable to set a maximum rotation speed of impeller 10 to be equal to or lower than the radial natural frequency. Accordingly, in order to prevent mechanical contact between impeller 10 and housing 2, when a radial rigidity value of impeller 10 which is constituted of attractive force F1 between permanent magnets 15 and 16 and attractive force F2 between permanent magnet 17 and magnetic element 18 is expressed as Kr (N/m), the mass of impeller 10 is expressed as m (kg), and the rotation speed of the impeller is expressed as ω (rad/s), it is preferable that relation of $\omega < (Kr/m)^{0.5}$ be satisfied.

Specifically, when the mass of impeller 10 is 0.03 kg and the radial rigidity value is 2000 N/m, the maximum rotation speed of impeller 10 is set to 258 rad/s (2465 rpm) or lower. Conversely, when the maximum rotation speed of impeller 10 is set to 366 rad/s (3500 rpm), the radial rigidity is set to 4018 N/m or higher.

It is further preferable to set the maximum rotation speed of impeller 10 to 80% or lower of this Co. Specifically, when the mass of impeller 10 is 0.03 kg and the radial rigidity value is 2000 N/m, the maximum rotation speed is set to 206.4 rad/s (1971 rpm) or lower. Conversely, when it is desired to set the maximum rotation speed of impeller 10 to 366 rad/s (3500 rpm), the radial rigidity value is set to 6279 N/m or higher. By thus setting the maximum rotation speed of impeller 10, contact between rotating impeller 10 and housing 2 can be suppressed.

When the rigidity due to the hydrodynamic force generated by grooves for hydrodynamic bearing 21, 22 becomes higher than the negative axial rigidity value of impeller 10 which is constituted of attractive force F1 between permanent magnets 15 and 16 and attractive force F2 between permanent magnet 17 and magnetic element 18, impeller 10 and housing 2 are not in contact with each other. It is thus preferable to minimize this negative rigidity value. In order to minimize the negative rigidity value, it is preferable that surfaces facing each other of permanent magnets 15, 16 have different sizes. For example, by making the size of permanent magnet 16 smaller than that of permanent magnet 15, a rate of variation in attractive force that varies with a distance between the magnets, that is, the negative rigidity, can be minimized, thereby preventing lowering in supporting rigidity for the impeller.

It is also preferable to check to see that impeller 10 is in contact with dividing wall 6 before activating impeller 10 to rotate.

Namely, when impeller 10 is not rotating, impeller 10 is not supported without contacting by grooves for hydrodynamic bearing 21, 22, but is in contact with housing 2 with a high surface pressure due to attractive force F1 between permanent magnets 15 and 16 and attractive force F2 between permanent magnet 17 and magnetic element 18. Further, when impeller 10 is rotated by magnetic interaction between coil 20 and magnetic element 18 in motor chamber 8 and permanent magnet 17 in impeller 10 as in pump unit 1, starting torque is smaller than in an example where an impeller is driven to rotate through magnetic coupling between permanent magnets as shown in FIG. 3 of Patent Document 2. It is thus difficult to smoothly activate impeller 10 to rotate.

When shroud 12 of impeller 10 is in contact with dividing wall 6, however, permanent magnet 17 in impeller 10 and magnetic element 18 in motor chamber 8 are closer to each other than when shroud 11 of impeller 10 is in contact with the inner wall of blood chamber 7, which allows increase in rotational torque during activation of impeller 10, thereby smoothly activating impeller 10 to rotate.

As described above, however, when impeller 10 is rotating, attractive force F1 between permanent magnets 15 and 16 and attractive force F2 between permanent magnet 17 and magnetic element 18 are set to be balanced with each other when impeller 10 is positioned around the center of the movable range of impeller 10. Thus, impeller 10 is not necessarily in contact with dividing wall 6 when impeller 10 is not rotating.

For this reason, this centrifugal blood pump apparatus is provided with means for moving impeller 10 toward dividing wall 6 before activating impeller 10 to rotate. Specifically, a current is fed through the plurality of coils 20 to increase attractive force F2 between permanent magnet 17 and magnetic element 18, to move impeller 10 toward dividing wall 6.

Figure 15:
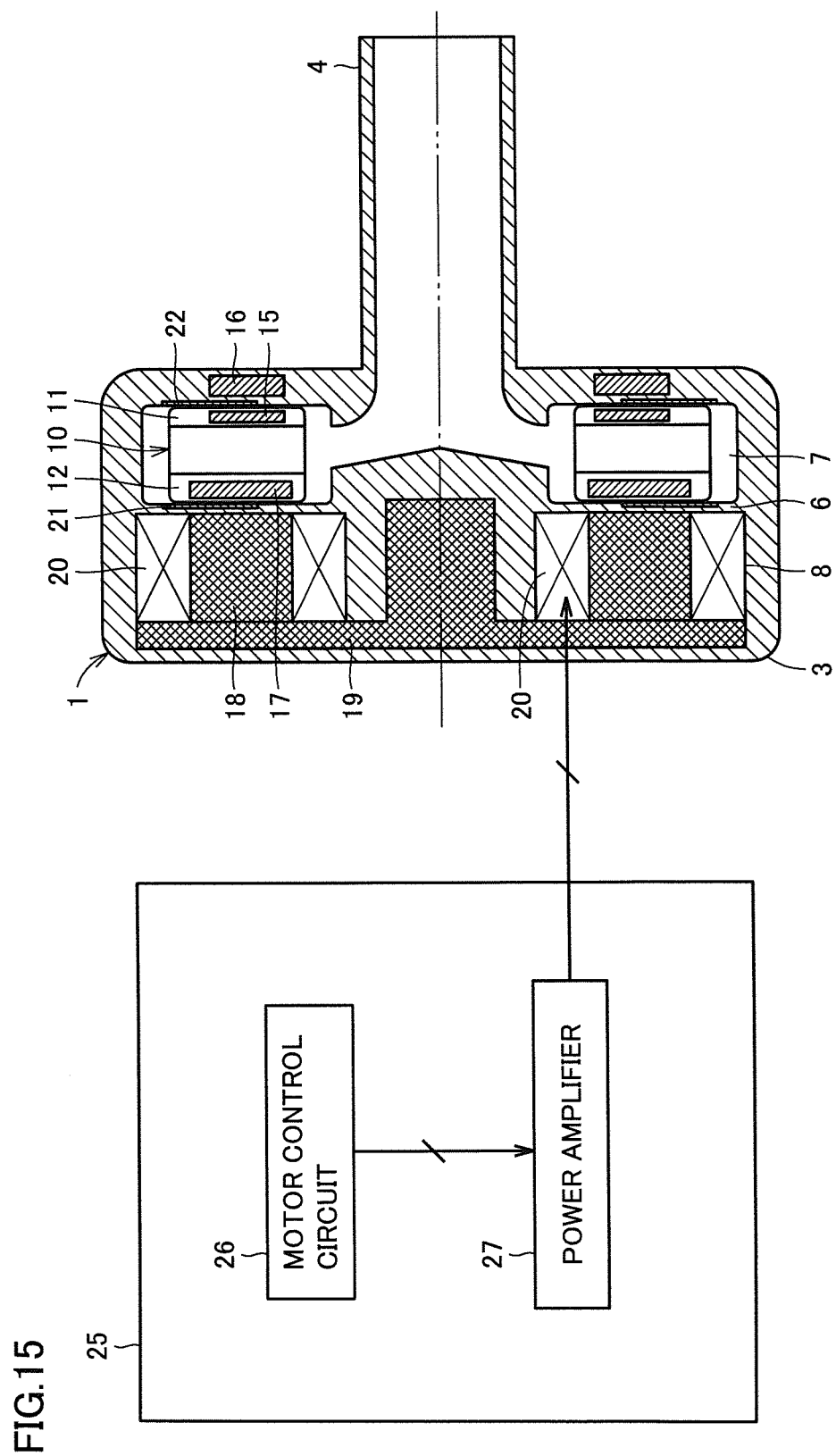
FIG. 15 is a block diagram showing the configuration of a controller for controlling the pump unit shown in FIGS. 1 to 12.

FIG. 15 is a block diagram showing the configuration of a controller 25 for controlling pump unit 1. In FIG. 15, controller 25 includes a motor control circuit 26 and a power amplifier 27. Motor control circuit 26 outputs three-phase control signals in the power distribution system shifted by 120 degrees, for example. Power amplifier 27 amplifies the three-phase control signals from motor control circuit 26, and generates three-phase voltages VU, VV, VW shown in FIG. 8. Three-phase voltages VU, VV, VW are applied to first to third coils 20 described with reference to FIG. 7, respectively. As a result, during normal operation, impeller 10 rotates at a prescribed rotation speed at the central position of the movable range.

Figure 16:
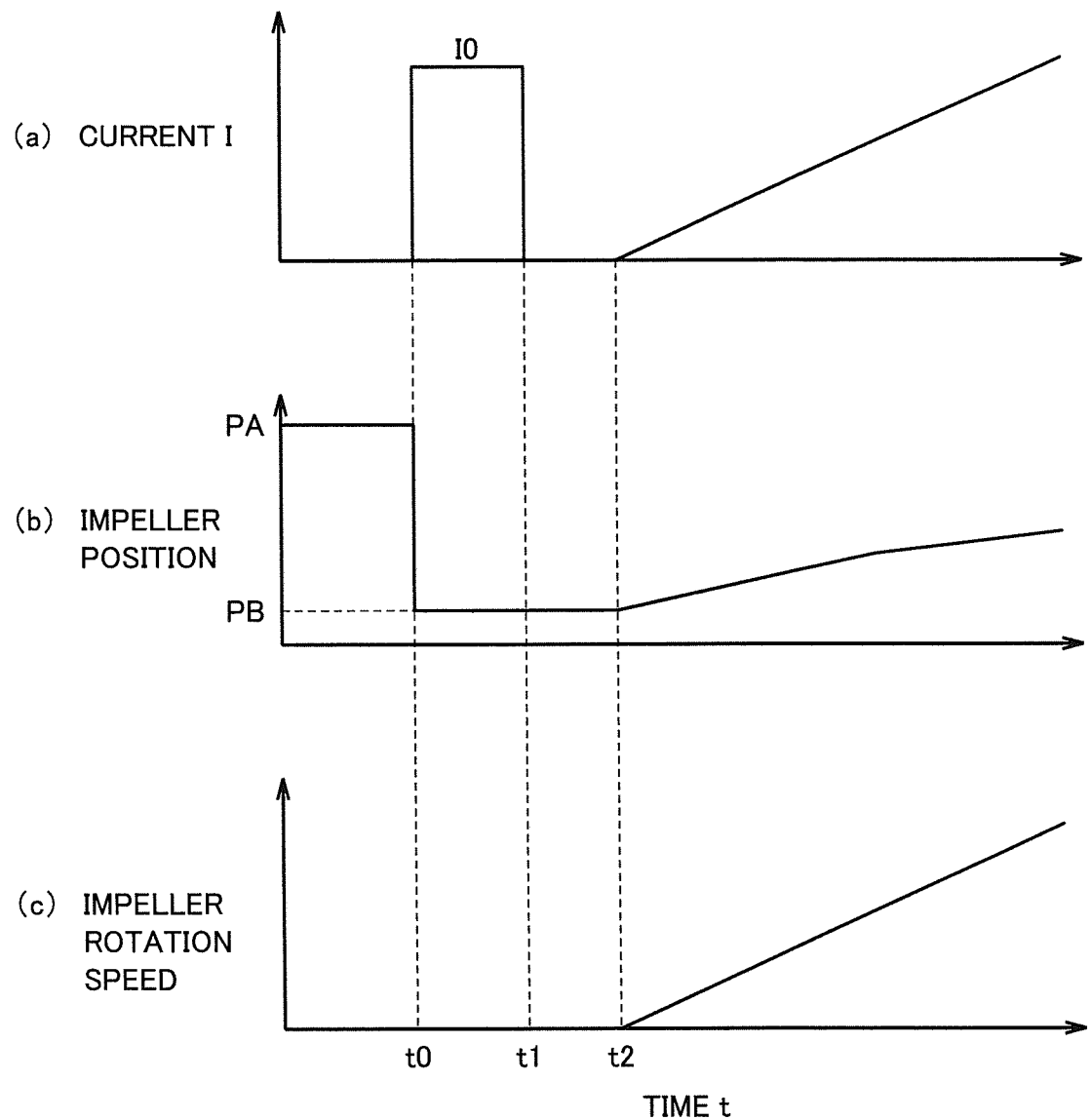
FIG. 16 is a time chart illustrating operation of the controller shown in FIG. 15.

FIGS. 16 (a) to (c) are time charts illustrating temporal variations of a coil current I when impeller 10 is activated to rotate, a position of impeller 10, and a rotation speed of impeller 10. Referring to FIGS. 16 (a) to (c), it is assumed that, in an initial state, shroud 11 of impeller 10 is in contact with the inner wall of blood chamber 7, and impeller 10 is at a position PA. At time t0, a predetermined current I0 is fed through coils 20. As a result, attractive force F2 between permanent magnet 17 and magnetic element 18 becomes higher than attractive force F1 between permanent magnets 15 and 16, so that impeller 10 moves to a position PB on the dividing wall 6 side, causing shroud 12 of impeller 10 to be in contact with dividing wall 6. When impeller 10 moved to position PB, current I0 is cut off (time t1). It is preferable to provide a sensor for detecting a position of impeller 10 in blood chamber 7, and check to see that impeller 10 is in contact with dividing wall 6 before cutting off current I0.

Then, coil current I is gradually increased to a predetermined rated value. Here, impeller 10 is in contact with dividing wall 6, and thus smoothly rotates. With the increase in coil current I, impeller 10 moves from position PB on the dividing wall 6 side to the central position of the movable range.

As described above, in the first embodiment, flexible substrate 23 is provided to surround nine coils 20, nine coils 20 are connected to pins 24a to 24c of connector 24 by flexible substrate 23, and three-phase driving voltages VU, VV, VW are supplied to nine coils 20 via wiring patterns L1 to L3 formed on flexible substrate 23. Thus, assembling workability, productivity and reliability can be increased while the apparatus maintains a small size and a small thickness, as compared to an example where nine coils 20 are directly soldered to the three-phase power supply lines. Furthermore, since nine coils 20 are connected to connector 24 by only one flexible substrate 23, the number of components and the cost can be reduced.

Moreover, the arrangement of 18 electrodes EL in a dispersed manner in the nine clearances between the inner circumferential surface of cylindrically arranged flexible substrate 23 and nine cylindrical coils 20 allows for efficient use of space and dimension reduction of the apparatus. Furthermore, the use of bendable and flexible substrate 23 allows for three-dimensional mounting of wiring patterns L0 to L3 and the like depending on the shape of the drive unit.

Figure 17:
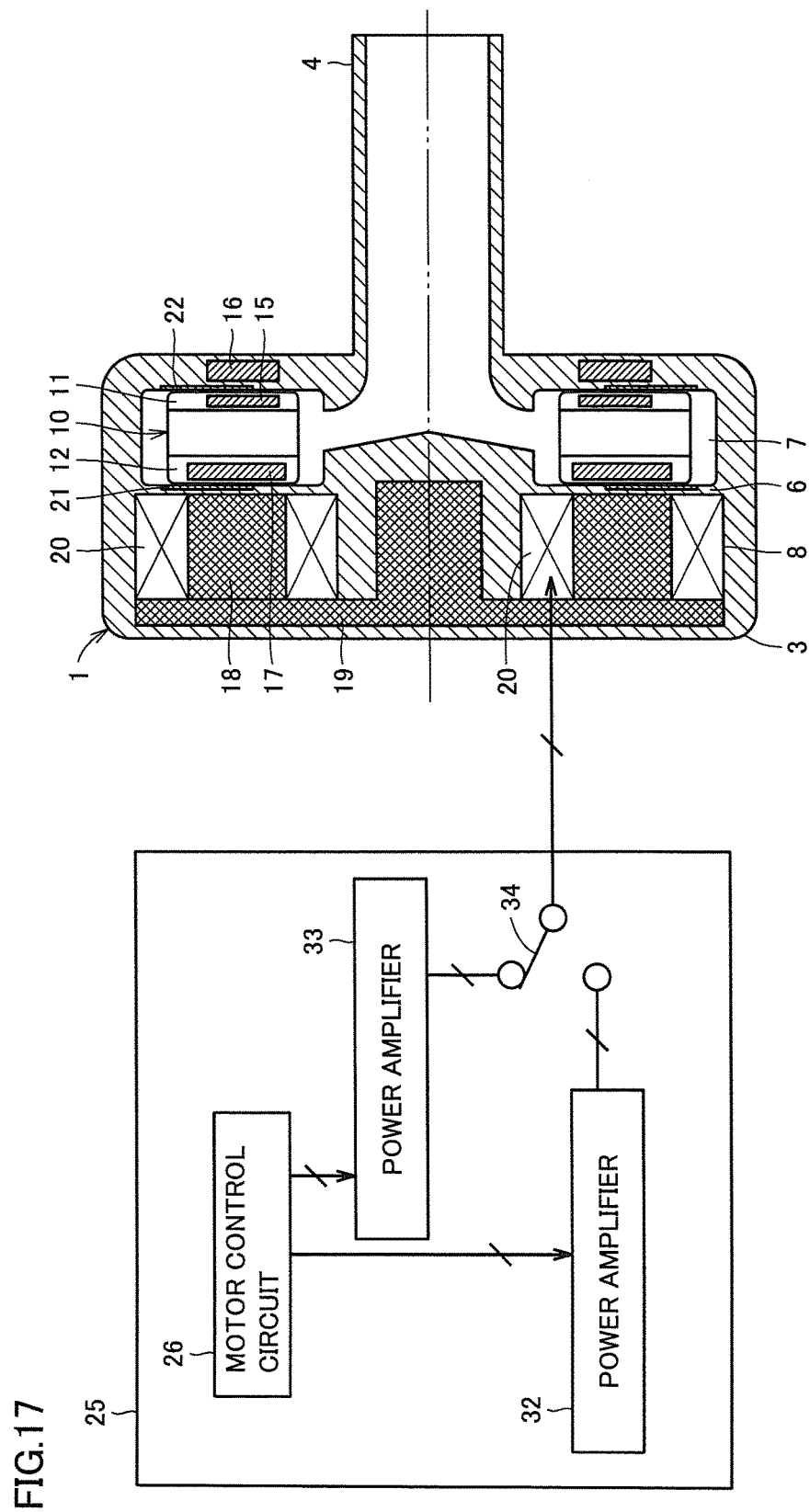
FIG. 17 is a block diagram showing a modification of the first embodiment.

FIG. 17 is a block diagram showing a modification of the first embodiment. This figure shows an example of a configuration where power source supply is switched between during activation of the impeller for rotation and the remaining period. Referring to FIG. 17, in this modification, power amplifier 27 in FIG. 15 is replaced with power amplifiers 32, 33 and a switch 34. Between times t0 and t1 in FIG. 16, an output signal from motor control circuit 26 is provided to power amplifier 32 and an output voltage from power amplifier 32 is applied to coils 20 via switch 34, causing current I0 to flow through coils 20. After time t2, an output signal from motor control circuit 26 is provided to power amplifier 33 and an output voltage from power amplifier 33 is applied to coils 20 via switch 34, causing a current to flow through coils 20.

Figure 18:
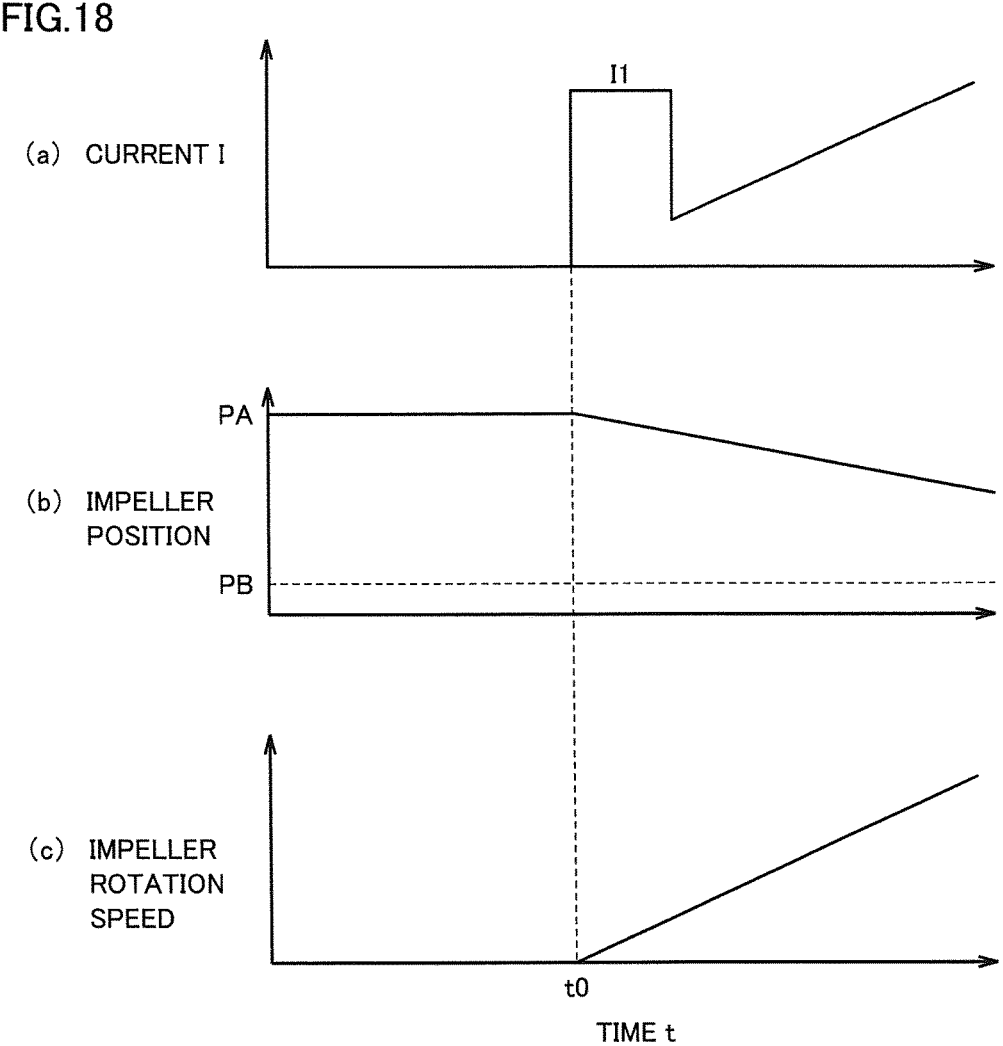
FIG. 18 is a time chart illustrating another modification of the first embodiment.

FIGS. 18 (a) to (c) are time charts illustrating another modification of the first embodiment. Referring to FIGS. 18 (a) to (c), it is assumed that, in an initial state, shroud 11 of impeller 10 is in contact with the inner wall of blood chamber 7, and impeller 10 is at position PA. At time t0, a predetermined current I1 is fed through coils 20. Motor control circuit 26 outputs three-phase control signals in the power distribution system shifted by 120 degrees, for example. Power amplifier 27 amplifies the three-phase control signals from motor control circuit 26 and generates three-phase voltages VU, VV, VW shown in FIG. 8. Three-phase voltages VU, VV, VW are applied to first to third coils 20 described with reference to FIG. 7, respectively. Accordingly, rotating magnetic field is applied to impeller 10 by current I1. Current I1 is larger than current I0 in FIG. 16 and it can activate impeller 10 to rotate even when shroud 11 of impeller 10 is in contact with the inner wall of blood chamber 7. After activation for rotation is confirmed, coil current I is reduced and gradually increased to the predetermined rated value. In this manner, even when impeller 10 is on the position PA side, an overcurrent may be fed through coils 20 only when impeller 10 is activated to rotate.

In addition, a diamond-like carbon (DLC) coating may be formed on at least one of the surface of the inner wall of blood chamber 7 and the surface of dividing wall 6, and the surface of impeller 10. As a result, frictional force between impeller 10, and the inner wall of blood chamber 7 and dividing wall 6 can be lowered to smoothly activate the impeller to rotate. A fluorine-based resin coating, a paraxylylene-based resin coating or the like may be formed instead of the diamond-like carbon coating.

Figure 19:
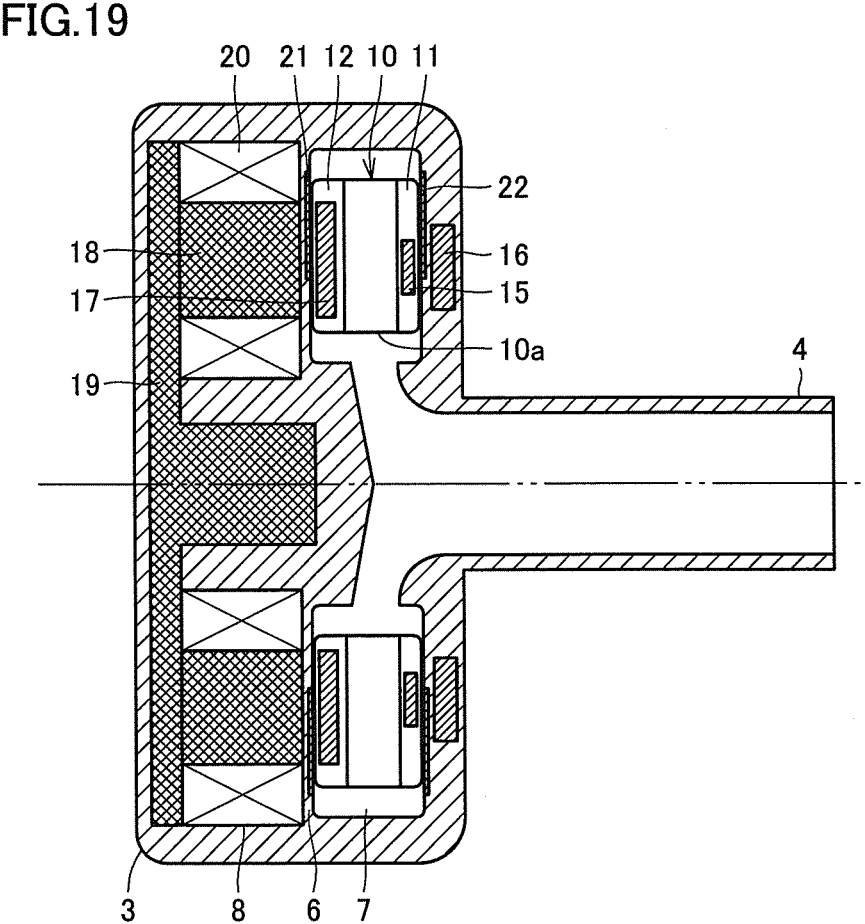
FIG. 19 is a cross-sectional view showing yet another modification of the first embodiment.

FIG. 19 is a cross-sectional view showing yet another modification of the first embodiment, which is compared to FIG. 3. Referring to FIG. 19, in this modification, the surfaces facing each other of permanent magnets 15 and 16 have different sizes. While the surfaces facing each other of permanent magnets 15 and 16 have the same size in FIG. 3, by making the surfaces facing each other of permanent magnets 15 and 16 have different sizes, the amount of variation in attractive force which varies with a distance between the magnets, namely, the negative rigidity, can be minimized, thereby preventing lowering in supporting rigidity for impeller 10.

Figure 20:
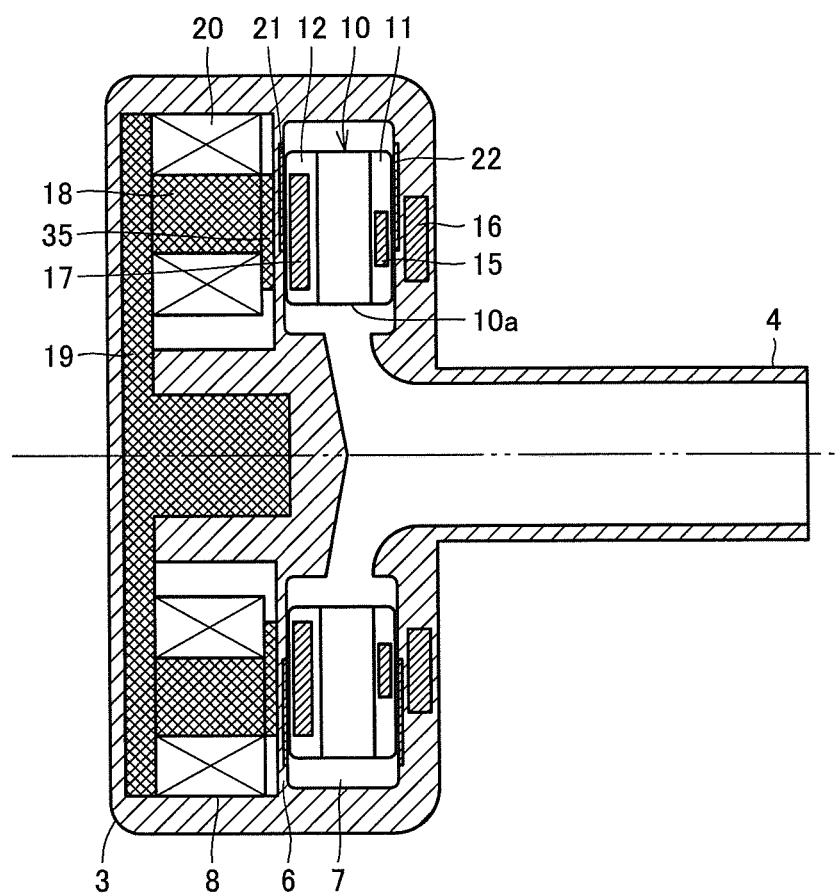
FIG. 20 is a cross-sectional view showing yet another modification of the first embodiment.

FIG. 20 is a cross-sectional view showing yet another modification of the first embodiment, which is compared to FIG. 7. Referring to FIG. 20, in this modification, a magnetic element 35 is provided on a tip surface of each magnetic element 18 facing permanent magnet 17. A surface of magnetic element 35 facing permanent magnet 17 has an area larger than an area of the tip surface of magnetic element 18. In this modification, an attractive force of magnetic elements 18 and 35 on permanent magnet 17 can be increased, thereby enhancing energy efficiency when driving impeller 10 to rotate.

Figure 21:
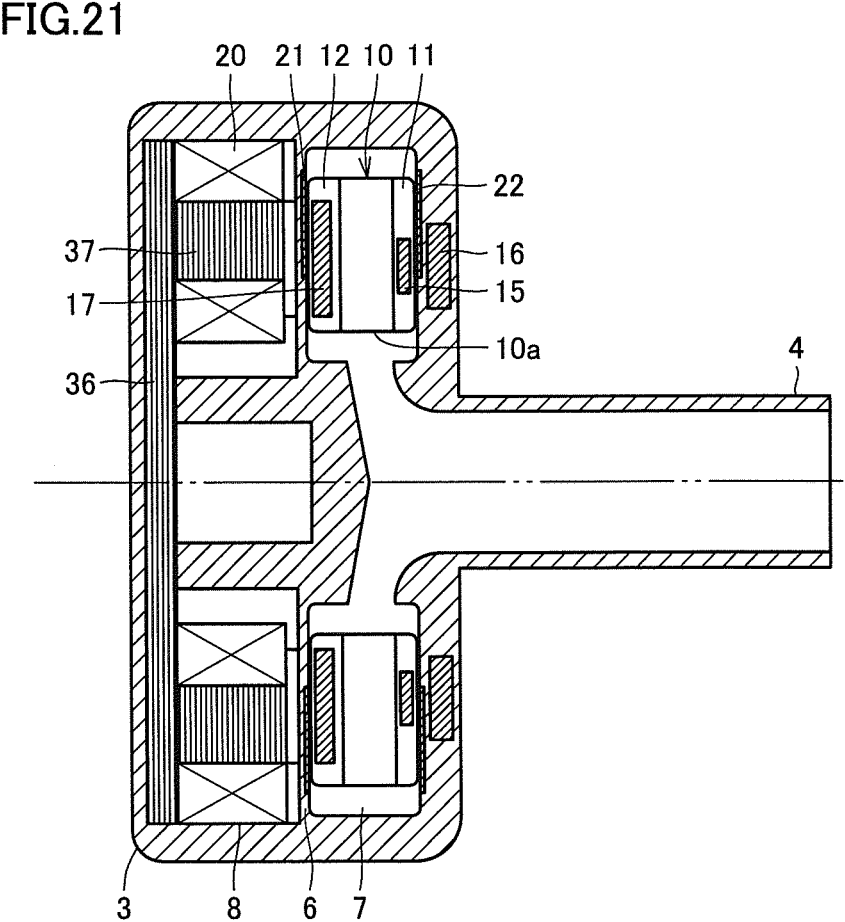
FIG. 21 is a cross-sectional view showing yet another modification of the first embodiment.

FIG. 21 is a cross-sectional view showing yet another modification of the first embodiment, which is compared to FIG. 19. Referring to FIG. 21, in this modification, yoke 19 is replaced with a yoke 36, and magnetic element 18 is replaced with a magnetic element 37. Yoke 36 and magnetic element 37 each include a plurality of steel plates stacked in a length direction of a rotation axis of impeller 10. In this modification, eddy current loss that occurs in yoke 36 and magnetic element 37 can be reduced, thereby enhancing energy efficiency when driving impeller 10 to rotate.

Figure 22:
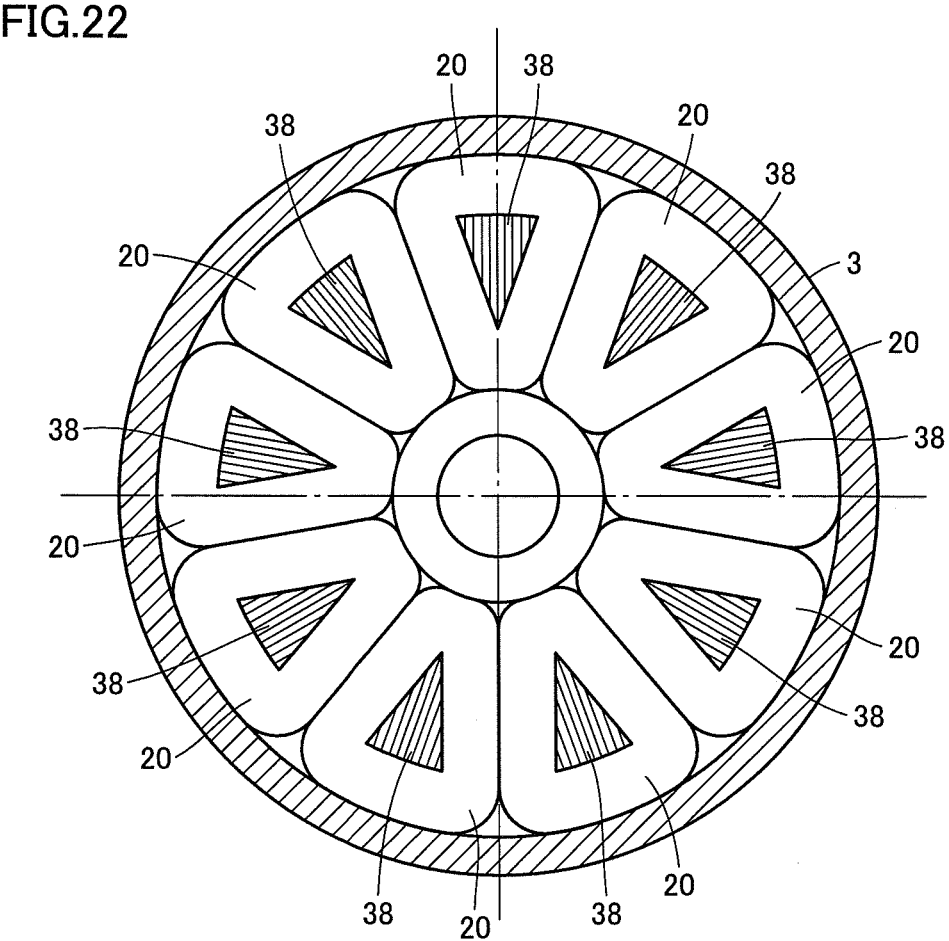
FIG. 22 is a cross-sectional view showing yet another modification of the first embodiment.
Figure 23:
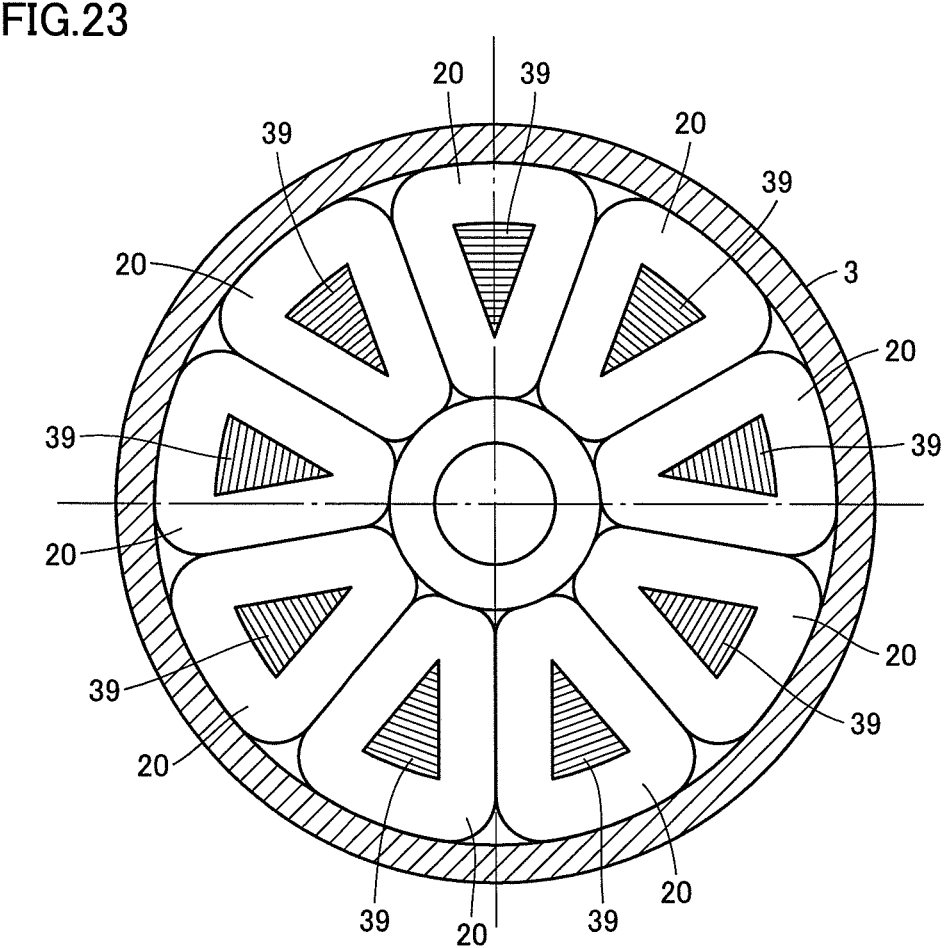
FIG. 23 is a cross-sectional view showing yet another modification of the first embodiment.

Alternatively, as shown in FIG. 22, magnetic element 37 may be replaced with a magnetic element 38 including a plurality of steel plates stacked in a rotation direction of impeller 10. Alternatively, as shown in FIG. 23, magnetic element 37 may be replaced with a magnetic element 39 including a plurality of steel plates stacked in a radial direction of impeller 10. The same effect as that in the modification of FIG. 21 can be obtained in these cases as well.

Figure 24:
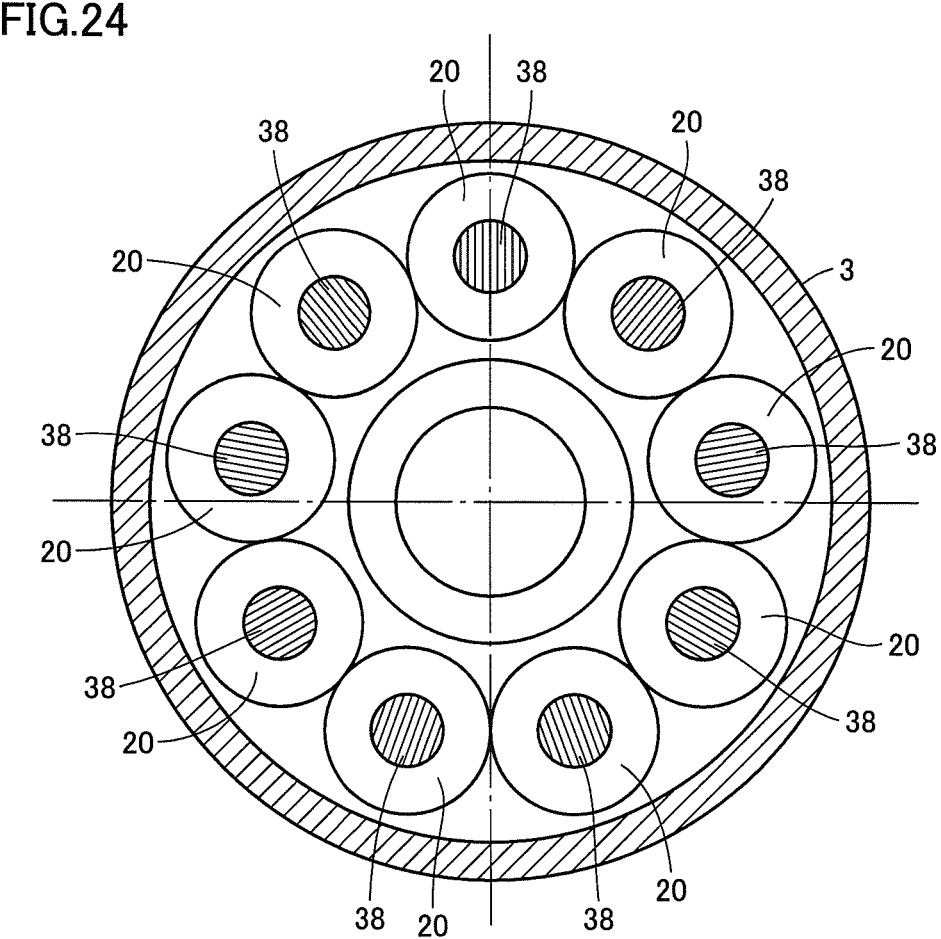
FIG. 24 is a cross-sectional view showing yet another modification of the first embodiment.
Figure 25:
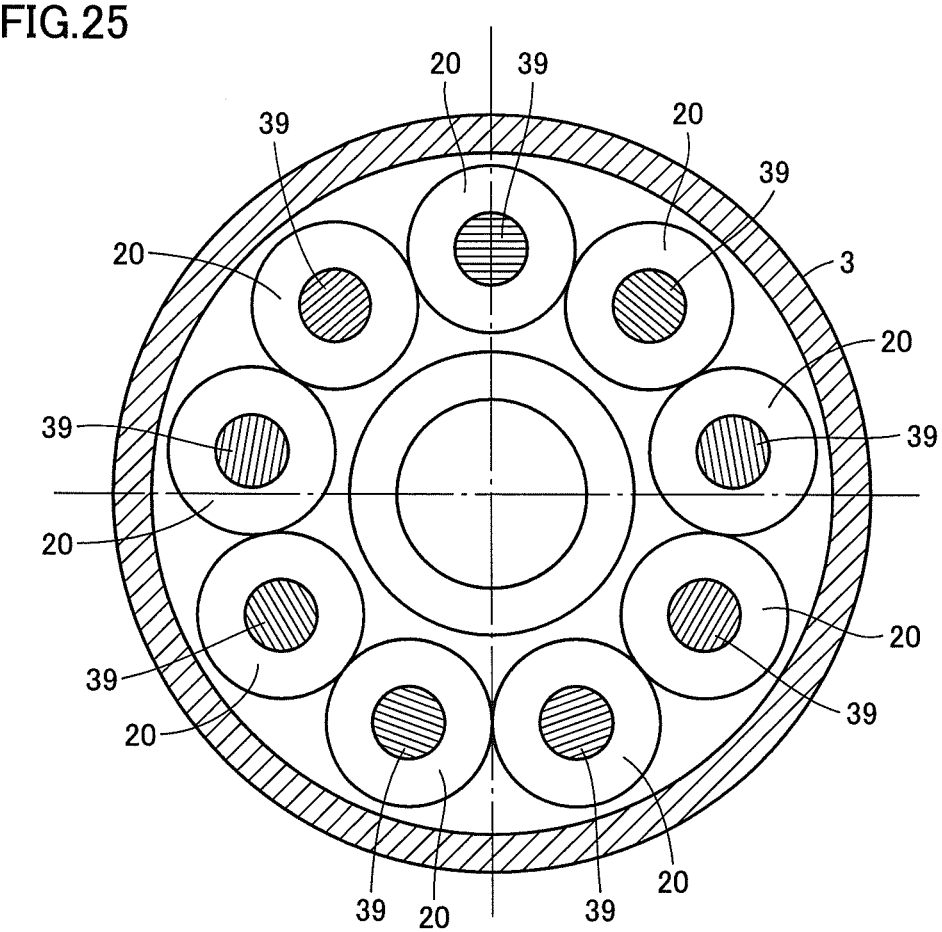
FIG. 25 is a cross-sectional view showing yet another modification of the first embodiment.

Alternatively, as shown in FIG. 24, each magnetic element 38 may be formed in a cylindrical shape. Alternatively, as shown in FIG. 25, each magnetic element 39 may be formed in a cylindrical shape. In these cases, coil 20 can be readily wound around magnetic elements 38 and 39.

Figure 26:
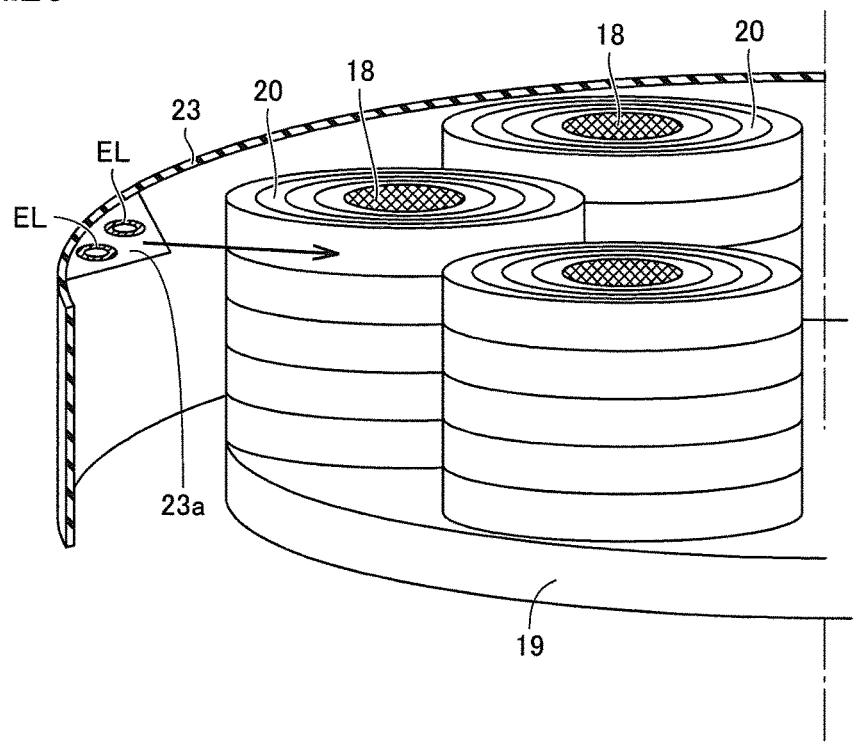
FIG. 26 shows yet another modification of the first embodiment.
Figure 27:
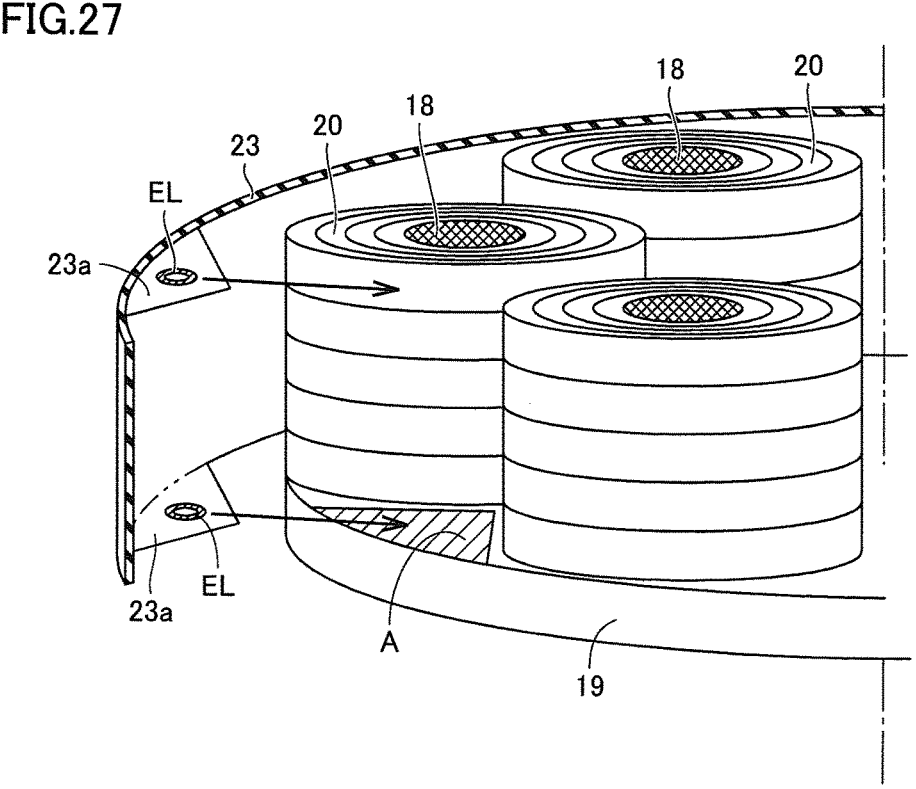
FIG. 27 shows yet another modification of the first embodiment.

Alternatively, as shown in FIG. 26, bent portions 23a may be provided at an end face (on the dividing wall 6 side) of flexible substrate 23 opposite to an end face thereof on the yoke 19 side. Alternatively, as shown in FIG. 27, bent portions 23a may be provided at both end faces on the yoke 19 side and on the dividing wall 6 side of flexible substrate 23. In this case, each bent portion 23a may be provided with one electrode EL. In this modification, bent portions 23a and the terminals of coils 20 correspond with one another in a one-to-one relationship, thereby improving the efficiency of connecting operation and reliability.

Figure 28:
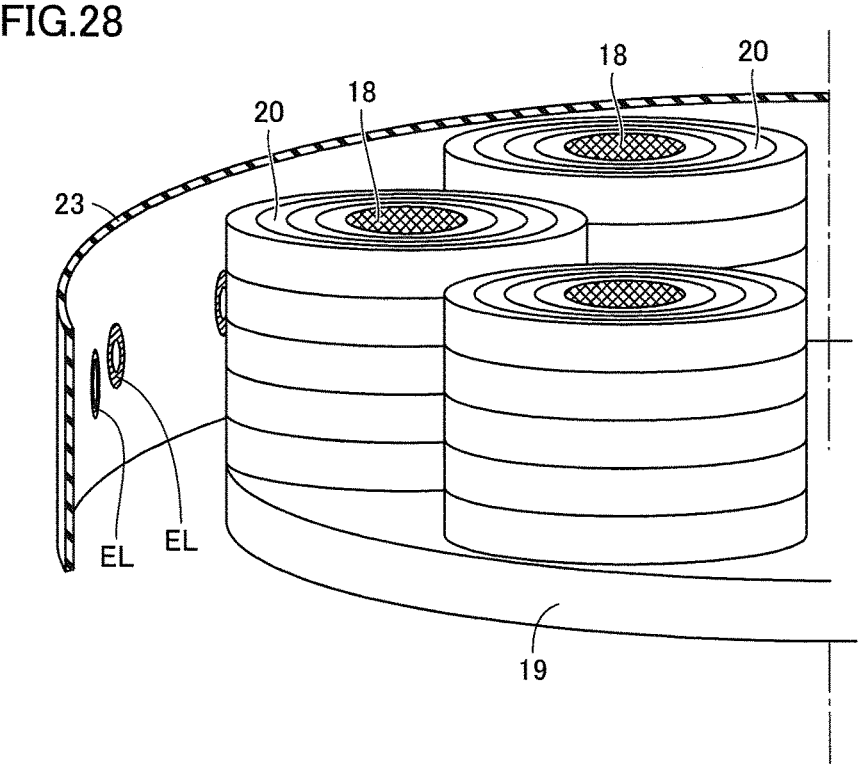
FIG. 28 shows yet another modification of the first embodiment.

Alternatively, as shown in FIG. 28, nine pairs of electrodes EL may be provided at a substantially central portion of the inner circumferential surface of flexible substrate 23. The nine pairs of electrodes EL are provided correspondingly to the respective nine gaps between nine coils 20. Each coil 20 has two terminals connected to two electrodes EL adjacent to this coil 20. This modification does not need bent portions 23a, thereby simplifying the arrangement of flexible substrate 23.

Figure 29:
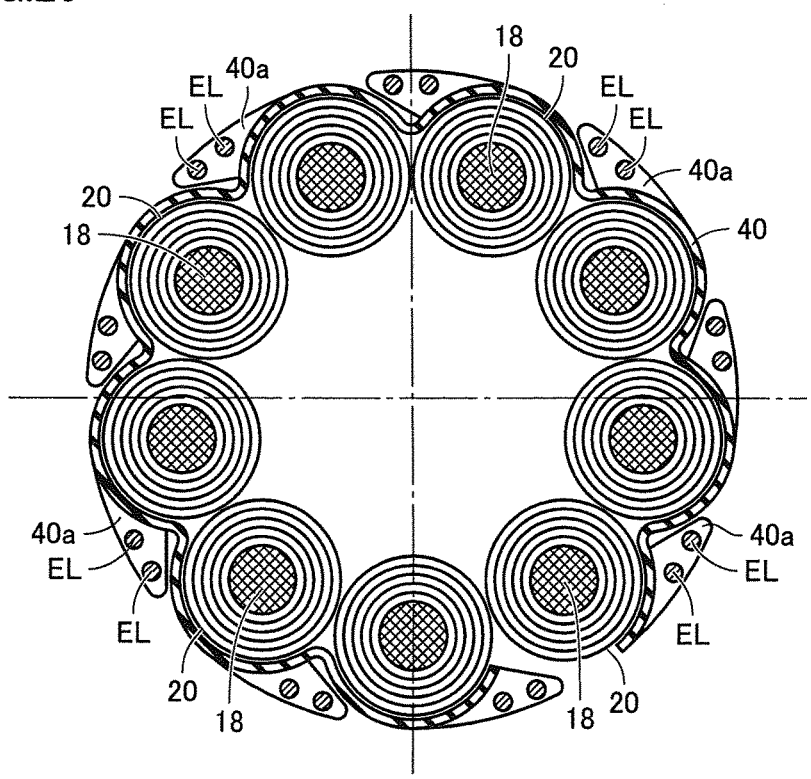
FIG. 29 is a cross-sectional view showing yet another modification of the first embodiment.

In a modification of FIG. 29, a strip-shaped flexible substrate 40 is formed in a corrugated shape along the outer circumference of each cylindrical coil 20, with nine recesses formed on an outer side of flexible substrate 40. At one end portion in a width direction of flexible substrate 40, nine tongue-shaped bent portions 40a are provided correspondingly to the respective nine recesses. Each bent portion 40a is bent at a right angle to the outer side of flexible substrate 40 so as to fit in the corresponding recess. Each bent portion 40a is provided with two electrodes EL. Each coil has two terminals connected to two electrodes EL adjacent to this coil 20. Although not shown, bent portions 40a may be provided at both end faces on the yoke 19 side and on the dividing wall 6 side of flexible substrate 40. In this case, each bent portion 40a may be provided with one electrode EL.

In this modification, bent portions 40a are arranged on the outer side of flexible substrate 40, thereby improving the workability of soldering between electrodes EL and the terminals of coils 20 and of potting. Furthermore, the arrangement of flexible substrate 40 in a corrugated shape along the outer circumference of each cylindrical coil 20 allows for reduction of the dimensions of the apparatus.

In the first embodiment where bent portions 23a are arranged on the inner side of flexible substrate 23, nine coils 20 need to be connected to 18 electrodes EL in a prescribed order. In contrast, in this modification where bent portions 23a are arranged on the outer side of flexible substrate 23, nine coils 20 may be connected to 18 electrodes EL in any order. In addition, if connection needs to be modified after assembly, the modification can be readily made.

Figure 30:
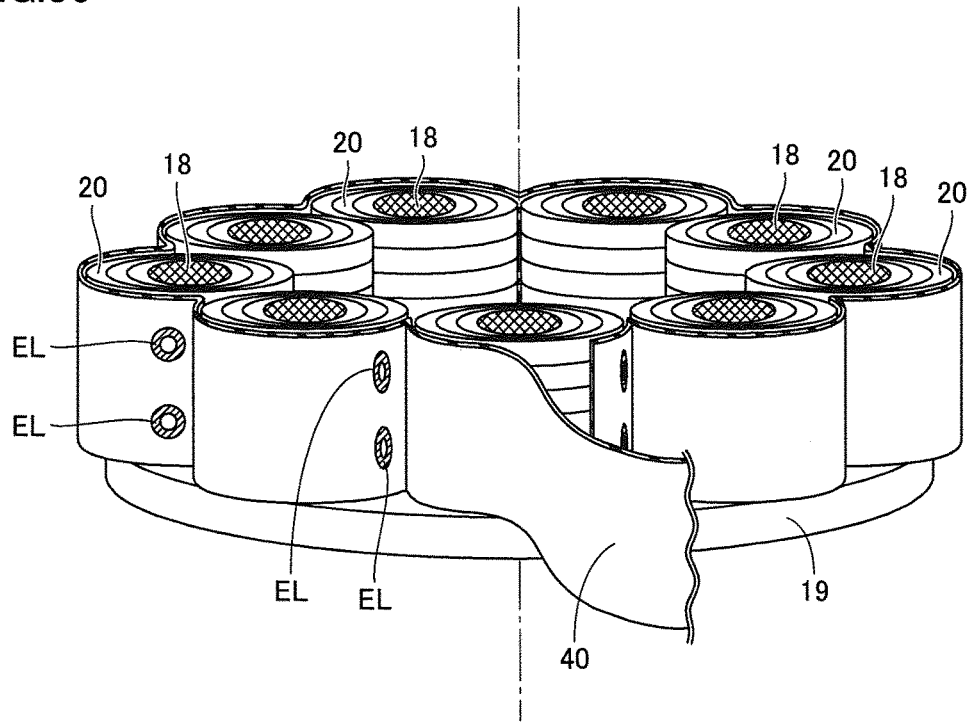
FIG. 30 shows yet another modification of the first embodiment.

In a modification of FIG. 30, in a manner similar to the modification of FIG. 29, strip-shaped flexible substrate 40 is formed in a corrugated shape along the outer circumference of each cylindrical coil 20, with nine recesses formed on the outer side of flexible substrate 40. In this modification, however, bent portions 40a are not provided, but nine pairs of electrodes EL are provided in the nine recesses of flexible substrate 40, respectively. One pair of electrodes EL is aligned in the corresponding recess at a prescribed interval in the width direction of flexible substrate 40. Each coil 20 has two terminals connected to two electrodes EL adjacent to this coil 20.

This modification does not need bent portions 40a, thereby simplifying the shape and arrangement of flexible substrate 40. Furthermore, a large working space can be secured to improve the efficiency of connecting operation and reliability. Moreover, the soldered portions can be readily potted to provide insulation, and all of the potted portions can be readily observed by visual inspection.

Figure 31:
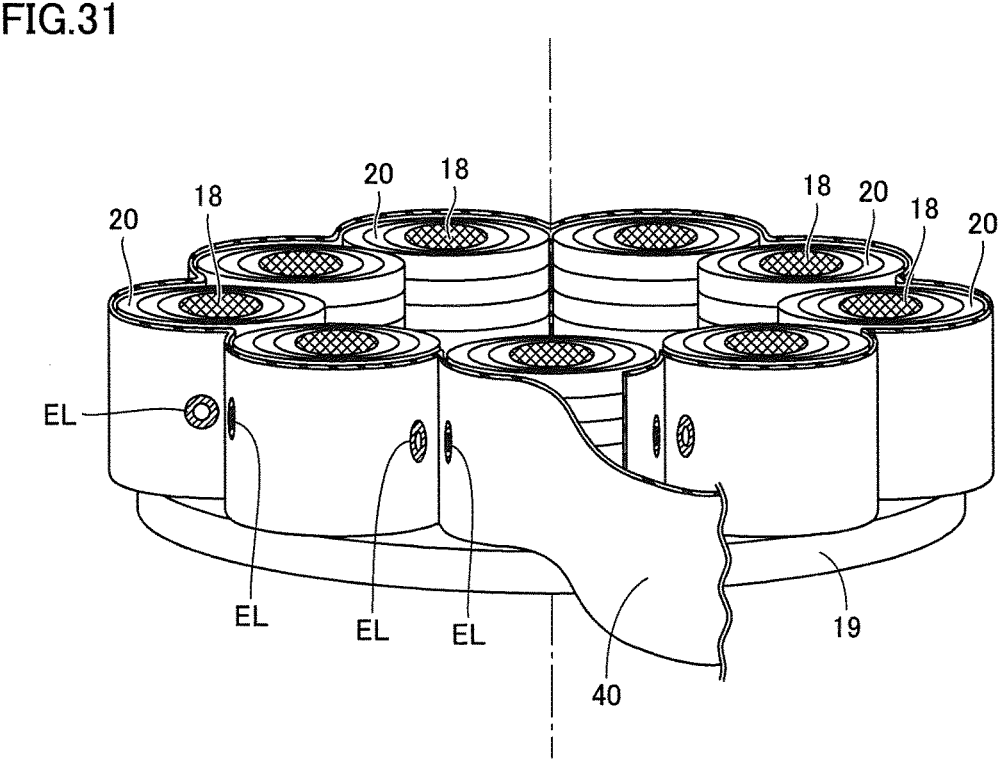
FIG. 31 shows yet another modification of the first embodiment.

It is to be noted that each electrode EL may have a through hole structure, and each terminal of coils 20 may be drawn through the corresponding electrode EL to the outer circumferential side of flexible substrate 40 before being connected to the corresponding electrode EL. Although a pair of electrodes EL in one recess is aligned in the width direction of flexible substrate 40 in the modification of FIG. 30, a pair of electrodes EL in one recess may be aligned in a length direction of flexible substrate 40 as shown in FIG. 31.

Figure 32:
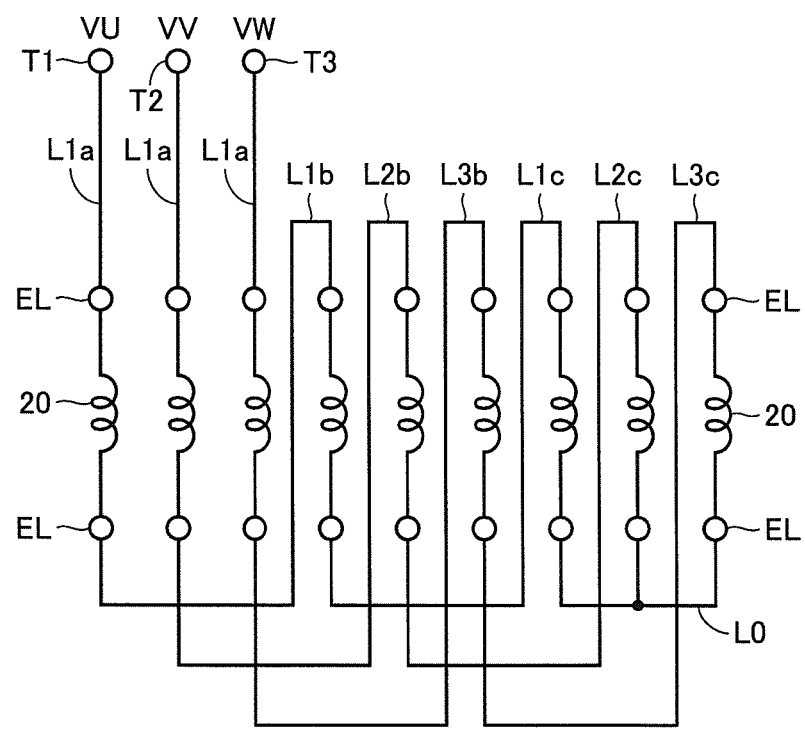
FIG. 32 is a circuit diagram showing yet another modification of the first embodiment.

FIG. 32 shows yet another modification of the first embodiment, which is compared to FIG. 12. In FIG. 12, three first coils 20 are connected in parallel, three second coils 20 are connected in parallel, and three third coils 20 are connected in parallel, whereas in the modification of FIG. 32, three first coils 20 are connected in series, three second coils 20 are connected in series, and three third coils 20 are connected in series.

That is, nine coils 20 are divided into groups each including three coils. Each of the three groups includes first to third coils 20. Each coil 23 has two terminals connected to two electrodes EL adjacent to this coil 23, respectively. A surface of print substrate 23 is provided with a plurality of wiring patterns L0, L1a to L1c, L2a to L2c, and L3a to L3c. Three electrodes EL connected to one terminals of first to third coils 20 of the third group are connected together by wiring pattern L0. Wiring pattern L0 serves as a neutral point of nine coils 20.

Three electrodes EL connected to the other terminals of first to third coils 20 of the third group are connected to three electrodes EL connected to one terminals of first to third coils 20 of the second group via wiring patterns L1c L3c, respectively. Three electrodes EL connected to the other terminals of first to third coils 20 of the second group are connected to three electrodes EL connected to one terminals of first to third coils 20 of the first group via wiring patterns L1b L3b, respectively.

Three electrodes EL connected to the other terminals of first to third coils 20 of the first group are connected to power supply terminals T1 to T3, respectively. Power supply terminals T1 to T3 are connected to first to third power supply lines from controller 25 (see FIG. 15), respectively. Controller 25 supplies driving voltage VU to each first coil 20 via the first power supply line and wiring patterns L1a to L1c, supplies driving voltage VV to each second coil 20 via the second power supply line and wiring patterns L2a to L2c, and supplies driving voltage VW to each third coil 20 via the third power supply line and wiring patterns L3a to L3c. The same effect as that in the first embodiment can be obtained in this modification as well.

[Second Embodiment]

FIG. 33 is a cross-sectional view showing a substantial part of a centrifugal blood pump apparatus according to a second embodiment of the present invention, which is compared to FIG. 4. This centrifugal blood pump apparatus shown in FIG. 33 is different from the first embodiment in that there is a gap between the plurality of permanent magnets 17.

FIG. 34 (a) shows a magnetic field between permanent magnets 17 and 17 in the second embodiment, and FIG. 34 (b) shows a magnetic field between permanent magnets 17 and 17 in the first embodiment. As can be seen from FIGS. 34 (a) and (b), when permanent magnet 17 in the second embodiment and permanent magnet 17 in the first embodiment have the same weight, magnetic flux density between permanent magnets 17 and 17 is higher in the second embodiment, and a magnetic field around permanent magnets 17 is stronger in the second embodiment. In the second embodiment, therefore, a magnetic coupling force between permanent magnets 17 in impeller 10 and magnetic elements 18 and coils 20 in motor chamber 8 can be increased. Accordingly, the rotational torque of impeller 10 can be increased while the small dimensions of the apparatus are maintained.

Figure 35:
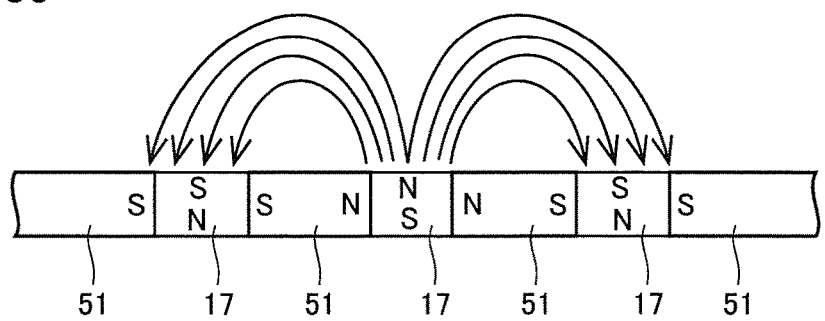
FIG. 35 shows a modification of the second embodiment.

In a modification of FIG. 35, the plurality of permanent magnets 17 and a plurality of permanent magnets 51 are embedded in shroud 12. The number of permanent magnets 51 is the same as the number of permanent magnets 17. Permanent magnets 51 are magnetized in a circumferential direction (rotation direction of impeller 10). The plurality of permanent magnets 17 and the plurality of permanent magnets 51 are alternately arranged one by one in the Halbach array at regular angular intervals along the same circle. In other words, permanent magnet 17 having the N-pole toward dividing wall 6 and permanent magnet 17 having the S-pole toward dividing wall 6 are alternately arranged at regular angular intervals along the same circle.

The N-pole of each permanent magnet 51 is arranged toward permanent magnet 17 having the N-pole toward dividing wall 6, and the S-pole of each permanent magnet 51 is arranged toward permanent magnet 17 having the S-pole toward dividing wall 6. The plurality of permanent magnets 17 have the same shape, and the plurality of permanent magnets 51 have the same shape. Permanent magnets 17 may have a shape the same as or different from the shape of permanent magnets 51.

In this modification, attractive force between permanent magnets 17 and magnetic elements 18 can be suppressed and a magnetic flux that causes torque can be increased, thereby minimizing the size of the permanent magnets. That is, the weight of impeller 10 can be minimized, and energy efficiency can be enhanced even with a wide motor gap.

Figure 36:
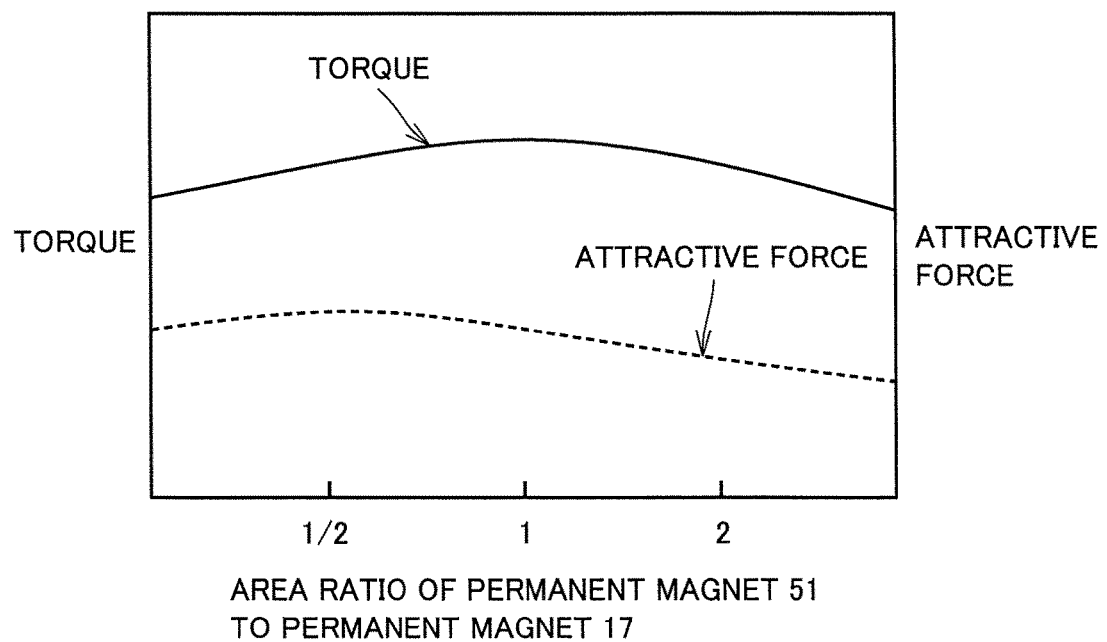
FIG. 36 shows an optimal range of an area ratio of a permanent magnet 51 to a permanent magnet 17 shown in FIG. 35.

Furthermore, with a ratio between a surface area of permanent magnet 17 facing dividing wall 6 and a surface area of permanent magnet 51 facing dividing wall 6, the attractive force between permanent magnets 17 and magnetic elements 18 and the magnetic flux that causes torque can be adjusted. FIG. 36 illustrates relation between the attractive force and generated torque, when permanent magnets 17 and permanent magnets 51 have the same total weight, and an area ratio of permanent magnet 51 to permanent magnet 17 is changed. As shown in FIG. 36, when the area ratio of permanent magnet 51 to permanent magnet 17 is set in a range from 1/2 or more to 2 or less, the rotational torque of impeller 10 can be increased while the attractive force between permanent magnets 17 and magnetic elements 18 is suppressed to low level. Therefore, an optimal range of the area ratio of permanent magnet 51 to permanent magnet 17 is from 1/2 or more to 2 or less.

In general, when the Halbach array is used for the purpose of reducing a torque ripple of a motor, an area ratio between permanent magnet 17 and permanent magnet 51 is set between about 5:1 and 3:1. In the present invention, when the motor gap is wide, the area ratio between permanent magnet 17 and permanent magnet 51 can be optimized by being set in a range between 2:1 and 1:2 depending on motor dimensions and the motor gap, in order to strengthen the magnetic field.

[Third Embodiment]

FIG. 37 (a) is a bottom view of a rotor 61 of an axial gap type motor according to a third embodiment of the present invention, seen from the side of a dividing wall 60, and FIG. 37 (b) is a cross-sectional view showing a substantial part of the axial gap type motor seen from the front.

In FIGS. 37 (a) and (b), this axial gap type motor has a structure similar to that of pump unit 1 of the centrifugal blood pump apparatus in the first embodiment, and includes first and second chambers (not shown) partitioned from each other by circular dividing wall 60. The first chamber includes annular rotor 61 rotatably provided along dividing wall 60, and the second chamber includes a stator 70 for driving rotor 61 to rotate with dividing wall 60 interposed therebetween.

Rotor 61 includes an annular support member 62 made of a nonmagnetic material, and a plurality of (e.g., eight) permanent magnets 63 fixed to support member 62. The plurality of permanent magnets 63 are aligned in a rotation direction of rotor 61. Each permanent magnet 63 is magnetized in a direction in which a rotation central axis of rotor 61 extends. Two adjacent permanent magnets 63 have magnetic polarities different from each other. Stator 70 includes a plurality of (e.g., six) magnetic elements 71, a plurality of coils 72, flexible substrate 23, and a yoke 73.

Magnetic element 71 includes a cylindrical portion 71a, and a cap portion 71b joined to an upper end face of cylindrical portion 71a. Coil 72 is wound around cylindrical portion 71a. A lower end face of cylindrical portion 71a is joined to a surface of yoke 73. The arrangement of flexible substrate 23 is as has been illustrated in FIGS. 9 to 12. Flexible substrate 23 is arranged cylindrically to surround the outer circumferences of the plurality of coils 72. Coils 72 have terminals connected to the electrodes formed in bent portions 23a of flexible substrate 23. Flexible substrate 23 has three power supply terminals connected to three pins of a connector (not shown). Rotor 61 can be rotated by applying voltages VU, VV, VW in the power distribution system shifted by 120 degrees to the plurality of coils 72 via the three pins of the connector and wiring patterns L1 to L3 formed on flexible substrate 23.

In the third embodiment, the operation of connecting the three-phase power supply lines from controller 25 to the plurality of coils 72 can be simplified and the size of the apparatus can be reduced as in the first embodiment.

FIGS. 38 (a) and (b) show a modification of the third embodiment, which are compared to FIGS. 37 (a) and (b). Referring to FIGS. 38 (a) and (b), this modification is different from the third embodiment in that there is a gap between the plurality of permanent magnets 63.

As was shown in FIGS. 34 (a) and (b), when permanent magnet 63 in the modification and permanent magnet 63 in the third embodiment have the same weight, magnetic flux density between permanent magnets 63 and 63 is higher in the modification, and a magnetic field around permanent magnets 63 is stronger in the modification. In the modification, therefore, a magnetic coupling force between permanent magnets 63 in rotor 61 and magnetic elements 71 and coils 72 in stator 70 can be increased. Accordingly, the rotational torque of rotor 61 can be increased while the small dimensions of the apparatus are maintained.

In a modification of FIGS. 39 (a) and (b), the plurality of permanent magnets 63 and a plurality of permanent magnets 67 are provided in rotor 61. The number of permanent magnets 67 is equal to the number of permanent magnets 63. Permanent magnets 67 are magnetized in a circumferential direction (rotation direction of rotor 61). The plurality of permanent magnets 63 and the plurality of permanent magnets 67 are alternately arranged one by one in the Halbach array at regular angular intervals along the same circle. In other words, permanent magnet 63 having the N-pole toward dividing wall 60 and permanent magnet 63 having the S-pole toward dividing wall 60 are alternately arranged at regular angular intervals along the same circle.

The N-pole of each permanent magnet 67 is arranged toward permanent magnet 63 having the N-pole toward dividing wall 60, and the S-pole of each permanent magnet 67 is arranged toward permanent magnet 63 having the S-pole toward dividing wall 60. The plurality of permanent magnets 63 have the same shape, and the plurality of permanent magnets 67 have the same shape. Permanent magnets 63 and permanent magnets 67 may have the same shape or different shapes.

In this modification, attractive force between permanent magnets 63 and magnetic elements 71 can be suppressed and a magnetic flux that causes torque can be increased, thereby minimizing the size of the permanent magnets (see FIG. 35). Namely, the weight of rotor 61 can be minimized, and energy efficiency can be enhanced even with a wide motor gap.

Furthermore, with a ratio between a surface area of permanent magnet 63 facing dividing wall 60 and a surface area of permanent magnet 67 facing dividing wall 60, the attractive force between permanent magnets 63 and magnetic elements 71 and the magnetic flux that causes torque can be adjusted. As was shown in FIG. 36, when the area ratio of permanent magnet 67 to permanent magnet 63 is set in a range from 1/2 or more to 2 or less, the rotational torque of rotor 61 can be increased while the attractive force between permanent magnets 63 and magnetic elements 71 is suppressed to low level. Therefore, an optimal range of the area ratio of permanent magnet 67 to permanent magnet 63 is from 1/2 or more to 2 or less.

[Fourth Embodiment]

Figure 40:
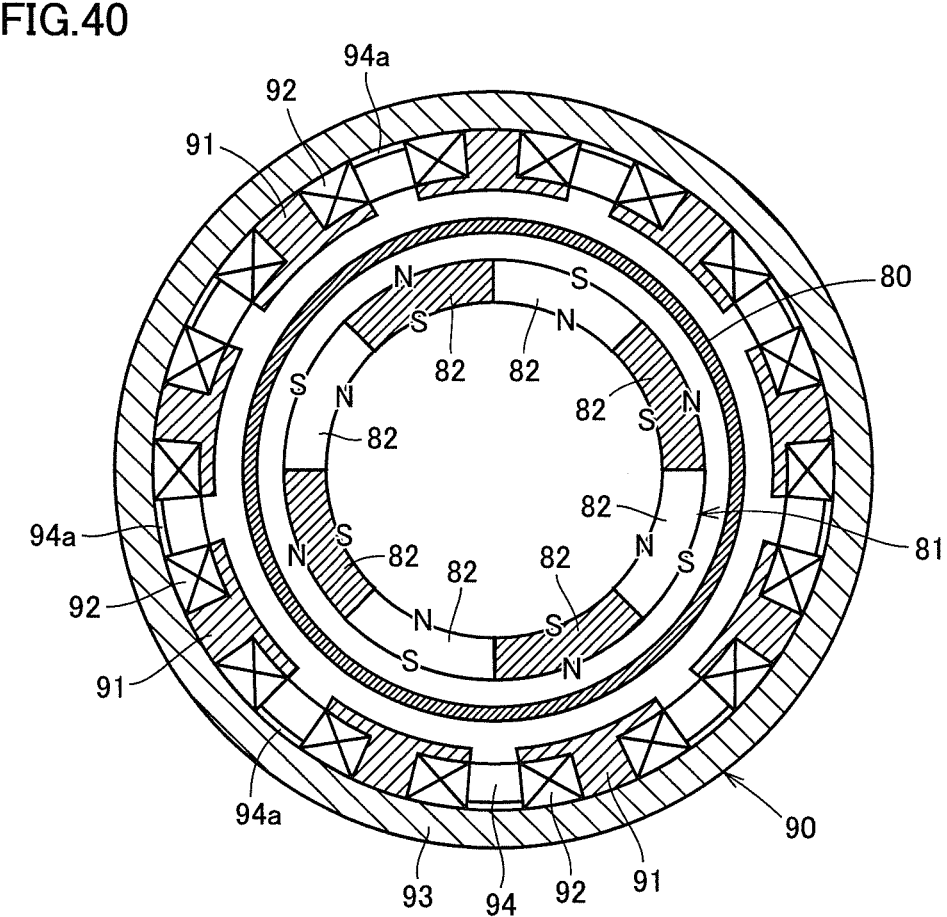
FIG. 40 shows the structure of a radial gap type motor according to a fourth embodiment of the present invention.

FIG. 40 is a plan view showing a substantial part of a radial gap type motor according to a fourth embodiment of the present invention. In FIG. 40, this radial gap type motor has a structure similar to that of the axial gap type motor in FIGS. 37 (a) and (b), and includes first and second chambers (not shown) partitioned from each other by a cylindrical dividing wall 80. The first chamber on an inner side relative to dividing wall 80 includes a cylindrical rotor 81 rotatably provided along dividing wall 80, and the second chamber on an outer side relative to dividing wall 80 includes a stator 90 for driving rotor 81 to rotate with dividing wall 80 interposed therebetween.

Rotor 81 includes a cylindrical support member (not shown) made of a nonmagnetic material, and a plurality of (e.g., eight) permanent magnets 82 fixed to the support member. The plurality of permanent magnets 82 are aligned in a rotation direction of rotor 81. Each permanent magnet 82 is magnetized in a direction (radial direction) orthogonal to the rotation direction of rotor 81. Two adjacent permanent magnets 82 have magnetic polarities different from each other.

Stator 90 includes a plurality of (e.g., nine) magnetic elements 91, a plurality of coils 92, a cylindrical yoke 93, and an annular flexible substrate 94. Magnetic element 91 includes a cylindrical portion, and a cap portion joined to an upper end face of the cylindrical portion. Coil 92 is wound around the cylindrical portion of magnetic element 91. A lower end face of the cylindrical portion of magnetic element 91 is joined to an inner circumferential surface of yoke 94. Flexible substrate 94 abuts a side face on one side (back side in the figure) of each of the plurality of coils 92.

As with flexible substrate 23 shown in FIGS. 9 to 12, flexible substrate 94 includes a plurality of bent portions 94a. The plurality of bent portions 94a are provided at regular angular intervals along the outer circumference of the annular portion of flexible substrate 94, are bent at a right angle to the front side in the figure, and are arranged between the plurality of coils 92, respectively. A surface of each bent portion 94a is provided with two electrodes EL. Each coil 92 has two terminals connected to two electrodes EL adjacent to this coil 92, respectively.

Flexible substrate 94 is provided with four wiring patterns L0 to L3 and three power supply terminals T1 to T3 as described with reference to FIG. 12. Three power supply terminals T1 to T3 are connected to three pins of a connector (not shown). Rotor 81 can be rotated by applying driving voltages VU, VV, VW in the power distribution system shifted by 120 degrees to the plurality of coils 92 via the three pins of the connector and wiring patterns L1 to L3 formed on flexible substrate 94.

In the fourth embodiment, the operation of connecting the three-phase power supply lines from controller 25 to the plurality of coils 92 can be simplified and the size of the apparatus can be reduced as in the first embodiment.

Although flexible substrate 94 in an annular shape is provided in the fourth embodiment, flexible substrate 94 in the shape of a disc may be provided.

Flexible substrate 94 may be provided with, instead of four wiring patterns L0 to L3 as described with reference to FIG. 12, the plurality of wiring patterns L0, L1a to L1c, L2a to L2c, and L3a to L3c shown in FIG. 28.

Flexible substrate 94 may be provided on each of both end faces of the drive unit. In this case, power supply terminals T1 to T3, the plurality of electrodes EL, and wiring patterns L0 to L3 (or wiring patterns L0, L1a to L1c, L2a to L2c, L3a to L3c) may be arranged in a dispersed manner on two flexible substrates 94. For example, power supply terminals T1 to T3, nine electrodes EL, and wiring patterns L1 to L3 shown in FIG. 12 may be provided on one of flexible substrates 94, and nine electrodes EL and wiring pattern L0 may be provided on the other flexible substrate 94.

Figure 41:
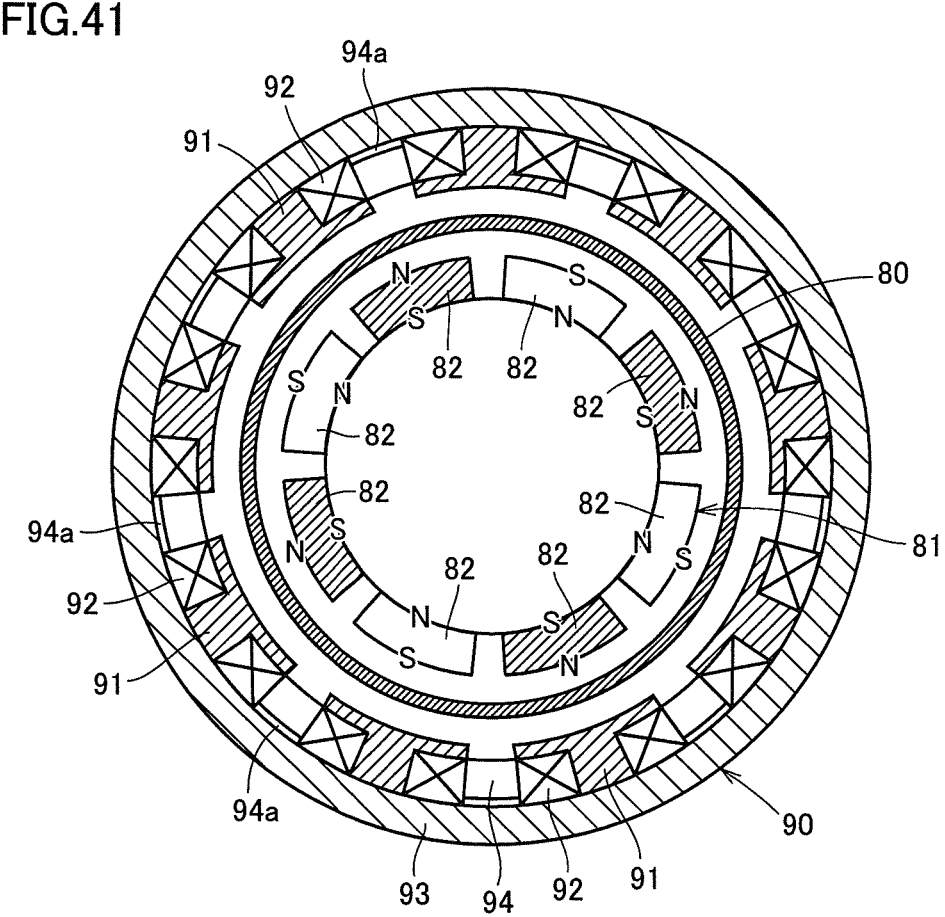
FIG. 41 shows a modification of the fourth embodiment.

FIG. 41 shows a modification of the fourth embodiment, which is compared to FIG. 40. This modification of FIG. 41 is different from the fourth embodiment in that there is a gap between the plurality of permanent magnets 82.

As shown in FIGS. 34 (a) and (b), when permanent magnet 82 in the modification and permanent magnet 82 in the fourth embodiment have the same weight, magnetic flux density between permanent magnets 82 and 82 is higher in the modification, and a magnetic field around permanent magnets 82 is stronger in the modification. In this fourth modification, therefore, a magnetic coupling force between permanent magnets 82 in rotor 81 and magnetic elements 91 and coils 92 in stator 90 can be increased. Accordingly, the rotational torque of rotor 81 can be increased while the small dimensions of the apparatus are maintained.

Figure 42:
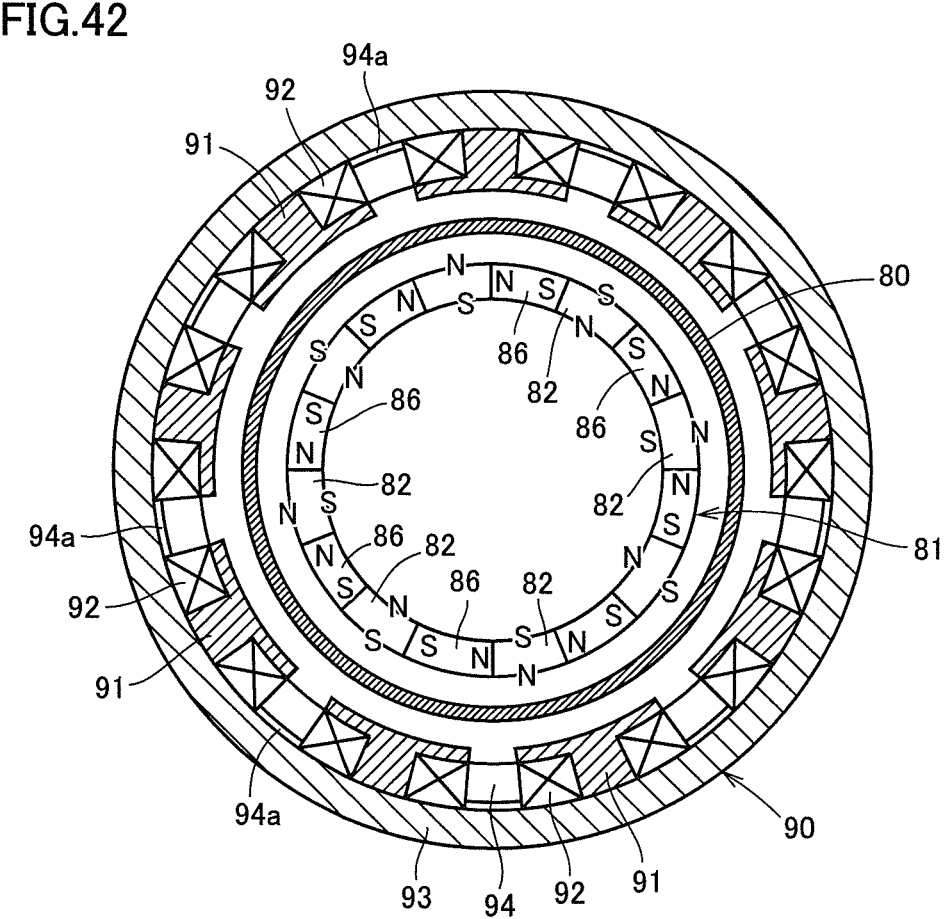
FIG. 42 shows another modification of the fourth embodiment.

In a modification of FIG. 42, rotor 81 includes the plurality of permanent magnets 82 and a plurality of permanent magnets 86. The number of permanent magnets 86 is equal to the number of permanent magnets 82. Permanent magnets 86 are magnetized in a circumferential direction (rotation direction of rotor 81). The plurality of permanent magnets 82 and the plurality of permanent magnets 86 are alternately arranged one by one in the Halbach array at regular angular intervals along the same circle. In other words, permanent magnet 82 having the N-pole toward dividing wall 80 and permanent magnet 82 having the S-pole toward dividing wall 80 are alternately arranged with a gap therebetween at regular angular intervals along the same circle.

The N-pole of each permanent magnet 86 is arranged toward permanent magnet 82 having the N-pole toward dividing wall 80, and the S-pole of each permanent magnet 86 is arranged toward permanent magnet 82 having the S-pole toward dividing wall 80. The plurality of permanent magnets 82 have the same shape, and the plurality of permanent magnets 86 have the same shape. Permanent magnets 82 and permanent magnets 86 may have the same shape or different shapes.

In this modification, attractive force between permanent magnets 82 and magnetic elements 91 can be suppressed and a magnetic flux that causes torque can be increased, thereby minimizing the size of the permanent magnets (see FIG. 35). Namely, the weight of rotor 81 can be minimized, and energy efficiency can be enhanced even with a wide motor gap.

Furthermore, with a ratio between a surface area of permanent magnet 82 facing dividing wall 80 and a surface area of permanent magnet 86 facing dividing wall 80, the attractive force between permanent magnets 82 and magnetic elements 91 and the magnetic flux that causes torque can be adjusted. As was shown in FIG. 36, when the area ratio of permanent magnet 86 to permanent magnet 82 is set in a range from 1/2 or more to 2 or less, the rotational torque of rotor 81 can be increased while the attractive force between permanent magnets 82 and magnetic elements 91 is suppressed to low level. Therefore, an optimal range of the area ratio of permanent magnet 86 to permanent magnet 82 is from 1/2 or more to 2 or less.

Figure 43:
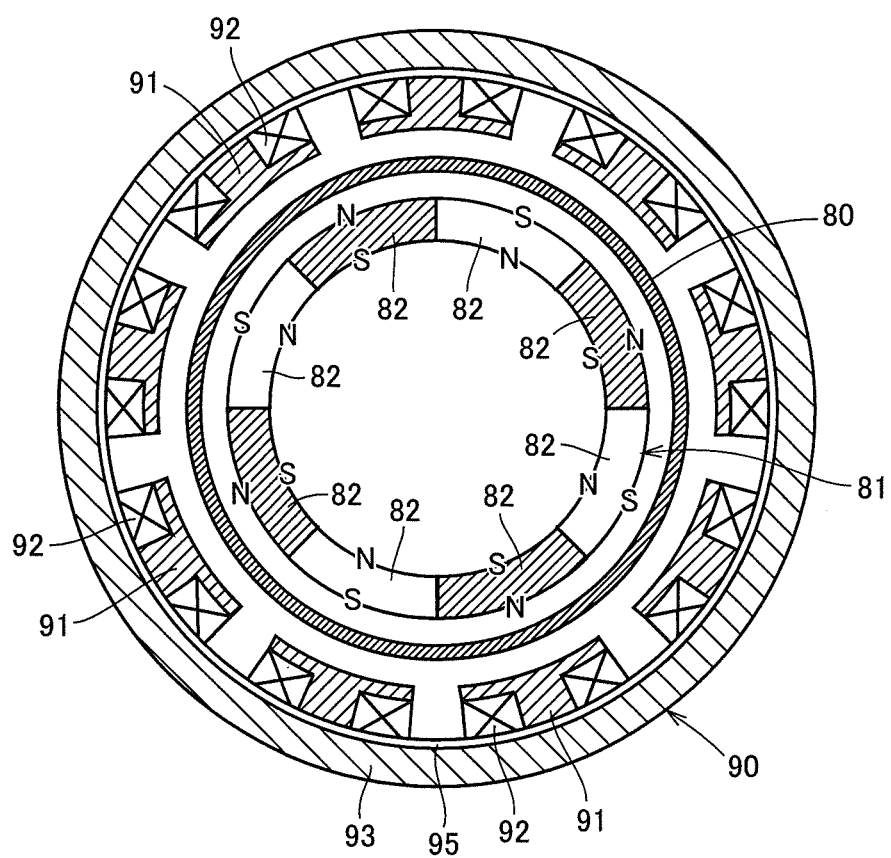
FIG. 43 shows yet another modification of the fourth embodiment.

In a modification of FIG. 43, a strip-shaped flexible substrate 95 is arranged annularly (cylindrically) along one side of all coils 92. Flexible substrate 95 is provided with an electrode (not shown) to face each terminal of each coil 92. Each coil 92 has each terminal connected to the corresponding electrode. The arrangement of flexible substrate 95 is similar to that of flexible substrate 23 described with reference to FIGS. 9 to 12, 26 to 28, and 32.

That is, flexible substrate 95 is provided with wiring patterns L0 to L3 (or wiring patterns L0, L1a to L1c, L2a to L2c, L3a to L3c) and three power supply terminals T1 to T3 as described with reference to FIG. 12 (or FIG. 32). Three power supply terminals T1 to T3 are connected to three pins of a connector (not shown). Rotor 81 can be rotated by applying driving voltages VU, VV, VW in the power distribution system shifted by 120 degrees to the plurality of coils 92 via the three pins of the connector and wiring patterns L1 to L3 (or wiring patterns L1a to L1c, L2a to L2c, L3a to L3c) formed on flexible substrate 95. The same effect as that in the fourth modification can be obtained in this modification as well.

Flexible substrate 95 may be provided on each of both end faces of the drive unit. In this case, power supply terminals T1 to T3, the plurality of electrodes EL, and wiring patterns L0 to L3 (or L0, L1a to L1c, L2a to L2c, L3a to L3c) may be arranged in a dispersed manner on two flexible substrates 95. For example, power supply terminals T1 to T3, nine electrodes EL and wiring patterns L1 to L3 shown in FIG. 12 may be provided on one of flexible substrates 95, and nine electrodes EL and wiring pattern L0 may be provided on the other flexible substrate 95.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

REFERENCE SIGNS LIST 1 pump unit; 2 housing; 3 body portion; 4 blood inlet port; 5 blood outlet port; 6, 60, 80 dividing wall; 7 blood chamber; 8 motor chamber; 10 impeller; 10a through hole; 11, 12 shroud; 13 vane; 14 blood passage; 15 to 17, 51, 63, 67, 82, 86 permanent magnet; 18, 35, 37 to 39, 71, 91 magnetic element; 19, 36, 73, 93 yoke; 20, 72, 92 coil; 21, 22 groove for hydrodynamic bearing; 23, 40, 94, 95 flexible substrate; 23*a*, 40*a*, 94*a* bent portion; 24 connector; 24*a* to 24*c* pin; 25 controller; 26 motor control circuit; 27, 32, 33 power amplifier; 34 switch; 61, 81 rotor; 70, 90 stator; EL electrode; L0 to L3 wiring pattern; T1 to T3 power supply terminal.

We claim:

1. A rotation drive device comprising:
a rotor in a first chamber, wherein said rotor is an impeller for delivering fluid by centrifugal force during rotation; and
said drive unit including:
a plurality of first magnetic elements provided facing said rotor,
a plurality of coils wound around said plurality of first magnetic elements, respectively, for generating a rotating magnetic field,
a connector for externally receiving a driving voltage, and
a flexible substrate connected to said plurality of coils and said connector, wherein:
said flexible substrate comprises a wiring pattern for supplying said driving voltage externally provided via said connector to said plurality of coils,
said flexible substrate comprises a strip which has a length at least partially arranged to surround the outer circumferences of said plurality of coils, and
said flexible substrate comprises a plurality of electrodes connected with said plurality of coils, wherein said plurality of electrodes are arranged in pairs which are located along said length, each pair comprising two electrodes located side-by-side in an axial direction of the drive unit at a common distance along said length, and each pair of electrodes connected with two leads from one of the plurality of coils.

2. The rotation drive device according to claim 1, wherein said rotor includes a plurality of first permanent magnets, each first permanent magnet is magnetized in a direction orthogonal to a rotation direction of said rotor,
the magnetic polarities of adjacent ones of said first permanent magnets oppose each other, and
said plurality of first magnetic elements are arranged to face said plurality of first permanent magnets.

3. The rotation drive device according to claim 2, wherein said rotor further includes a plurality of second permanent magnets,
said plurality of second permanent magnets are interposed between said plurality of first permanent magnets, respectively,
each second permanent magnet is magnetized in the rotation direction of said rotor,
each second permanent magnet has a first magnetic polarity at a first end toward one of two first permanent magnets adjacent thereto having a first magnetic polarity toward said rotor, and
each second permanent magnet has a second magnetic polarity at a second end toward one of two first permanent magnets adjacent thereto having a second magnetic polarity toward said rotor.

4. The rotation drive device according to claim 1, wherein said rotor and said drive unit are spaced apart from each other in a direction in which a rotation central axis of said rotor extends, and said plurality of first magnetic elements are aligned in a rotation direction of said rotor.

5. The rotation drive device according to claim 4, wherein said flexible substrate is at least partially arranged cylindrically to surround the outer circumferences of said plurality of coils, with a plurality of clearances formed between an inner circumferential surface of said flexible substrate and outer circumferential surfaces of said plurality of coils, and
said plurality of electrodes are arranged in a dispersed manner in said flexible substrate so as to be positioned in said plurality of clearances.

6. The rotation drive device according to claim 5, wherein said flexible substrate in the shape of a strip includes a plurality of bent portions on one side or both sides in a width direction of said flexible substrate,
said plurality of bent portions are arranged in a dispersed manner in a length direction of said flexible substrate so as to be positioned in said plurality of clearances, each bent portion being bent into the corresponding clearance, and
said plurality of electrodes are formed in said plurality of bent portions.

7. The rotation drive device according to claim 4, wherein said plurality of electrodes are aligned in a length direction of said flexible substrate, and
each electrode is provided in a substantially central portion in a width direction of said flexible substrate.

8. The rotation drive device according to claim 4, wherein said flexible substrate is at least partially arranged in a corrugated shape along the outer circumferences of said plurality of coils, with a plurality of recesses formed on an outer side of said flexible substrate,
said flexible substrate in the shape of a strip includes a plurality of bent portions on one side or both sides in a width direction of said flexible substrate,
said plurality of bent portions are arranged in a dispersed manner in a length direction of said flexible substrate so as to be positioned in said plurality of recesses, each bent portion being bent into the corresponding recess, and
said plurality of electrodes are arranged in a dispersed manner in said plurality of bent portions.

9. The rotation drive device according to claim 4, wherein said flexible substrate is at least partially arranged in a corrugated shape along the outer circumferences of said plurality of coils, with a plurality of recesses formed on an outer side of said flexible substrate, and
said plurality of electrodes are arranged in a dispersed manner in a length direction of said flexible substrate so as to be positioned in said plurality of recesses.

10. The rotation drive device according to claim 4, wherein
said flexible substrate has a length at least 1.25 times the length of an outer circumference of said drive unit.

11. The rotation drive device according to claim 4, wherein
said drive unit further includes a second magnetic element in the shape of a disc, said second magnetic element being provided to face said rotor with said plurality of first magnetic elements interposed therebetween, and being coupled to said plurality of first magnetic elements, and
said plurality of coils are arranged on a surface of said second magnetic element along an outer circumference of said second magnetic element.

12. The rotation drive device according to claim 1, wherein
said rotor and said drive unit are spaced apart from each other in a radial direction of said rotor, and
said plurality of first magnetic elements are aligned in a rotation direction of said rotor.

13. The rotation drive device according to claim 12, wherein
said drive unit further includes a second magnetic element in a cylindrical shape, said second magnetic element being provided to face said rotor with said plurality of first magnetic elements interposed therebetween, and being coupled to said plurality of first magnetic elements.

14. The rotation drive device according to claim 1, comprising a housing having the first chamber and a second chamber partitioned from each other by a dividing wall, wherein
said rotor is provided in said first chamber along said dividing wall, and said drive unit is provided in said second chamber for driving said rotor to rotate with said dividing wall interposed there between.

15. The rotation drive device according to claim 1, wherein
each of said plurality of coils comprises two terminals located side-by-side at a common angular position about an axis of the coil.

16. A centrifugal pump apparatus including a housing having first and second chambers partitioned from each other by a dividing wall, an impeller provided in said first chamber along said dividing wall, for delivering fluid by centrifugal force during rotation, and a drive unit provided in said second chamber for driving said impeller to rotate with said dividing wall interposed therebetween, said centrifugal pump apparatus comprising:
a plurality of first permanent magnets provided in said impeller and attracted by said drive unit, wherein
said drive unit includes
a plurality of magnetic elements arranged to face said plurality of first permanent magnets,
a plurality of coils provided correspondingly to said plurality of magnetic elements respectively and each wound around the corresponding magnetic element, for generating a rotating magnetic field,
a connector fixed to said housing and externally receiving a driving voltage, and
a flexible substrate connected to said plurality of coils and said connector, wherein
said flexible substrate comprises a strip which has a length at least partially arranged to surround the outer circumferences of said plurality of coils, and
said flexible substrate comprises a plurality of electrodes connected with said plurality of coils, wherein said plurality of electrodes are arranged in pairs which are located along said length, each pair comprising two electrodes located side-by-side in an axial direction of the drive unit at a common distance along said length, and each pair of electrodes connected with two leads from one of the plurality of coils.

17. The centrifugal pump apparatus according to claim 16, wherein
said fluid is blood, and
said centrifugal pump apparatus is used for circulating said blood.

18. The centrifugal pump apparatus according to claim 16 further comprising:
a second permanent magnet provided in one surface of said impeller; and
a third permanent magnet provided in an inner wall of said first chamber facing said impeller, for attracting said second permanent magnet;
wherein during rotation of said impeller, a first attractive force between said second and third permanent magnets and a second attractive force between said plurality of first permanent magnets and said plurality of magnetic elements are balanced with each other in a substantially central portion of a movable range of said impeller in said first chamber.

19. The centrifugal pump apparatus according to claim 18, wherein a first groove for hydrodynamic bearing is formed in one surface of said impeller or in the inner wall of said first chamber facing the one surface, and a second groove for hydrodynamic bearing is formed in the other surface of said impeller or in said dividing wall facing the other surface.

20. The centrifugal pump apparatus according to claim 19, wherein
said flexible substrate is at least partially arranged cylindrically to surround the outer circumferences of said plurality of coils, with a plurality of clearances formed between an inner circumferential surface of said flexible substrate and outer circumferential surfaces of said plurality of coils, and
said plurality of electrodes are arranged in a dispersed manner in said flexible substrate so as to be positioned in said plurality of clearances.

21. The centrifugal pump apparatus according to claim 20, wherein
said flexible substrate in the shape of a strip includes a plurality of bent portions on one side or both sides in a width direction of said flexible substrate,
said plurality of bent portions are arranged in a dispersed manner in a length direction of said flexible substrate so as to be positioned in said plurality of clearances, each bent portion being bent into the corresponding clearance, and
said plurality of electrodes are formed in said plurality of bent portions.

22. The centrifugal pump apparatus according to claim 19, wherein
said plurality of electrodes are aligned in a length direction of said flexible substrate, and
each electrode is provided in a substantially central portion in a width direction of said flexible substrate.

23. The centrifugal pump apparatus according to claim 19, wherein
said flexible substrate is at least partially arranged in a corrugated shape along the outer circumferences of said plurality of coils, with a plurality of recesses formed on an outer side of said flexible substrate,
said flexible substrate in the shape of a strip includes a plurality of bent portions on one side or both sides in a width direction of said flexible substrate,
said plurality of bent portions are arranged in a dispersed manner in a length direction of said flexible substrate so as to be positioned in said plurality of recesses, each bent portion being bent into the corresponding recess, and
said plurality of electrodes are arranged in a dispersed manner in said plurality of bent portions.

24. The centrifugal pump apparatus according to claim 19, wherein said flexible substrate is at least partially arranged in a corrugated shape along the outer circumferences of said plurality of coils, with a plurality of recesses formed on an outer side of said flexible substrate, and said plurality of electrodes are arranged in a dispersed manner in a length direction of said flexible substrate so as to be positioned in said plurality of recesses.

25. The centrifugal pump apparatus according to claim 19, wherein said flexible substrate has a length at least 1.25 times the length of an outer circumference of said drive unit.

26. he centrifugal pump apparatus according to claim 16, wherein each of said plurality of coils comprises two terminals located side-by-side at a common angular position about an axis of the coil.

\* \* \* \* \*

UNITED STATES PATENT AND TRADEMARK OFFICE
CERTIFICATE OF CORRECTION

PATENT NO. : 9,850,906 B2
APPLICATION NO. : 14/034730
DATED : December 26, 2017
INVENTOR(S) : Takayoshi Ozaki et al.

It is certified that error appears in the above-identified patent and that said Letters Patent is hereby corrected as shown below:

In the Claims

Column 25, Line 14, Claim 1:
Lines 11-15 currently read as "A rotation drive device comprising: a rotor in a first chamber, wherein said rotor is an impeller for delivering fluid by centrifugal force during rotation; and said drive unit including:"
Please include "a drive unit for driving said rotor to rotate," so it will instead read: "A rotation drive device comprising: a rotor in a first chamber, wherein said rotor is an impeller for delivering fluid by centrifugal force during rotation; and a drive unit for driving said rotor to rotate, said drive unit including:"

Column 27, Line 22, Claim 14:
Please change "said dividing wall interposed there between" to "said dividing wall interposed therebetween"

Column 29, Line 12, Claim 26:
Please change "he centrifugal pump apparatus according to claim 16" to "The centrifugal pump apparatus according to claim 16"

Signed and Sealed this
Twenty-fourth Day of April, 2018

Andrei Iancu
*Director of the United States Patent and Trademark Office*